(12) United States Patent
Welker et al.

(10) Patent No.: US 8,110,695 B2
(45) Date of Patent: Feb. 7, 2012

(54) COMPOUNDS AND COMPOSITIONS CONTAINING SILICON AND/OR OTHER HETEROATOMS AND/OR METALS AND METHODS OF MAKING AND USING THEM

(76) Inventors: Mark E. Welker, Clemmons, NC (US); Ramakrishna R. Pidaparthi, Raleigh, NC (US)

( * ) Notice: Subject to any disclaimer, the term of this patent is extended or adjusted under 35 U.S.C. 154(b) by 0 days.

(21) Appl. No.: 12/447,360

(22) PCT Filed: Oct. 31, 2007

(86) PCT No.: PCT/US2007/022872
§ 371 (c)(1),
(2), (4) Date: Apr. 27, 2009

(87) PCT Pub. No.: WO2008/054718
PCT Pub. Date: May 8, 2008

(65) Prior Publication Data
US 2010/0056801 A1    Mar. 4, 2010

Related U.S. Application Data

(60) Provisional application No. 60/855,428, filed on Oct. 31, 2006.

(51) Int. Cl.
*C07F 7/07* (2006.01)
*C07F 7/02* (2006.01)
(52) U.S. Cl. ........................................ 556/408; 556/464
(58) Field of Classification Search .................. None
See application file for complete search history.

(56) References Cited

U.S. PATENT DOCUMENTS 4,837,339 A * 6/1989 Sato ............................... 549/214

OTHER PUBLICATIONS

Dorwald F. A. Side Reactions in Organic Synthesis, 2005, Wiley: VCH, Weinheim. Preface and Chap. 1.*
Pidaparthi et al. Organic Letters, 2007, vol. 7, No. 9, pp. 1623-1626, published online Apr. 5, 2007.*
Vronkov et al. Zhurnal Obshchei Khimii (1984), 54 (2), p. 475-6.*
International Search Report for International Application No. PCT/US2007/022872 dated Mar. 11, 2008.
Written Opinion of the International Searching Authority for International Application No. PCT/US2007/022872 dated Mar. 11, 2008.
Pidaparthi, Ramakrishna R. et al., "Preparation of 2- trialkylsiloxy-substituted 1,3 dienes and their Diels-Alder/ cross-coupling reactions," Organic Letters, 9(9), 1623-1626, Coden: ORLEF7, ISSN: 1523-7060, 2007, XP 002472247.

* cited by examiner

*Primary Examiner* — Rebecca Anderson
*Assistant Examiner* — Alicia L Otton
(74) *Attorney, Agent, or Firm* — Leak & Schroeder, PLLC; T. Benjamin Schroeder; Frank W. Leak

(57) ABSTRACT

The present invention relates to compounds, intermediates, compositions, and methods of making compounds and intermediates related to the compounds of Formula (I) and/or Formula (II) and/or Formula (III) and/or Formula (IV) and/or Formula (VI) and/or Formula (VII) as disclosed herein wherein the various substituents are as defined in the written description.

18 Claims, 2 Drawing Sheets

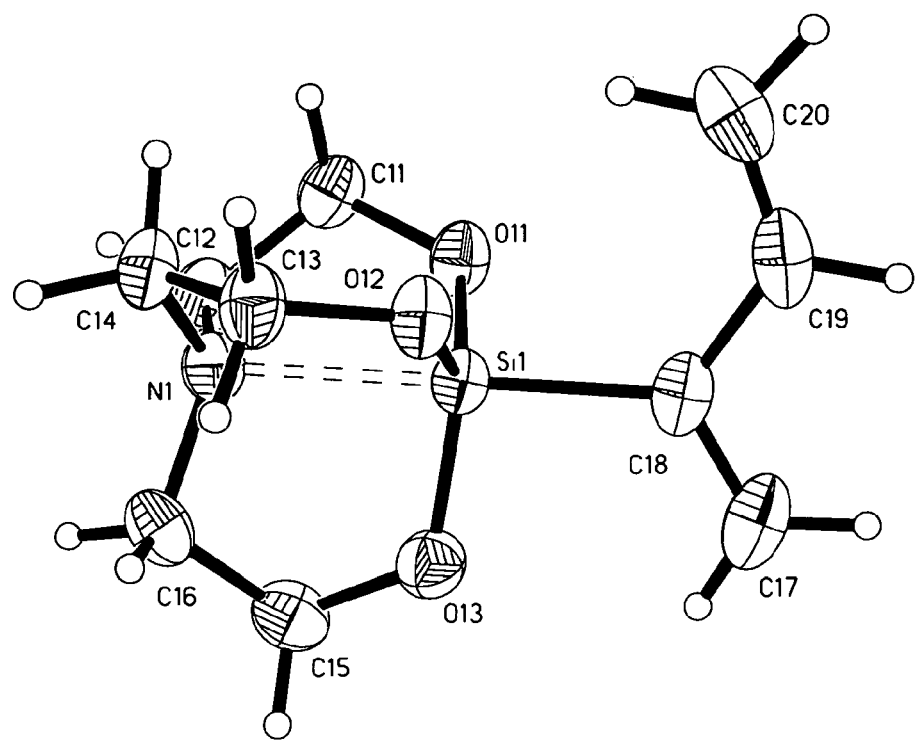
1A
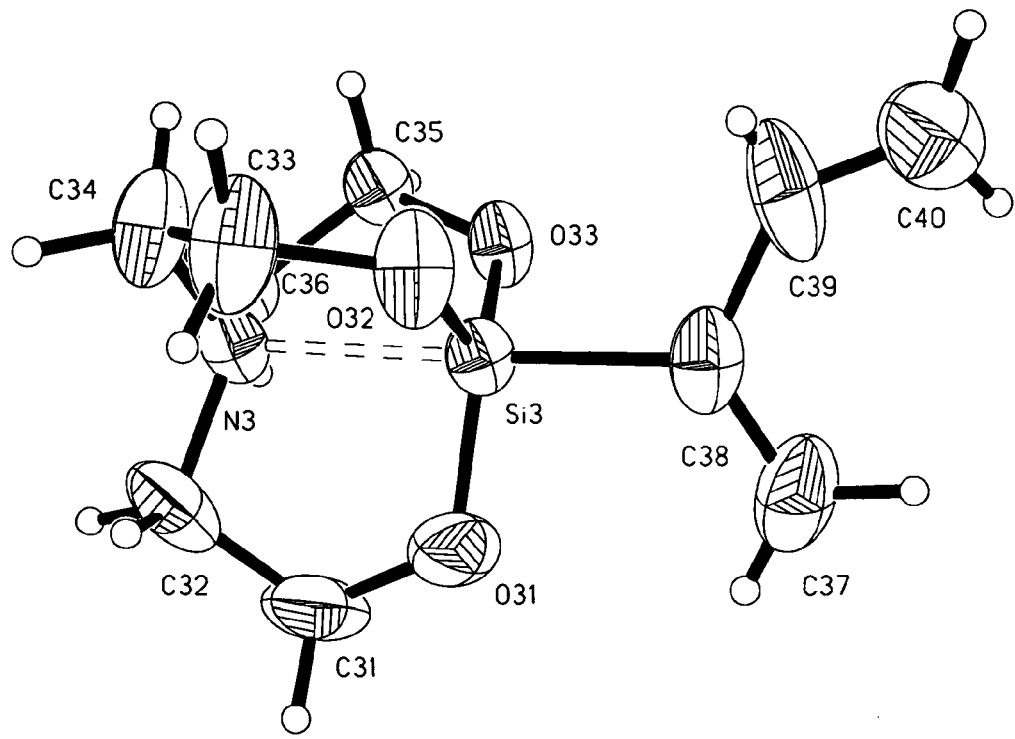
1B

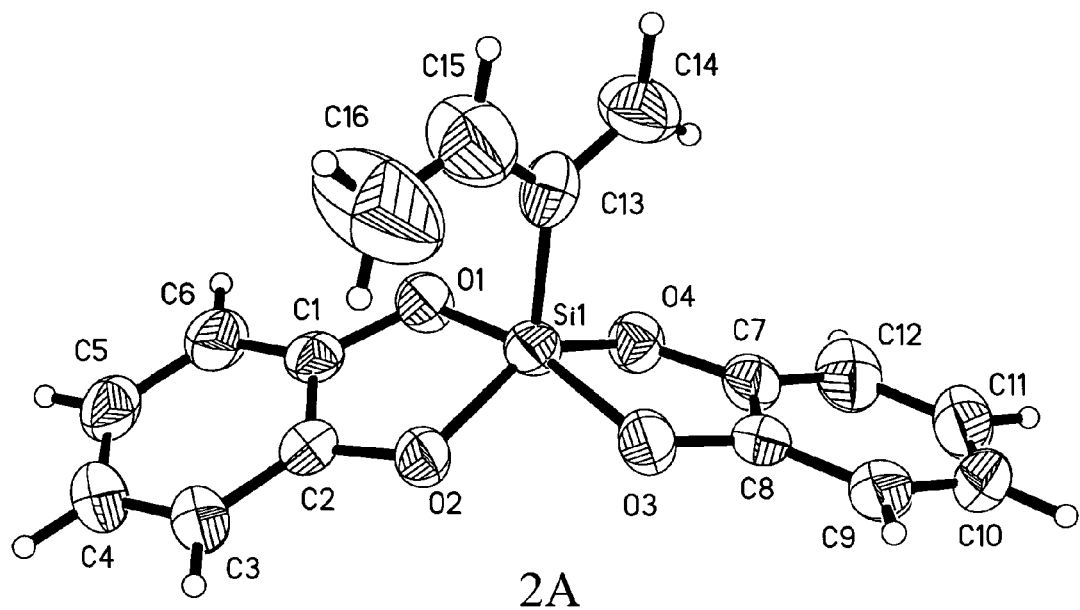
2A
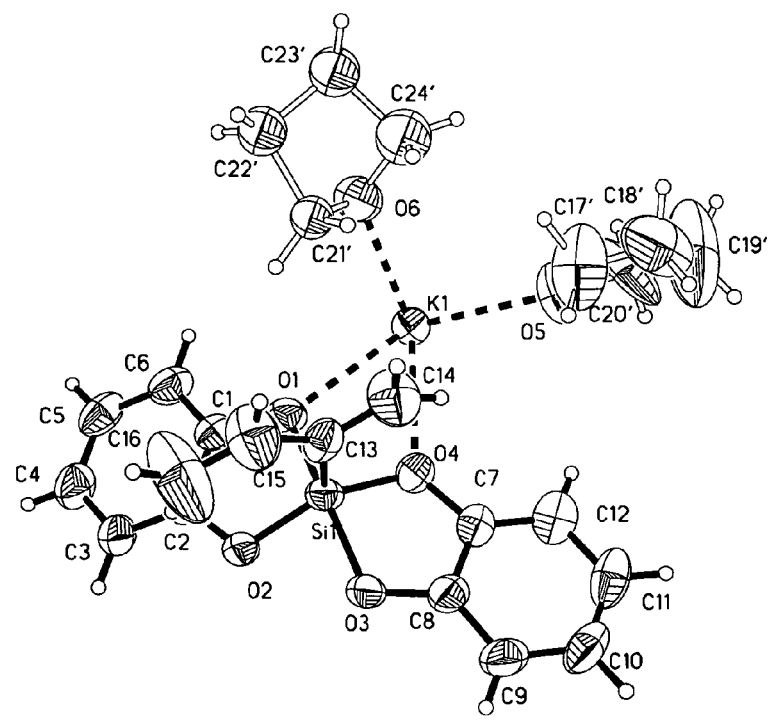
2B

COMPOUNDS AND COMPOSITIONS CONTAINING SILICON AND/OR OTHER HETEROATOMS AND/OR METALS AND METHODS OF MAKING AND USING THEM

This application claims priority under 35 USC §119(e) to U.S. Provisional Application 60/855,428 filed Oct. 31, 2006, the entire contents of which is incorporated by reference in its entirety.

STATEMENT REGARDING FEDERALLY SPONSORED RESEARCH OR DEVELOPMENT

This invention was made through the support of National Science Foundation Grant No. CHE-0450722. The Federal Government may retain certain license rights in this invention.

FIELD OF THE INVENTION

The present invention relates to compounds, intermediates, compositions, and methods of making compounds and intermediates related to the compounds of Formula I and/or Formula II and/or Formula III and/or Formula IV and/or Formula VI and/or Formula VII:

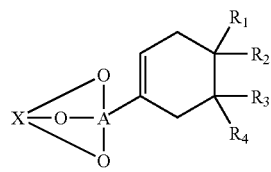

Formula I

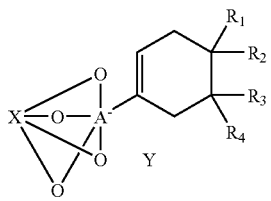

Formula II

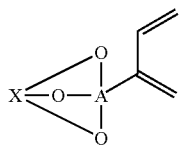

Formula III

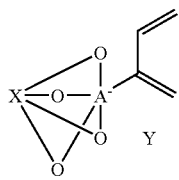

Formula IV

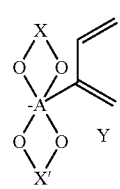

Formula VI

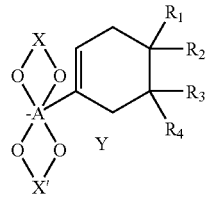

Formula VII wherein A is a member selected from the group consisting of silicon, platinum, rhodium, boron, arsenic and palladium;

X and X' are independently an aliphatic hydrocarbon chain or aromatic group which may be selected from one or more of the following alkyl, alkenyl, alkynyl, aryl, heteroaryl, heterocyclyl, wherein all of the alkyl, alkenyl, alkynyl, aryl, heteroaryl, heterocyclyl groups may contain one or more heteroatoms selected from the group consisting of nitrogen, phosphorous, arsenic, antimony, bismuth, germanium, tin, oxygen, sulfur, selenium, tellurium, boron, aluminum, gallium, indium, germanium, and silicon, and wherein all of the alkyl, alkenyl, alkynyl, aryl, heteroaryl, heterocyclyl groups also may be optionally substituted by one or more of the following, alkyl, alkenyl, alkynyl, aryl, heteroaryl, heterocyclyl, halo, cyano, oxo, hydroxy, mercapto, sulfonyl, sulfoxy, amino, imino, alkylthio, alkoxy, alkoxyalkyl, mono-alkylamino, di-alkylamino, nitro, nitroso, and thioxo. All of these substituents may, in turn, be optionally substituted with one or more substituents independently selected from the group consisting of halogen, hydroxy, cyano, carboxy, thiol, sulfo, nitro, nitroso, oxo, thioxo, and imino.

$R_1$, $R_2$, $R_3$, and $R_4$ are each independently selected from the group consisting of alkyl, alkenyl, alkynyl, aryl, heteroaryl, heterocyclyl, halo, cyano, oxo, hydroxy, mercapto, sulfonyl, sulfoxy, amino, imino, alkylthio, alkoxy, alkoxyalkyl, mono-alkylamino, di-alkylamino, nitro, nitroso, and thioxo or $R_1$ and $R_2$ together with the atoms connected to them or $R_3$ and $R_4$ together with the atoms connected to them may form a spiro $C_{4-8}$ cycloalkyl group that may optionally contain one or more heteroatoms selected from the group consisting of nitrogen, phosphorous, arsenic, antimony, bismuth, germanium, tin, oxygen, sulfur, selenium, tellurium, boron, aluminum, gallium, indium, germanium, and silicon; or $R_1$ and $R_3$ together with the atoms connected to them or $R_2$ and $R_4$ together with the atoms connected to them may form a $C_{3-10}$ cycloalkyl group that may optionally contain one or more heteroatoms selected from the group consisting of nitrogen, phosphorous, arsenic, antimony, bismuth, germanium, tin, oxygen, sulfur, selenium, tellurium, boron, aluminum, gallium, indium, germanium, and silicon.

Y is a counterion such as an alkali metal or other appropriate positively charged ion.

BACKGROUND OF THE INVENTION

U.S. Pat. No. 4,837,339 to Sato (Sato '339) discloses the synthesis of 4-substituted-1,2,3,6-tetrahydrophthalic acid anhydride compounds represented by the below formula A:

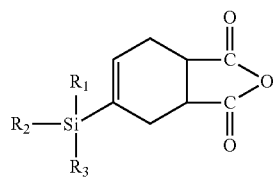

Formula A where R₁ represents a lower alkoxy group, and R₂ and R₃ each represents a lower alkyl group or a lower alkoxy group, said 4-substituted-1,2,3,6-tetrahydrophthalic acid anhydride being liquid. The above compounds from formula A can be made by a Diels Alder type reaction wherein a 2-substituted-1,3-butadiene is reacted with maleic acid anhydride to generate the compounds as shown in Formula A. The general reaction scheme is shown below:

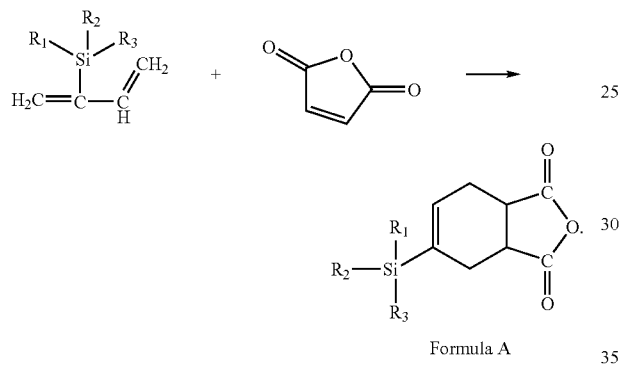

Formula A

The compounds generated by the above reaction are useful as starting materials for silicone-containing polyester resins, polyamide resins and addition type polyimide resins; silane coupling agents, particularly, coupling agents for polyimide resins; plasticizers for vinyl chloride resins or the like, curing agents for epoxy resins and the like.

However, the present above reaction scheme suffers from several drawbacks including relatively poor yields, and relatively poor control of regiochemistry. Moreover, because the above compounds are liquids, purification sometimes proves to be difficult. Further, the compounds of Sato '339 have stability issues. Thus, it would be desirable to be able to generate compounds that are similar to the above compounds that can be used effectively as starting materials for silicone-containing polyester resins, polyamide resins and addition type polyimide resins, silane coupling agents, and coupling agents for polyimide resins, as well as for plasticizers for vinyl chloride resins and similar compounds, and for curing agents for epoxy resins that do not suffer from the same drawbacks as the compounds as disclosed in Sato '339.

BRIEF SUMMARY OF THE INVENTION

The present invention relates to compounds, intermediates, compositions, and methods of making compounds and intermediates related to the compounds of Formula I and/or Formula II and/or Formula III and/or Formula IV and/or Formula VI and/or Formula VII:

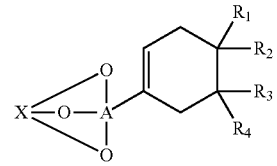

Formula I

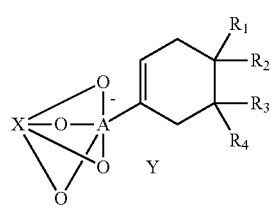

Formula II

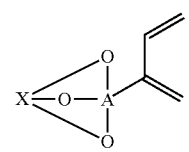

Formula III

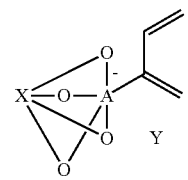

Formula IV

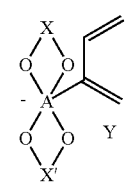

Formula VI

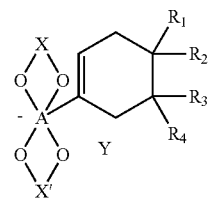

Formula VII wherein A is a member selected from the group consisting of silicon, platinum, rhodium, boron, arsenic and palladium;

X and X' are independently an aliphatic hydrocarbon chain or aromatic group which may be selected from one or more of the following alkyl, alkenyl, alkynyl, aryl, heteroaryl, heterocyclyl, wherein all of the alkyl, alkenyl, alkynyl, aryl, heteroaryl, heterocyclyl groups may contain one or more heteroatoms selected from the group consisting of nitrogen, phosphorous, arsenic, antimony, bismuth, germanium, tin, oxygen, sulfur, selenium, tellurium, boron, aluminum, gallium, indium, germanium, and silicon, and wherein all of the alkyl, alkenyl, alkynyl, aryl, heteroaryl, heterocyclyl groups also may be optionally substituted by one or more of the following, alkyl, alkenyl, alkynyl, aryl, heteroaryl, heterocyclyl, halo, cyano, oxo, hydroxy, mercapto, sulfonyl, sulfoxy, amino, imino, alkylthio, alkoxy, alkoxyalkyl, mono-alkylamino, di-alkylamino, nitro, nitroso, and thioxo. All of these substituents may, in turn, be optionally substituted with one or more substituents independently selected from the group consisting of halogen, hydroxy, cyano, carboxy, thiol, sulfo, nitro, nitroso, oxo, thioxo, and imino.

$R_1, R_2, R_3,$ and $R_4$ are each independently selected from the group consisting of hydrogen, alkyl, alkenyl, alkynyl, aryl, heteroaryl, heterocyclyl, halo, cyano, oxo, hydroxy, mercapto, sulfonyl, sulfoxy, amino, imino, alkylthio, alkoxy, alkoxyalkyl, mono-alkylamino, di-alkylamino, nitro, nitroso, and thioxo or $R_1$ and $R_2$ together with the atoms connected to them or $R_3$ and $R_4$ together with the atoms connected to them may form a spiro $C_{4-8}$ cycloalkyl group that may optionally contain one or more heteroatoms selected from the group consisting of nitrogen, phosphorous, arsenic, antimony, bismuth, germanium, tin, oxygen, sulfur, selenium, tellurium, boron, aluminum, gallium, indium, germanium, and silicon; or $R_1$ and $R_3$ together with the atoms connected to them or $R_2$ and $R_4$ together with the atoms connected to them may form a $C_{3-10}$ cycloalkyl group that may optionally contain one or more heteroatoms selected from the group consisting of nitrogen, phosphorous, arsenic, antimony, bismuth, germanium, tin, oxygen, sulfur, selenium, tellurium, boron, aluminum, gallium, indium, germanium, and silicon.

Y is a counterion such as an alkali metal or other positively charged ion.

BRIEF DESCRIPTION OF THE SEVERAL VIEWS OF THE DRAWINGS

FIGS. 1A and 1B are S-trans and S-cis depictions, respectively of the silatrane compound [(buta-1,3-dien-2-yl}silatrane] of the present invention as drawn from x-ray crystallography data.

FIGS. 2A and 2B are drawings of the catechol derived silicon compound {i.e., potassium [bis(1,2-benzenediolato)-1,3-butadien-2-yl-]silicate} of the present invention as drawn from x-ray crystallography data. FIG. 2A contains two THF molecules and potassium whereas FIG. 2B has neither present.

DETAILED DESCRIPTION OF THE INVENTION

The present invention generally relates to compounds, intermediates, compositions, and methods of making compounds and intermediates related to the compounds of Formula I and/or Formula II and/or Formula VII:

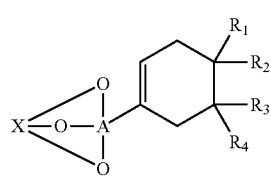

Formula I

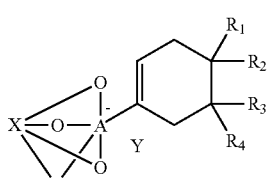

Formula II

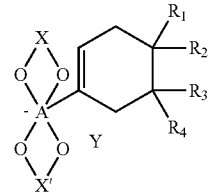

Formula VII wherein the substituents are defined below. In an embodiment, Formula I, Formula II, and Formula VII are generated from the dienes shown in Formula III, Formula IV, and Formula VI,

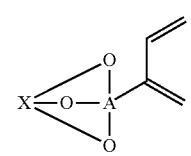

Formula III

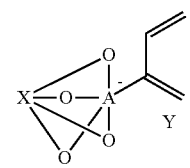

Formula IV

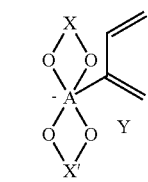

Formula VI respectively. Formula III, Formula IV, and Formula VI react with the dienophile shown in Formula V to generate the compounds as shown in Formulas I and II.

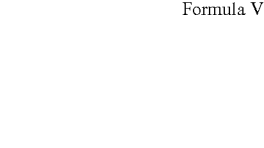

Formula V

Alternatively any of the dienes of Figures III, IV, or VI can react with the alkyne of figure VIII

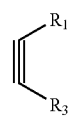

Formula VIII in a Diels-Alder fashion to produce the corresponding alkenylene compounds;

wherein in the above Formulas I, II, III, IV, V, VI, VII and VIII;

A is a member selected from the group consisting of silicon, platinum, rhodium, boron, arsenic and palladium;

X and X' are independently an aliphatic hydrocarbon chain or aromatic group which may be selected from one or more of the following alkyl, alkenyl, alkynyl, aryl, heteroaryl, heterocyclyl, wherein all of the alkyl, alkenyl, alkynyl, aryl, heteroaryl, heterocyclyl groups may contain one or more heteroatoms selected from the group consisting of nitrogen, phosphorous, arsenic, antimony, bismuth, germanium, tin, oxygen, sulfur, selenium, tellurium, boron, aluminum, gallium, indium, germanium, and silicon, and wherein all of the alkyl, alkenyl, alkynyl, aryl, heteroaryl, heterocyclyl groups also may be optionally substituted by one or more of the following, alkyl, alkenyl, alkynyl, aryl, heteroaryl, heterocyclyl, halo, cyano, oxo, hydroxy, mercapto, sulfonyl, sulfoxy, amino, imino, alkylthio, alkoxy, alkoxyalkyl, mono-alkylamino, di-alkylamino, nitro, nitroso, and thioxo. All of these substituents may, in turn, be optionally substituted with one or more substituents independently selected from the group consisting of halogen, hydroxy, cyano, carboxy, thiol, sulfo, nitro, nitroso, oxo, thioxo, and imino.

$R_1$, $R_2$, $R_3$, and $R_4$ are each independently selected from the group consisting of hydrogen, alkyl, alkenyl, alkynyl, aryl, heteroaryl, heterocyclyl, halo, cyano, oxo, hydroxy, mercapto, sulfonyl, sulfoxy, amino, imino, alkylthio, alkoxy, alkoxyalkyl, mono-alkylamino, di-alkylamino, nitro, nitroso, and thioxo or $R_1$ and $R_2$ together with the atoms connected to them or $R_3$ and $R_4$ together with the atoms connected to them may form a spiro $C_{4-8}$ cycloalkyl group that may optionally contain one or more heteroatoms selected from the group consisting of nitrogen, phosphorous, arsenic, antimony, bismuth, germanium, tin, oxygen, sulfur, selenium, tellurium, boron, aluminum, gallium, indium, germanium, and silicon; or $R_1$ and $R_3$ together with the atoms connected to them or $R_2$ and $R_4$ together with the atoms connected to them may form a $C_{3-10}$ cycloalkyl group that may optionally contain one or more heteroatoms selected from the group consisting of nitrogen, phosphorous, arsenic, antimony, bismuth, germanium, tin, oxygen, sulfur, selenium, tellurium, boron, aluminum, gallium, indium, germanium, and silicon.

Y is a counterion such as an alkali metal. In an embodiment, Y is potassium, sodium, tetrabutyl ammonium or other appropriate counterion.

It should be recognized that although the dienophile compounds of Formula V are shown as an alkene, alkynyl dienophile compounds are also contemplated and therefore within the scope of the invention (wherein either one of $R_1$ and $R_2$ is present on one side of the carbon carbon triple bond and either one of $R_3$ and $R_4$ is present on the other side). The product that is generated is similar to the compounds shown in Formulas I and II but would be amended to be a cyclohexyl 1,4-dienyl compound (that is, to have either of $R_1$ and $R_2$ present on one side of the carbon carbon double bond and either one of $R_3$ and $R_4$ is present on the other side).

Moreover, the compounds of Formulas I, II, III, IV, VI, and VII can also be used for polymerization reactions such as those that are present in Takenaka et al., Macromolecules, (1989), 22, pp. 1563-1567.

In an embodiment, the present invention is also directed to the synthesis of the above compounds as represented by Formulas I, II, and VII above, using the starting materials shown in Scheme-60, which generates intermediate 64.

Scheme - 60: Synthesis of 2-triethoxysilyl-1,3-butadiene using Grignard addition reaction

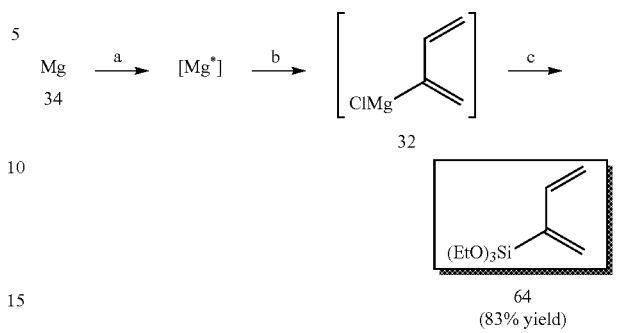

Reagents and conditions:
a i. dibromoethane in THF, r.t. ii. ZnCl$_2$ in THF, Δ, 15 min
b i. chloroprene (33) and dibromoethane in THF, dropwise with gentle Δ; ii. Δ for 45 min
c i. (EtO)$_3$SiCl (65) in THF, r.t; ii. canula transfer of 32 at r.t; iii. Δ for 1 h; iv. work-up Compound 32 can be used to make the corresponding dimethyl phenyl silane diene 32a.

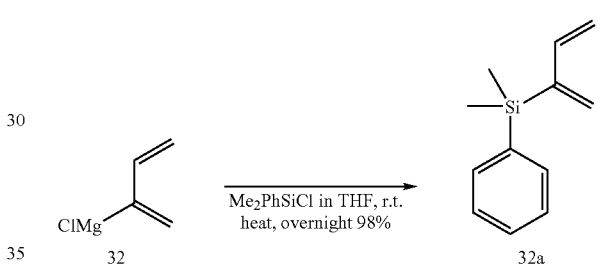

Intermediate 64 can be used to generate a plurality of possible compounds. For example, compound 67 can be made using the below scheme-61.

Scheme - 61: Synthesis of [buta-1,3-dien-2-yl]silatrane

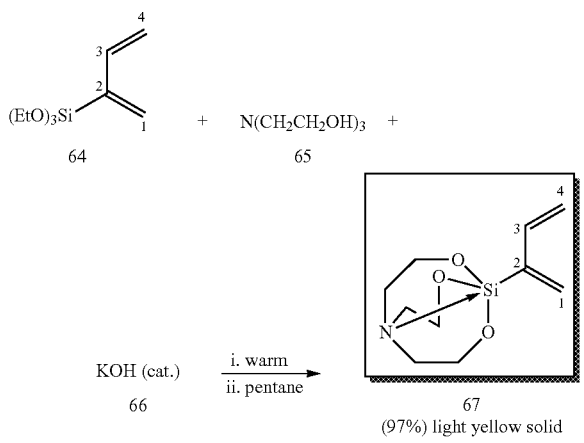

It should be recognized that any of a plurality of compounds can be used instead of compound 65. For example, the nitrogen in compound 65 can be replaced by phosphorous or arsenic. Moreover, the lengths of the alkyl chains in compound 65 can be varied to give any of a plurality of compounds. These compounds can then be reacted with a dienophile to generate the compounds shown in Formula II above. The above scheme 61 shows an example of the compounds that can be generated from Formula II.

Moreover, intermediate 64 can be reacted with a 1,2-dihydroxy benzene or other similar compounds to give phenyl containing compounds. An example of such a scheme is shown as scheme-62 to generate the bis-phenyl silicon containing diene 69.

Similar to Scheme 61, it should be recognized that any of a plurality of compounds

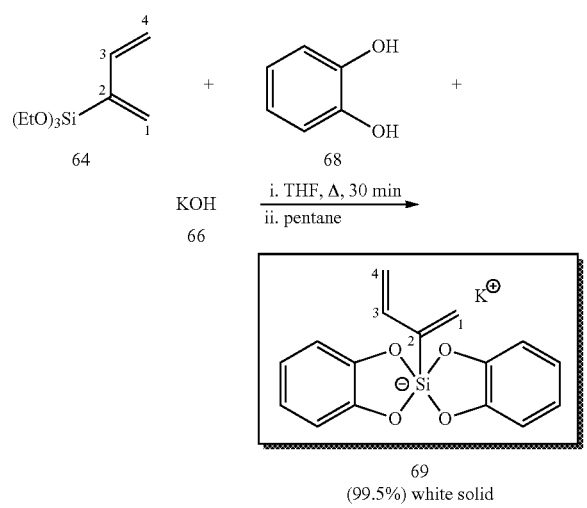

Scheme - 62: Synthesis of potassium[bis(1,2-benzenediolato)-1,3-butadien-2-yl-]silicate can be used instead of compound 68. For example, an alkyl chain may be present between the hydroxyl groups and the benzene ring. This will allow compounds to be generated from the 1,2-disubstituted benzenes, 1,3-disubstituted benzenes, and 1,4-disubstituted benzenes. The diene shown as compound 69 can then be reacted with a dienophile to generate compounds such as those shown above in Formula II. This general reaction scheme is shown below in scheme 170

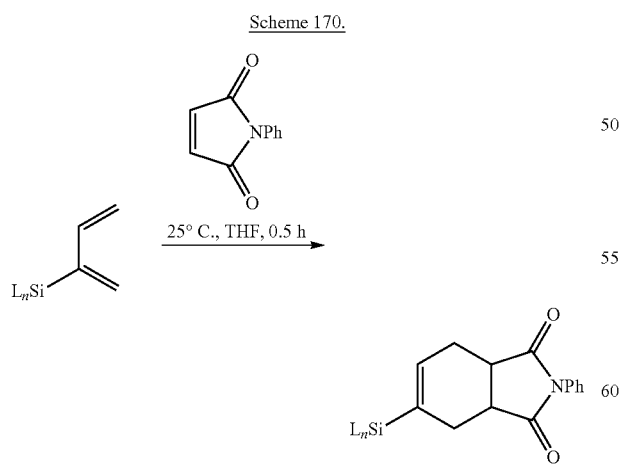

Scheme 170.

In this scheme, Ln represents ligands such as the catechol silicon derivative as shown in compound 69 in scheme-62 or the silatrane functionality of compound 67 in scheme-61.

Although the dienophile is shown as 1-phenyl-1H-pyrrole-2,5-dione, it should be recognized that any dienophile is contemplated and therefore within the scope of the present invention. Further, the silicon in the above reaction can be substituted by any of the atoms that are listed as A in Formulas I and II above. An exemplary embodiment of the catechol silicon derivative (Potassium bis(1,2-benzenediolato)-(1,3-butadien-2-yl)silicate) reaction with 1-phenyl-1H-pyrrole-2,5-dione is shown in below scheme 171:

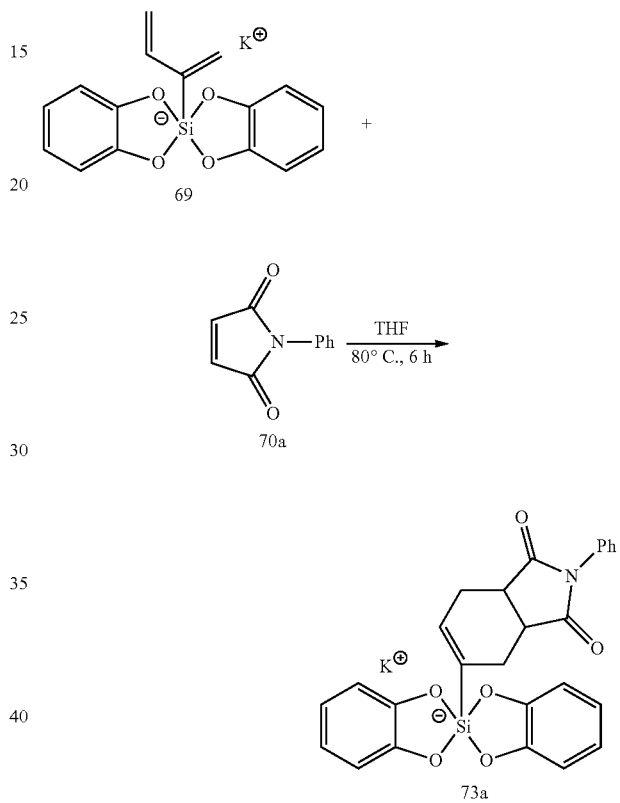

Scheme 171.

Scheme 172 shows another exemplary embodiment of the catechol silicon derivative reaction with a different dienophile (i.e, 3-methylfuran-2,5-dione).

Scheme 172.

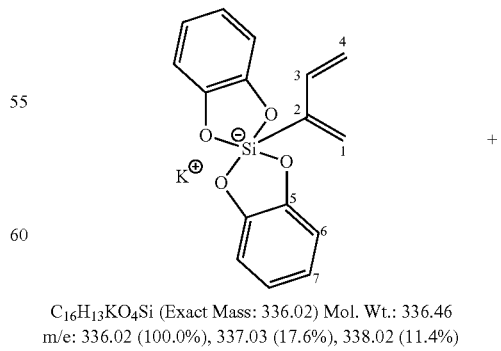

$C_{16}H_{13}KO_4Si$ (Exact Mass: 336.02) Mol. Wt.: 336.46
m/e: 336.02 (100.0%), 337.03 (17.6%), 338.02 (11.4%)
337.02 (5.1%), 338.03 (2.3%), 339.02 (2.2%)
C, 57.12; H, 3.89; K, 11.62; O, 19.02; Si, 8.35

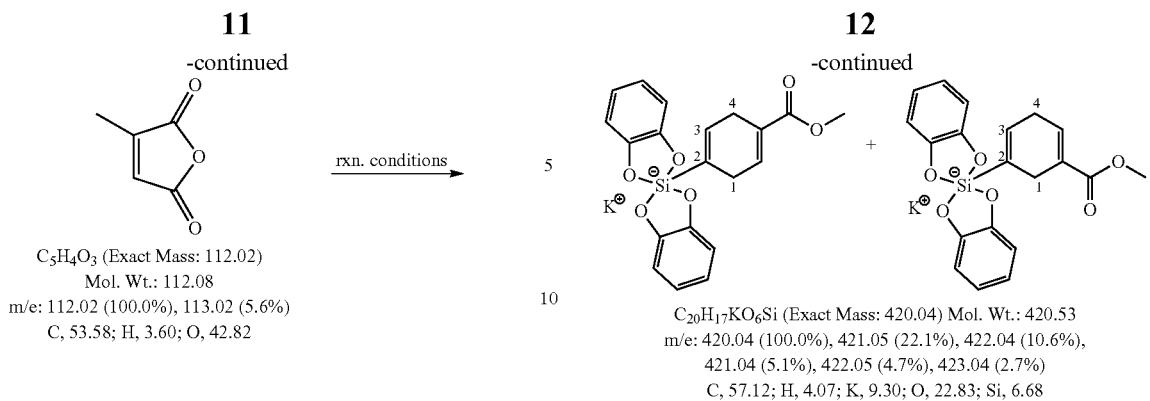

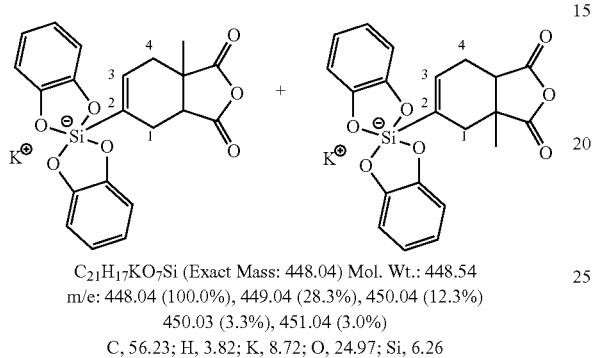

C₂₁H₁₇KO₇Si (Exact Mass: 448.04) Mol. Wt.: 448.54
m/e: 448.04 (100.0%), 449.04 (28.3%), 450.04 (12.3%)
450.03 (3.3%), 451.04 (3.0%)
C, 56.23; H, 3.82; K, 8.72; O, 24.97; Si, 6.26

Scheme 173 shows another exemplary embodiment of the catechol silicon derivative reaction with a different dienophile (i.e, methyl propiolate).

Scheme 173.

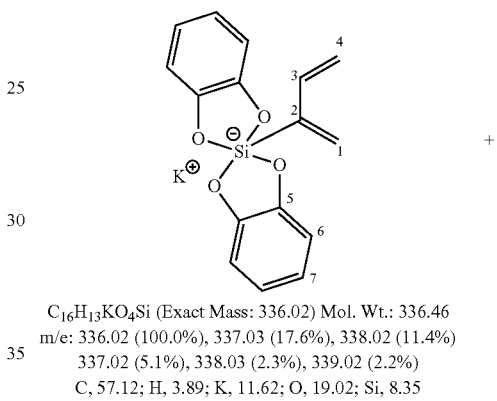

C₁₆H₁₃KO₄Si (Exact Mass: 336.02) Mol. Wt.: 336.46
m/e: 336.02 (100.0%), 337.03 (17.6%), 338.02 (11.4%)
337.02 (5.1%), 338.03 (2.3%), 339.02 (2.2%)
C, 57.12; H, 3.89; K, 11.62; O, 19.02; Si, 8.35

C₄H₄O₂ (Exact Mass: 84.02) Mol. Wt.: 84.07
m/e: 84.02 (100.0%), 85.02 (4.3%)
C, 57.14; H, 4.80; O, 38.06

C₂₀H₁₇KO₆Si (Exact Mass: 420.04) Mol. Wt.: 420.53
m/e: 420.04 (100.0%), 421.05 (22.1%), 422.04 (10.6%),
421.04 (5.1%), 422.05 (4.7%), 423.04 (2.7%)
C, 57.12; H, 4.07; K, 9.30; O, 22.83; Si, 6.68

Scheme 174 shows another exemplary embodiment of the catechol silicon derivative reaction with a different dienophile (i.e, methyl 2-methylacrylate).

Scheme 174.

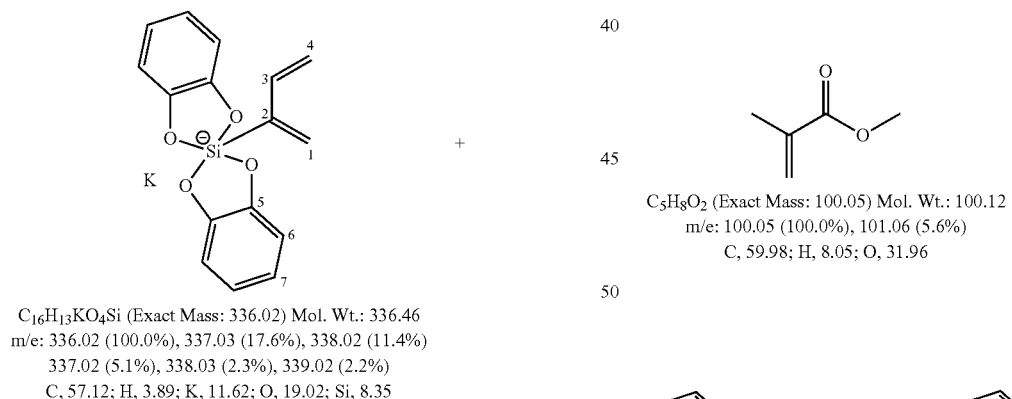

C₁₆H₁₃KO₄Si (Exact Mass: 336.02) Mol. Wt.: 336.46
m/e: 336.02 (100.0%), 337.03 (17.6%), 338.02 (11.4%)
337.02 (5.1%), 338.03 (2.3%), 339.02 (2.2%)
C, 57.12; H, 3.89; K, 11.62; O, 19.02; Si, 8.35

C₅H₈O₂ (Exact Mass: 100.05) Mol. Wt.: 100.12
m/e: 100.05 (100.0%), 101.06 (5.6%)
C, 59.98; H, 8.05; O, 31.96

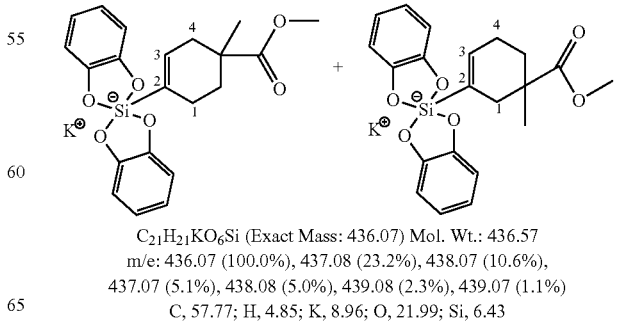

C₂₁H₂₁KO₆Si (Exact Mass: 436.07) Mol. Wt.: 436.57
m/e: 436.07 (100.0%), 437.08 (23.2%), 438.07 (10.6%),
437.07 (5.1%), 438.08 (5.0%), 439.08 (2.3%), 439.07 (1.1%)
C, 57.77; H, 4.85; K, 8.96; O, 21.99; Si, 6.43

Scheme 175 shows another exemplary embodiment of the catechol silicon derivative reaction with a different dienophile (i.e, 1-phenyl-3,5-dimethyl-1H-pyrrole-2,5-dione):

Other dienophiles that can be used with the catechol silicon derivative in a Diels Alder reaction include Schemes 176-177:

Scheme 175.

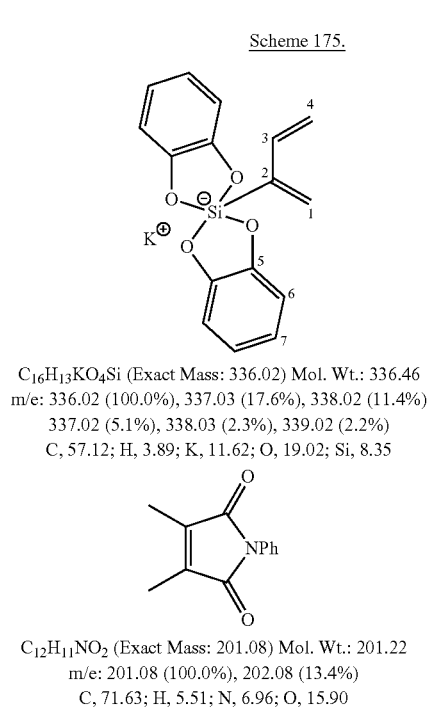

$C_{16}H_{13}KO_4Si$ (Exact Mass: 336.02) Mol. Wt.: 336.46
m/e: 336.02 (100.0%), 337.03 (17.6%), 338.02 (11.4%)
337.02 (5.1%), 338.03 (2.3%), 339.02 (2.2%)
C, 57.12; H, 3.89; K, 11.62; O, 19.02; Si, 8.35

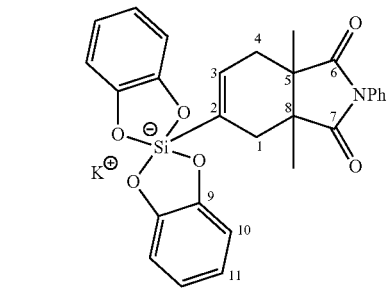

$C_{12}H_{11}NO_2$ (Exact Mass: 201.08) Mol. Wt.: 201.22
m/e: 201.08 (100.0%), 202.08 (13.4%)
C, 71.63; H, 5.51; N, 6.96; O, 15.90 rxn. conditions →

Scheme 176.

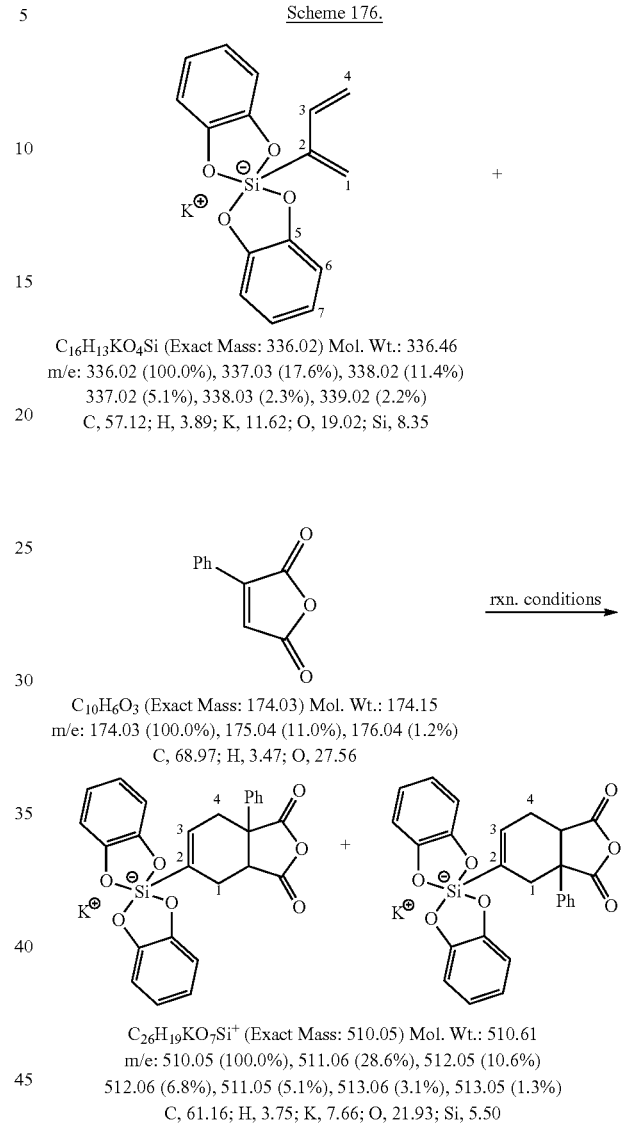

$C_{16}H_{13}KO_4Si$ (Exact Mass: 336.02) Mol. Wt.: 336.46
m/e: 336.02 (100.0%), 337.03 (17.6%), 338.02 (11.4%)
337.02 (5.1%), 338.03 (2.3%), 339.02 (2.2%)
C, 57.12; H, 3.89; K, 11.62; O, 19.02; Si, 8.35

$C_{10}H_6O_3$ (Exact Mass: 174.03) Mol. Wt.: 174.15
m/e: 174.03 (100.0%), 175.04 (11.0%), 176.04 (1.2%)
C, 68.97; H, 3.47; O, 27.56 rxn. conditions →

$C_{28}H_{24}KNO_6Si$ (Exact Mass: 537.1) Mol. Wt.: 537.68
m/e: 537.10 (100.0%), 538.10 (35.7%), 539.10 (12.3%),
539.11 (5.8%), 540.10 (3.7%), 540.11 (1.1%)
C, 62.55; H, 4.50; K, 7.27; N, 2.61; O, 17.85; Si, 5.22

$C_{26}H_{19}KO_7Si^+$ (Exact Mass: 510.05) Mol. Wt.: 510.61
m/e: 510.05 (100.0%), 511.06 (28.6%), 512.05 (10.6%)
512.06 (6.8%), 511.05 (5.1%), 513.06 (3.1%), 513.05 (1.3%)
C, 61.16; H, 3.75; K, 7.66; O, 21.93; Si, 5.50

Scheme 177.

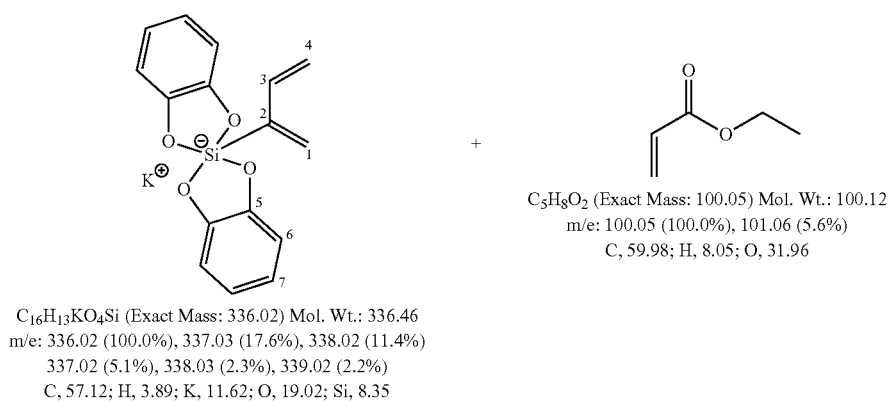

$C_{16}H_{13}KO_4Si$ (Exact Mass: 336.02) Mol. Wt.: 336.46
m/e: 336.02 (100.0%), 337.03 (17.6%), 338.02 (11.4%)
337.02 (5.1%), 338.03 (2.3%), 339.02 (2.2%)
C, 57.12; H, 3.89; K, 11.62; O, 19.02; Si, 8.35

$C_5H_8O_2$ (Exact Mass: 100.05) Mol. Wt.: 100.12
m/e: 100.05 (100.0%), 101.06 (5.6%)
C, 59.98; H, 8.05; O, 31.96 rxn. conditions →

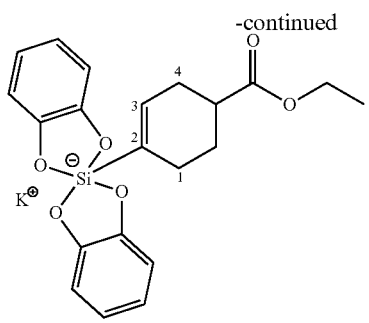
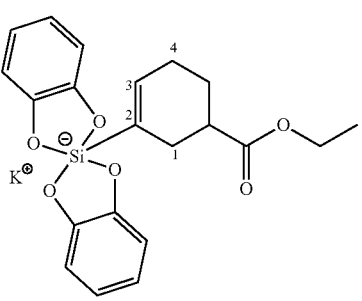

$C_{21}H_{21}KO_6Si$ (Exact Mass: 436.07) Mol. Wt.: 436.57
m/e: 436.07 (100.0%), 437.08 (23.2%), 438.07 (10.6%), 437.07 (5.1%)
438.08 (5.0%), 439.08 (2.3%), 439.07 (1.1%)
C, 57.77; H, 4.85; K, 8.96; O, 21.99; Si, 6.43

One other dienophile that is contemplated is compound 10f

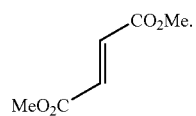

10f

When compound 67 or 69 undergo a Diels Alder type reaction with compound 8 (3-methylfuran-2,5-dione)

67

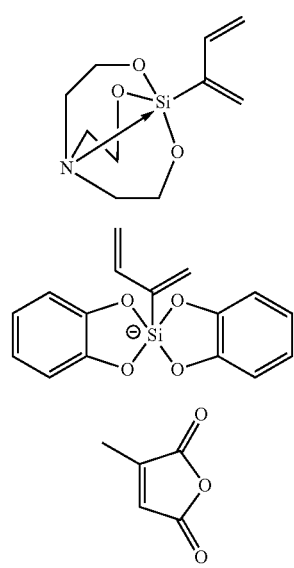

69

8

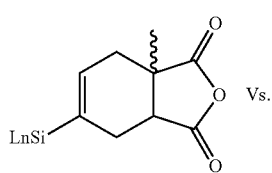

the regiochemistry of the product shows good selectivity. The general products are shown as compounds 9 and 10

9

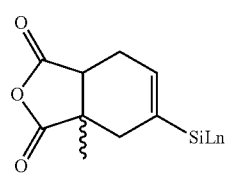

10 wherein Ln represents the ligands attached to the Si atoms as shown in 67 and 69. The silatrane substituted diene (67) produced a 3.4:1 mixture of para, meta regioisomers (9:10) in 78% isolated yield after heating to 120° C. in THF for 48 h. The catechol silane substituted diene (69) reacted under slightly milder conditions (80° C. for 36 h) to produce a 6.4:1 mixture of 9:10 in 92% isolated yield.

In contrast to the very good yields shown for a cycloaddition reaction with the silicon compounds 67 (98% yield with compound 70a) and 69 (98% yield with compound 70a), when compound 64 is reacted with dienophile compound 70a the yield was found to be 2%.

64

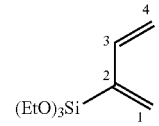

70a

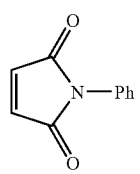

The compounds of Formula I, Formula II, Formula III, Formula IV, Formula VI and Formula VII:

Formula I

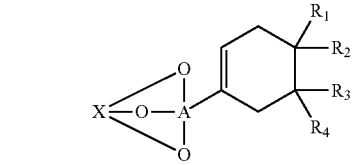

Formula II

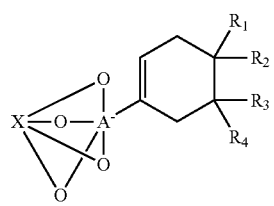

Formula III

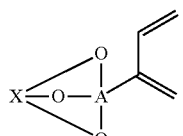

Formula IV

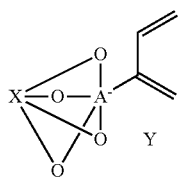

Formula VI

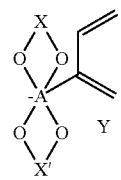

Formula VII

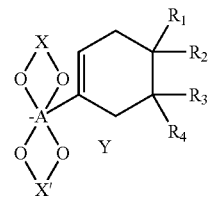

have as possibilities for A any of silicon, platinum, rhodium, boron, arsenic and palladium.

Any of the atoms that are possibilities for A can be present prior to undergoing the Diels Alder reaction. Alternatively, A can be silicon and an atom substitution reaction can be performed to substitute a different atom for A. In an embodiment, in Formula III, A is silicon and X is not present (that is, the Si atom has three hydroxyl groups attached to it).

For example, the following scheme 59c shows that one means of generating the various atoms that are A is by substitution in a trans-metalation type reaction. To substitute platinum or one of the above enumerated atoms for the silicon atom, one can employ a transmetalation reaction. In scheme 59c, one can see this transmetalation reaction and should note that this is a catalytic cycle.

Scheme - 59c: Proposed catalytic cycle for domino/tandem Diels-Alder and cross-coupling reactions

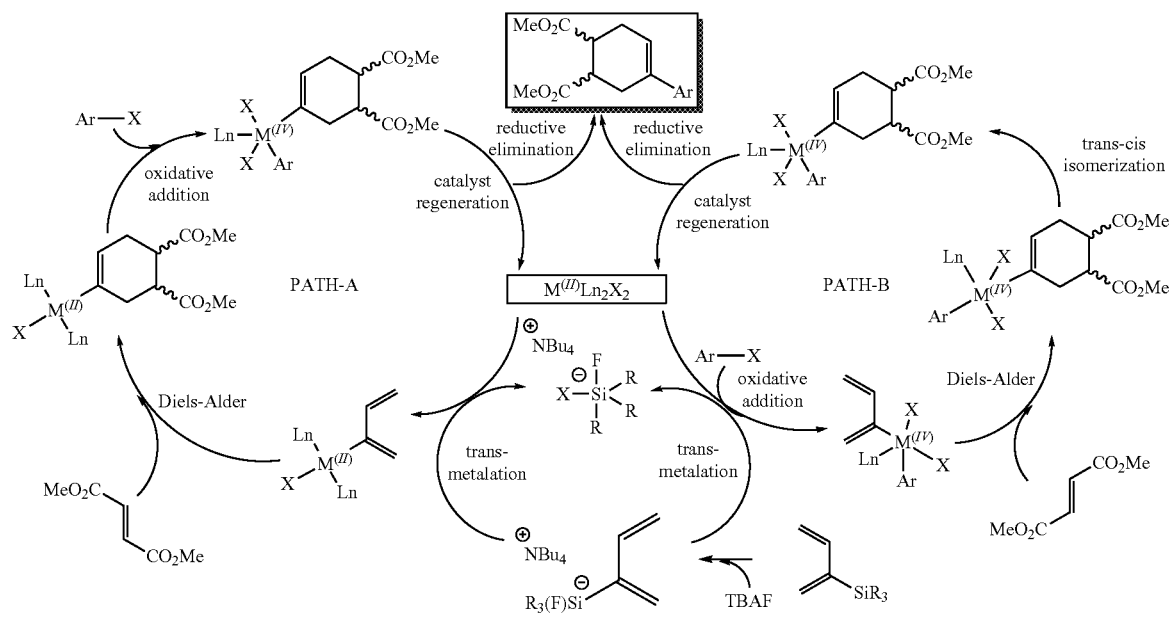

Fluoride source = CsF, TBAF etc.; R = Alkoxy, Alkyl, Aryl; M = $Pt^{(II)}$

Thus, it should be apparent that the silicon compound can be substituted with any of the above enumerated atoms for A. The advantages of this transmetalation process is that it allows enhanced regio and stereo selectivity and a one-pot methodology can be employed.

The stable Pt(II) catalysts can be prepared by treating PtCl$_2$(dmso)$_2$ with various ligands. A representative example for the synthesis of a Pt(II) catalyst is outlined in Scheme-59d.

Scheme - 59d: Synthetic plan for the synthesis of Pt(II) catalysts

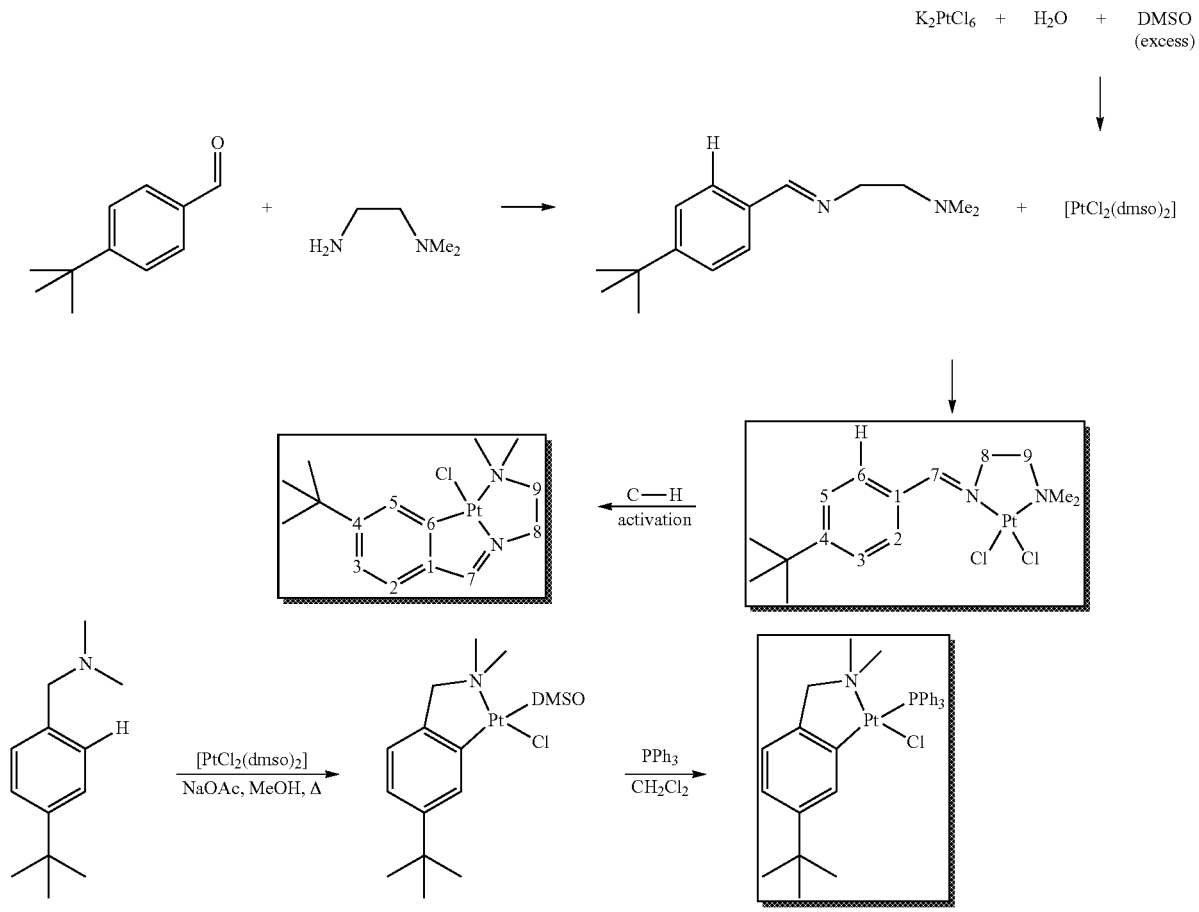

One means of generating terminal substituted silyl dienes is by a conversion from allenic acetates/allenic carboxylates. Alkoxysilyl dienes (80) can be prepared by allylic substitution of the allenic acetates (77c, d) allenic carboxylates (77e, f) using (aminosilyl)lithiums (81c) which can be prepared in two steps using the protocol shown in Scheme-68.

Scheme - 68: Proposed pathway for the synthesis of alkoxysilydienes (Tamao protocol)

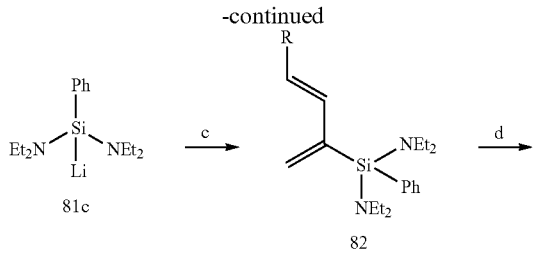

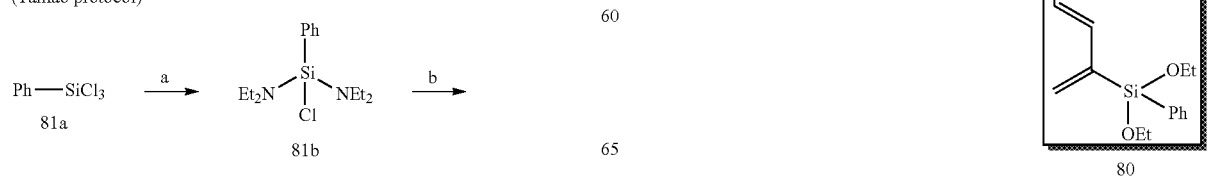

-continued

LG = OAc; R = cyclohexyl (77c)
= OAc; = phenyl (77d)
= CO₃Et; = phenyl (77e)
= CO₃Et; = cyclohexyl (77f)

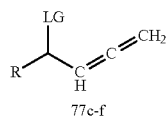

77c-f

Reaction conditions:
a Et₂NH, NEt₃, THF, 0° C., overnight;
b Li (granular), THF, 0° C., 4 h
c 77c-f in THF;
d EtOH, r.t, overnight Alternatively, terminal substituted silyl dienes can also be prepared from halodienes. Alkoxysilyl dienes (80) can also be prepared by a $S_N2'$ reaction of the silylanions (81c) with halodienes (77a, b). During this coupling reaction, selective reductive elimination of the vinyl groups in the presence of aryl and alkyl groups may occur. See Scheme-69.

Moreover, terminal substituted silyl dienes can also be prepared by the silylation of halodienes. Alkoxy silyl dienes (83) can be prepared by silylation of the halodienes (77a, b) with triethoxysilane in presence of catalytic Rh(I) or Pd(0). See Scheme-70.

Scheme - 70: Synthesis of trialkoxysilyldienes by hydrosilylation of halodienes

H—Si(OEt)₃ +

[structure]
77a/77b
X = Br, I
R = alkyl, aryl, cyclohexenyl

Rh(I) or Pd(0) →

[structure (EtO)₃Si 83]

Intramolecular enyne cross-metathesis reactions of triethoxysilylalkyne (84) with olefins (85) in the presence of second-generation Grubbs catalyst (86) results in the stereoselective synthesis of (E)-1,3-disubstituted silylbutadienes (83) in moderate yields. See Scheme-71.

Scheme - 71: Enyne cross-metathesis reaction for synthesis of trialkoxysilyldiene

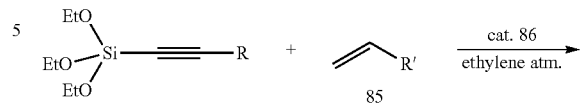

[structure 83 (EtO)₃Si]   [structure 86 (Grubb's catalyst)]

R, R' = H or any group

Triethoxysilyl diene (83) can be prepared from the cross-coupling reaction of halodienes (77a, b) with triethoxychlorosilane (65) in the presence of a catalytic amount of a transition metal, Pd(II) or Ni(II). See Scheme-72.

Scheme - 72: Synthesis of trialkoxysilyldiene by Kumada reaction

Mg →ᵃ [Mg*] →ᵇ

[Cl—Mg—Si(OEt)₃] →ᶜ,ᵈ

[structure 83 (EtO)₃Si]

Reaction conditions:
a i. I₂ in THF, r.t; ii. dibromoethane in THF, r.t; iii. r.t → 0° C.
b i. catalytic Ni(II); ii. (EtO)₃SiCl (65) in THF
c 77a/77b in THF, dropwise, 30 min
d 0° C. → r.t, overnight It is contemplated that Rhodium-catalyzed asymmetric 1,4-addition of organosilanes will work as shown below. Highly enantioselective asymmetric 1,4-addition reactions of trialkoxyorganosilanes with α,β-unsaturated carbonyl compounds (ketones, esters and amides) using catalytic chiral rhodium complexes are likely to work as shown in Scheme-73.

Scheme 73: - Rhodium-catalyzed asymmetric 1,4-addition of organosilanes

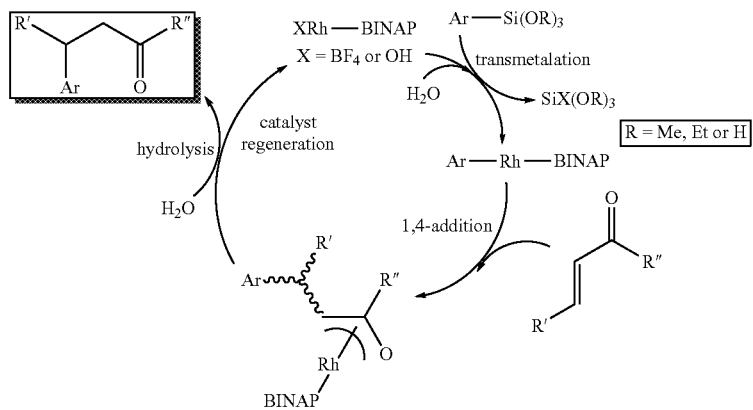

Moreover, using similar methodologies as disclosed above, it is proposed that the asymmetric catalysis reactions will work with the silyl dienes disclosed in this application. A proposed mechanism is as shown in Scheme-74.

Scheme-75 below shows a method for the synthesis of 2-halo-1-substituted dienes.

Scheme - 74: Proposed catalytic asymmetric Diels-Alder and 1,4-addition reaction mechanism

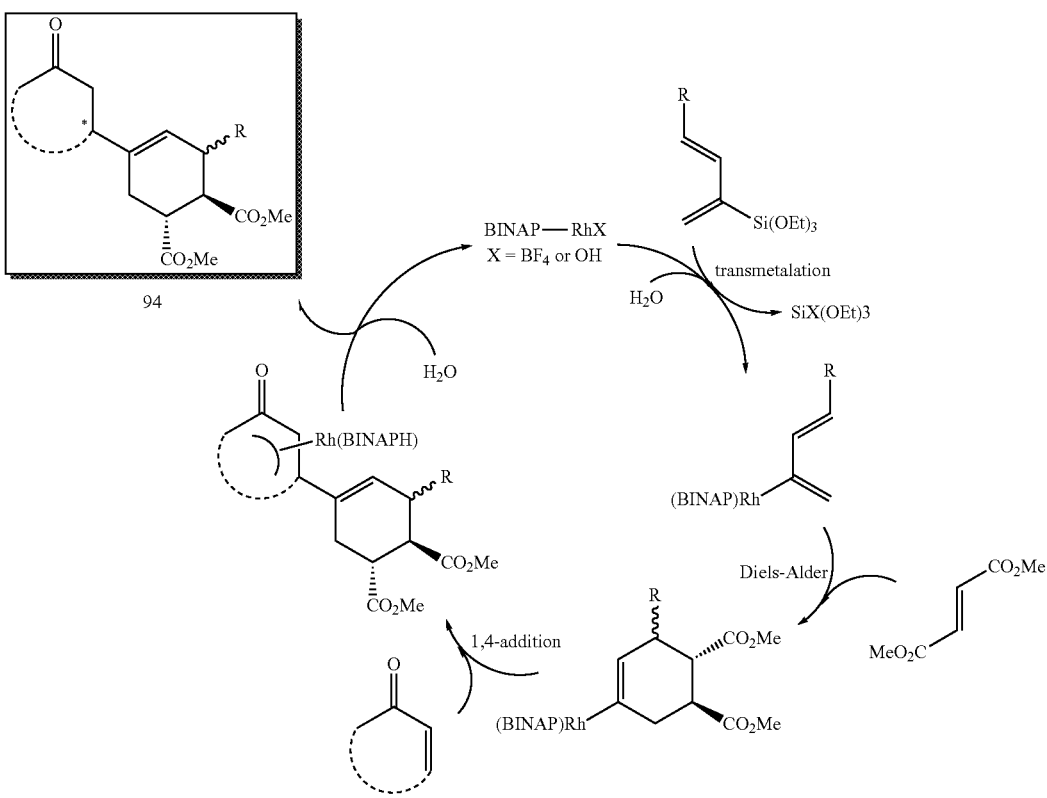

Scheme - 75: Proposed method for synthesis of 2-halo-1-substituted diene

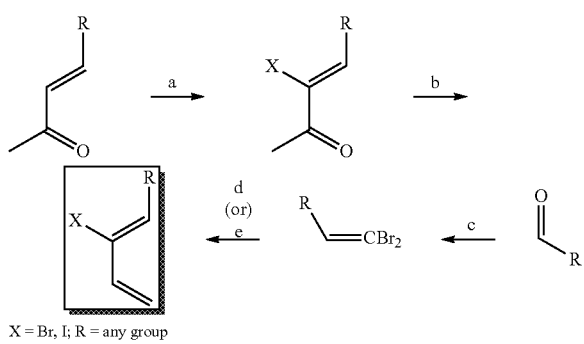

X = Br, I; R = any group

Reaction conditions:
a i. CCl$_4$, 0° C.; ii. Br$_2$ (or) Cl$_2$; iii. 0° C. → r.t, Et$_3$N;
b i. THF, Wittig's salt, 0° C.; ii. $^n$BuLi in hexane
c i.CH$_2$Cl$_2$, 0° C; ii. PPh$_3$; iii. 0° C. → r.t, 1 h;
d cat. Pd(dba)$_3$, TPP, tributyl(vinyl)tin, 100° C, 20h
e cat. Pd(PPh$_3$)$_4$, 0° C., vinylzinc chloride, 1 h, r.t A means of synthesizing oxasilacyclodienes and their exo-selective Diels-Alder and cross-coupling reactions is shown below. The methodology used to synthesize oxasilacyclodienes and their subsequent tandem Diels-Alder and cross-coupling reactions uses a catalytic pathway for exo-selective synthesis of substituted cyclohexenes (Scheme-59) or by following the pathway for catalytic asymmetric 1,4-addition reactions (Scheme-74). Dienes may be prepared using either transition-metal catalyzed hydrosilylation from respective enynols (as shown in Scheme-76) or by base-catalyzed tandem reaction using carbonyl compounds and alkynylsilanes (as shown in Scheme-77).

Scheme - 76: Proposed approach (Transition-Metal catalyzed) for the synthesis of oxasilacyclodienes

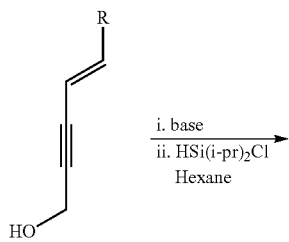

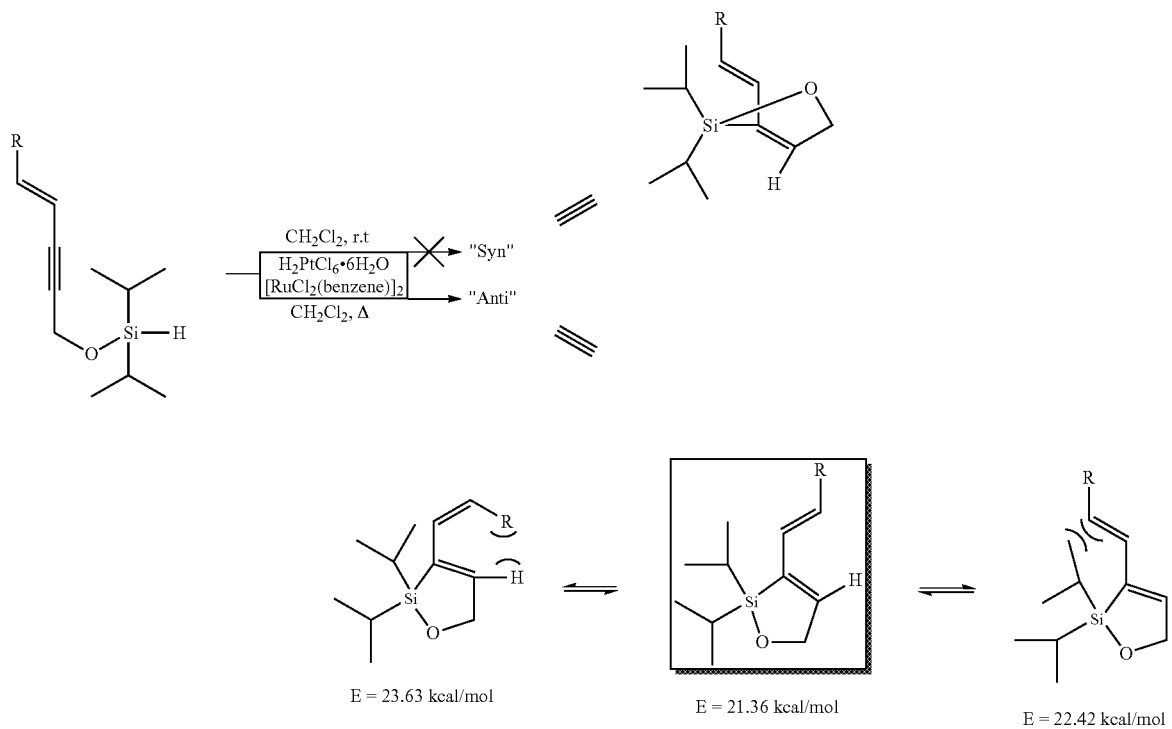

Scheme - 77: Proposed approach (base-catalyzed) for the synthesis of oxasilacyclodienes
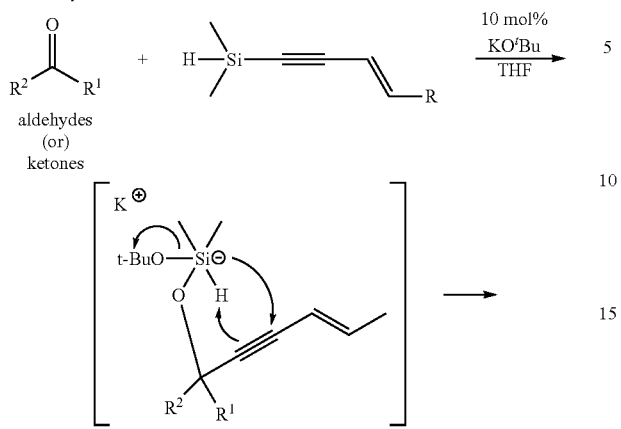
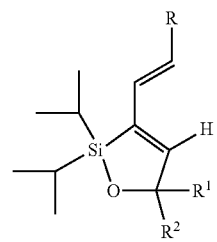
An embodiment of the present invention uses the dienes 20 and 23 in scheme 78 as starting materials to undergo the Diels Alder reaction with the dienophile compounds of Formula V. Scheme 78 shows how diene compounds 20 and 23 can be synthesized.
Scheme 78.
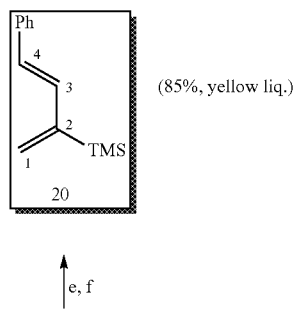
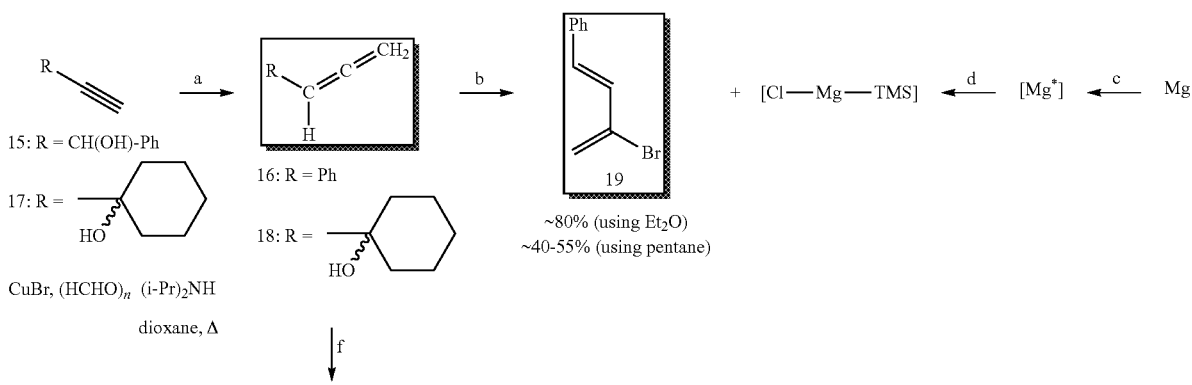
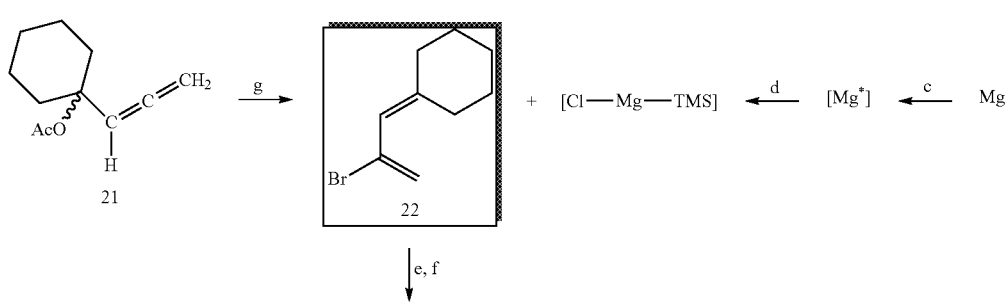

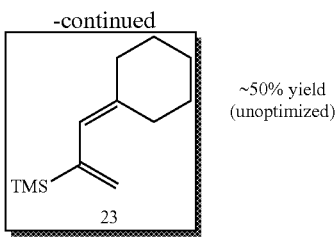

~50% yield (unoptimized)

Reaction conditions:
a CuBr, (HCHO)$_m$ (i-pr)$_2$NH, dioxane, Δ, overnight;
b CH$_3$COOH, 50° C., 40 min;
c i. I$_2$ in THF, r.t; ii. dibromoethane in THF, r.t; iii. r.t → 0° C.;
d TMSCl;
e 19/22 in THF, dropwise, 30 min;
e 0° C. → r.t, overnight;
f acetic anhydride, pyridine, DMAP, 40° C., overnight;
g 1.5 mol% Pd(OAc)$_2$, LiBr, CH$_3$COOH, 40° C., overnight.

1). Ma et al., *Synthesis*, 2002, 12, 1643-45; 2.) Hoyath, A., Backvall, J. E., *J. Org. Chem.* 2001, 66(24), 8120-26. 3.) Ma et al., *Tet. Lett.* 2002, 43(33), 5723-26; 4.) Dudley et al., *J. Org. Chem.* 2005, 71(1), 420-22.

Another embodiment of the present invention are compounds that are similar to 26a

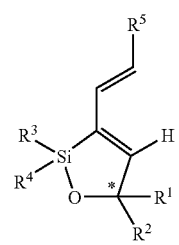

which can be made by a synthetic scheme as shown in scheme 79.

Scheme 79.

R$^1$: (Me)C=CH$_2$; R$^2$, R$^3$: H
R$^1$: 1-Cyclohexenyl; R$^2$, R$^3$: H
R$^1$: 1-Cyclohexenyl; R$^2$: Ph; R$^3$: H
R$^1$: 1-Cyclohexenyl; R$^2$, R$^3$: Me
R$^1$: HC=C(Me)H; R$^2$, R$^3$: H

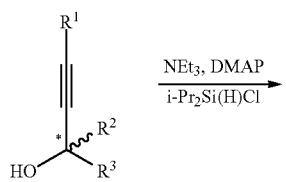

24a
24b
24c
24d
24e

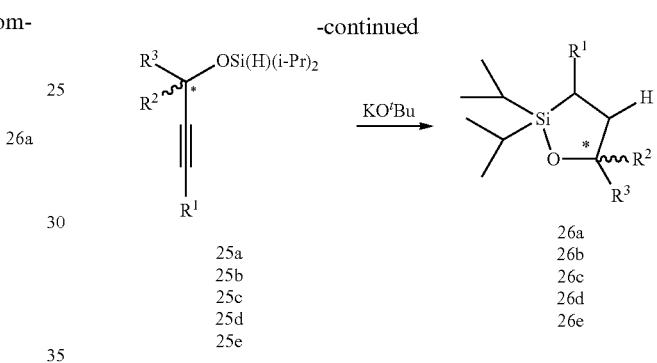

25a    26a
25b    26b
25c    26c
25d    26d
25e    26e

The diene that is generated in the above scheme can be reacted with a dienophile. For example compound 26a will undergo reaction with a dienophile in a Diels Alder type fashion to generate compounds such as compound 27a. It should be recognized that any of the above compounds or compounds similar to those from Scheme 79 will undergo this Diels Alder type reaction to generate the corresponding product. See scheme 80 for an example.

Scheme 80.

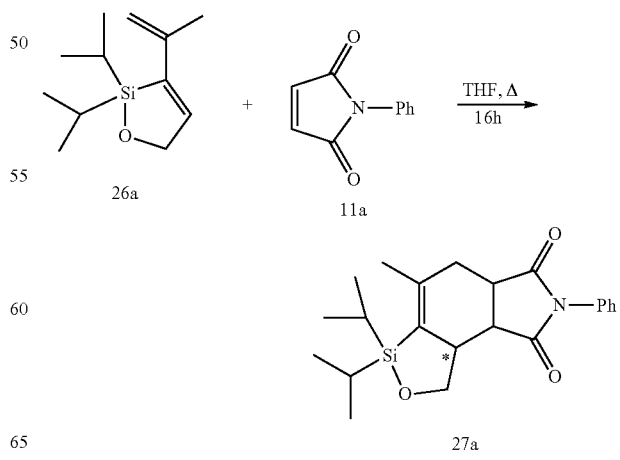

Although all of the above reactions are shown with a separate self contained dienophile, it should be recognized that intramolecular reactions are contemplated and therefore within the scope of the present invention. For example, a compound such as 31 might be employed to undergo a Diels Alder type intramolecular reaction.

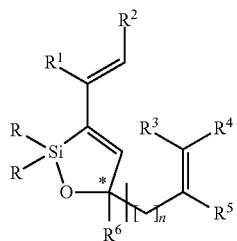

31

This is a possible route to generating polycyclic compounds that may end up being useful for one or more of the purposes discussed elsewhere in this written description.

The compounds of Formulas I, II, and VII may also prove to be useful starting materials to generate other compounds. For example, the A containing substituent from the cyclohexene ring in the compounds of Formulas I and II

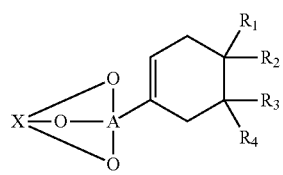

Formula I

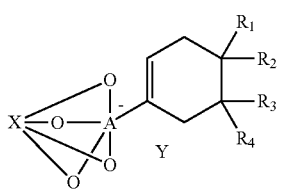

Formula II can be replaced by a group that has carbon attached to the cyclohexene ring. For example, when compound 101 is reacted with dienophile 1 (containing an electron withdrawing group), and then subsequently reacted with an alkyl halide, the silicon containing substitutent is removed. See scheme 81.

Scheme 81.

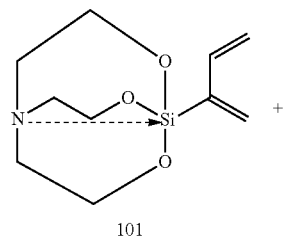

101

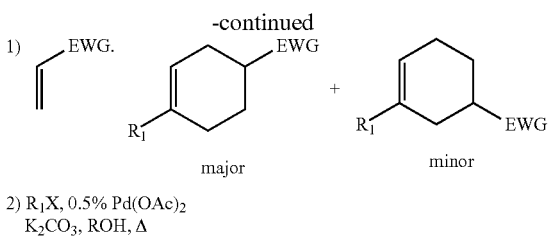

2) $R_1X$, 0.5% $Pd(OAc)_2$
$K_2CO_3$, ROH, $\Delta$

Experimental

General Experimental Protocol

All $^1$H NMR spectra were recorded by using a Bruker Avance 500 MHz spectrometer and Bruker Avance 300 MHz spectrometer operating at 500.13 MHz and 300.13 MHz respectively. $^{13}$C NMR spectra were recorded on a Bruker Avance 300 MHz spectrometer and Bruker Avance 500 MHz spectrometer operating at 75.48 MHz and 125.77 MHz respectively. Chemical shifts were reported in parts per million ($\delta$) relative to tetramethylsilane (TMS) or chloroform (CDCl3). Coupling constants (J values) were reported in hertz (Hz), and spin multiplicities were indicated by the following symbols: s (singlet), d (doublet), t (triplet), q (quartet), p (pentet), s (sixtet), h (heptet) and m (multiplet).

All elemental analyses were carried out by Atlantic Microlabs Inc., GA. High resolution
mass spectrometric (HRMS) analyses were carried out at the Duke Mass Spectrometric Facility,
Durham, N.C. and Mass Spectrometry Center at UNC-Chapel Hill, N.C. Flash chromatography was performed using thick-walled glass chromatography columns and "Ultrapure" silica gel (Silicycle Ind., Canada, 40-63 µm). Vacuum filtrations were carried out with the aid of microanalysis vacuum filter apparatus and Millipore filter membranes.

All reactions were carried out under an inert atmosphere unless otherwise noted. Tetrahydrofuran, dimethylformamide and methylene chloride were purchased from Fischer Scientific in the form of solvent kegs and distilled by using the centrally located solvent dispensing system developed by J. C. Meyer. Hexanes were distilled over $CaH_2$ before use. Silyl reagents were either purchased from Sigma-Aldrich or Gelest Inc. Deuterated solvents were purchased from Cambridge Isotopes and used as received. All other chemicals were purchased from Sigma-Aldrich and used as received.

General Procedure for Syntheses of 2-Silyl Substituted (Conjugated) Dienes. 2-Silyl substituted-1,3-butadienes and terminally substituted 2-silyl-1,3-dienes can be prepared efficiently by nucleophilic addition of the concerned Grignard reagents either in hot reaction conditions (Method-A) or in cold reaction conditions (reverse addition) (Method-B) as described below.

Method-A. Silyl diene was prepared in an oven-dried 100 mL 2-neck round-bottom flask equipped with a magnetic stir bar, addition funnel and reflux condenser, which was charged with magnesium (1.6 eq) followed by the addition of dibromoethane (11.0 mol %) in THF (5 mL). After stirring ~ca. 5 min (initiation of magnesium activation can be noticed by its silver color and ethane gas liberation), 3.0 mol % of anhydrous $ZnCl_2$ in THF (5 mL) was added. This mixture was added with additional THF (30 mL) and resulted in a whitish-grey solution which was brought to gentle reflux over a period of 15 min. Chloroprene (in 50% xylenes) (1.0 eq) and dibromoethane (23.0 mol %) in THF (25 mL) was added drop-wise to the refluxing reaction mixture over 30 min. After the addition, refluxing was continued for another 45 min. The greenish-grey colored Grignard solution was transferred by canula into a 250 mL, one-neck round-bottomed flask containing triethoxychlorosilane (0.95 eq) in THF (25 mL) at room temperature. The reaction mixture was refluxed (1 h), poured into 0.5M HCl solution (100 mL) and extracted with pentane (2×75 mL). The combined colorless clear organic layers were washed successively with 0.5M HCl (75 mL) and water (2×100 mL). After drying over MgSO$_4$, the solvent was removed under reduced pressure to yield 2-substituted silyl diene with xylenes as a colorless liquid. This compound was subjected for fractional vacuum distillation to remove xylenes and then purified by flash chromatography. Method-B. Substituted silyl dienes were prepared according to an analogous procedure with slight modifications. Magnesium turnings (3.0 eq) and iodine (4.0 mol %) were taken into a 2-neck, 100 mL round-bottomed flask fitted reflux condenser, additional funnel and stir-bar. After adding THF (2.0 mL) and stirring for ca ~2 min, dibromoethane (15 mol %) in THF (5.0 mL) was added at room temperature. After cessation of ethane gas, the reaction flask was cooled to 0° C. using an ice-bath, and stirring continued for 10 min. to which silylchloride (1.3 eq) in THF (10 mL) was added dropwise over 15 min. followed by dropwise addition of a mixture of 1-[(E)-3-bromobuta-1,3-dienyl]benzene (1.0 eq) and dibromoethane (30 mol %) in THF (20 mL) over a period of 45 min. After the addition of a halodiene, stirring was continued for 1 h at 0° C. and, then at room temperature overnight. The reaction mixture was filtered through a pad of celite made with diethyl ether and then quenched with 0.6 M HCl (50 mL), extracted with diethyl ether (3×30 mL). Thr combined organic layers were washed with brine solution (2×50 mL), dried over MgSO$_4$ and volatiles were removed. The crude residue of the reaction mixture was purified by flash chromatography resulting in the silyl diene in almost quantitative yields.

General Procedure for Synthesis of Enynylsilane

Enynylsilanes were prepared according to a procedure similar to that reported by Maifeld et al. (Unusual Tandem Alkynylation and trans-Hydrosilylation To Form Oxasilacyclopentenes; Org. Lett. 2005, 7(22), 4995-98) To a stirring colorless clear solution of enyne (1.05 eq) in THF (20 mL) at −78° C., nBuLi (1.10 eq, 1.6M solution in hexanes) was added in ~ca. 15 min. The yellow-brown, clear reaction mixture was stirred for 15 min. at this temperature, then chlorosilane (1.0 eq) taken in THF (15 mL) was added dropwise over a period of 15 min. After stirring at this temperature for 30 min, the white cloudy reaction mixture was brought to room temperature and stirring continued overnight. The white thick reaction mixture was diluted with Et$_2$O (50 mL) and quenched with aq. NH$_4$Cl (100 mL) solution. Aqueous layers extracted with Et$_2$O (2×25 mL) and the combined organic layers were washed with brine (100 mL), and dried over MgSO$_4$. After removal of volatiles, the crude product was purified by chromatography.

Synthesis of 2-triethoxysilyl-1,3-butadiene (2)

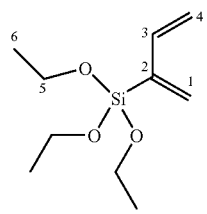

An oven-dried 100 mL 2-neck round-bottom flask equipped with a magnetic stir bar, addition funnel and reflux condenser was charged with magnesium (1.0 g, 0.041 mol) followed by the addition of dibromoethane (250 μL, 11.0 mol %) in THF (5 mL). After stirring ~ca. 5 min (initiation of magnesium activation can be noticed by its silver color and ethane gas liberation), 3.0 mol % of anhydrous ZnCl$_2$ (1.231 mmol, 0.168 g) in THF (5 mL) was added. This mixture was added with additional THF (30 mL) and resulted in a whitish-grey solution which was brought to gentle reflux. Chloroprene in 50% xylenes (5.04 mL, 0.026 mol) and dibromoethane (520 μL, 23.0 mol %) in THF (25 mL) was added dropwise over a 30 min. with the aid of an addition funnel. After the addition, refluxing was further continued for another 45 min. The greenish-grey colored Grignard solution was transferred by canula in to a 250 mL, one-neck round-bottomed flask containing triethoxychlorosilane (5.0 mL, 0.025 mol) in THF (25 mL) at room temperature. The reaction mixture was refluxed (1 h), poured into 0.5M HCl solution (100 mL) and extracted with pentane (2×75 mL). The combined colorless clear organic layers were washed successively with 0.5M HCl (75 mL) and water (2×100 mL). After drying over MgSO$_4$, the solvent was removed under reduced pressure to yield compound 32 with xylenes (1.66:1.0) as a colorless liquid. This compound can be used in the ligand exchange reactions to make compounds 3 and 4 or can be purified by fractional distillation under controlled pressure. The title compound (2) distills as a colorless liquid (4.55 g, 0.021 mmol, 84.7%) after the xylenes (55° C.-60° C., 4 mm). $^1$H NMR (300 MHz, CDCl$_3$) δ 6.45 (dd, J=17.5, 10.7 Hz, 1H, H-3), 5.90 (d, J=3.4 Hz, 1H, H-1), 5.81 (d, J=3.4 Hz, 1H, H-1), 5.54 (d, J=17.5 Hz, 1H, H-4$_{trans}$), 5.14 (d, J=10.7 Hz, 1H, H-4$_{cis}$), 3.84 (q, J=7.0 Hz, 6H, H-5), 1.23 (t, J=7.0 Hz, 9H, H-6); $^{13}$C NMR (300 MHz, CDCl$_3$) δ 141.1 (C-2), 140.4 (C-3), 133.4 (C-1), 117.9 (C-4), 58.6 (C-5), 18.1 (C-6); Anal. calcd for C$_{10}$H$_{20}$O$_3$Si: C, 55.53; H, 9.33. Found: C, 55.93; H, 9.09.

Synthesis of (buta-1,3-dien-2-yl)silatrane (3)

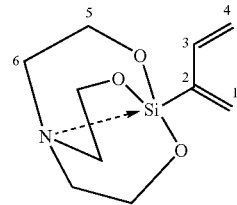

A one neck round bottomed flask (100 mL) fitted with a reflux condenser was charged with THF solution (30 mL). To this flask, triethanolamine (0.620 g, 4.156 mmol), compound 2 (1.0 g, 4.647 mmol) and catalytic amount of KOH powder (5 mol %, 0.032 g, 0.058 mmol) were added successively. Under refluxing for 15 min. the reaction mixture turns clear orange-brown and then the reaction mixture was cooled to room temperature and pentane (100 mL) was added to precipitate the product. The light yellow solid was filtered and washed with ice-cold pentane (3×25 mL) to produce compound 3 (0.857 g, 3.774 mmol, 90.8%) as a yellow fluffy powder. This compound was used to carry-out the cycloaddition reactions without any further purification. X-ray quality crystals were prepared by dual solvent crystallization technique where the compound 3 was first dissolved in dichloroethane and then cyclohexane was added for slow diffusion to produce 3 as white needles: m.p (neat) 104-106° C.; NMR (300 MHz, CDCl$_3$) δ 6.51 (dd, J=17.5, 10.7 Hz, 1H, H-3), 5.74 (d, J=4.5 Hz, 1H, H-1), 5.64 (d, J=4.5 Hz, 1H, H-1), 5.42 (dd, J=17.5, 2.3 Hz, 1H, H-4$_{trans}$), 5.03 (dd, J=10.7, 2.3 Hz, 1H, H-4$_{cis}$), 3.86 (t, J=5.8 Hz, 6H, H-5/6), 2.86 (t, J=5.8 Hz, 6H, H-5/6); $^{13}$C NMR (300 MHz, CDCl$_3$) δ 149.6 (C-2), 143.0 (C-3), 128.3 (C-1), 115.1 (C-4), 57.8

(C-5/6), 51.3 (C-5/6); HRMS calcd for C$_{10}$H$_{17}$O$_3$SiN (M$^+$) 227.0978. found 227.0979. Anal. calcd for C$_{10}$H$_{17}$O$_3$SiN: C, 52.84; H, 7.54. Found: C, 53.37; H, 7.67.

Synthesis of potassium bis(1,2-benzenediolato)-(1,3-butadien-2-yl)silicate (4)

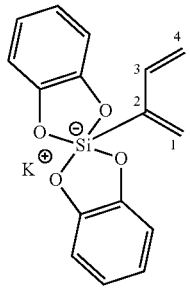

Catechol (5.115 g, 0.046 mol) was dissolved in THF (60 mL) followed by the addition of compound 2 (5.0 g, 0.023 mol) and KOH powder (1.30 g, 0.023 mol) successively. The reaction mixture was refluxed for one hour and the colorless solution turned to clear dark orange. After reflux, the reaction mixture was brought to room temperature, filtered to remove solid particles and pentane was added to precipitate the product as a pale grayish white powder (7.772 g, 0.023 mol, 99.5%). Purification of the title compound was carried out by dissolving the product ( . . . g) in minimum quantity of hot THF, filtration and solidification by cooling the flask at −40° C. for 1 h (% of recovery). For crystallographic studies, recrystallization was carried out by dissolving the compound 4 taken up in a small test tube with small quantity of hot THF and cyclohexane was added carefully along the walls. This test tube was left at room temperature for slow diffusion and the crystals grew out at the junction of the two solvents as white needles: m.p (neat) 242° C. (dec); $^1$H NMR (300 MHz, DMSO) δ 6.49-6.60 (m, 4H, H-6/7), 6.40-6.49 (m, 4H, H-6/7), 6.20 (dd, J=17.5, 10.6 Hz, 1H, H-3), 5.29 (dd, J=17.5, 2.3 Hz, 1H, H-4$_{trans}$), 5.28 (d, J=4.1 Hz, 1H, H-1), 5.18 (d, J=4.1 Hz, 1H, H-1), 4.77 (dd, J=10.6, 2.3 Hz, 1H, H-4$_{cis}$); $^{13}$C NMR (300 MHz, DMSO) δ 151.3 (C-2), 150.3 (C-5), 142.2 (C-3), 123.5 (C-1), 117.3 (C-6/7), 114.5 (C-4), 109.7 (C-6/7). Anal. calcd for C$_{16}$H$_{13}$O$_4$SiK: C, 57.14; H, 3.90. Found: C, 56.96; H, 3.84.

General procedure for Diels-Alder reactions: The diene was dissolved in THF (2 mL) in a thick walled micro wave tube charged with a mini stir-bar. After purging with nitrogen for 2 min., dienophile was added and the tube was closed with an aluminum seal and the reaction was run with continuous stirring at a stipulated time and temperature. The microwave tube was then brought to room temperature and the seal was broken.

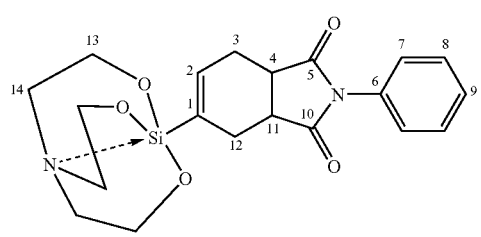

Synthesis of cycloadduct shown below (6): Diene-3 (0.050 g, 0.220 mmol) as shown above and N-phenylmaleimide (0.080 g, 0.462 mmol) was used according to the general procedure for the cycloaddition reaction. After stirring 30 min. at room temperature, the reaction mixture was filtered through a cotton plug and addition of pentane (5 mL) to the filtrate resulted in cycloadduct (6) as white crystalline powder (0.086 g, 0.215 mmol, 97.8%): m.p (neat) 170-172° C.; $^1$H NMR (500 MHz, CDCl$_3$) δ 7.41 (t, J=7.8 Hz, 2H, H-8), 7.33 (t, J=7.4 Hz, 1H, H-9), 7.29 (d, J=7.4 Hz, 2H, H-7), 6.43 (t, J=4.1 Hz, 1H, H-2), 3.77 (t, J=6.0 Hz, 6H, H-13), 2.87-3.19 (m, 2H, H-4, 11), 2.81 (t, J=6.0 Hz, 6H, H-14), 2.66 (dd, J=14.8, 4.0 Hz, 1H, H-12), 2.44-2.59 (m, 2H, H-3, 12), 2.28-2.40 (m, 1H, H-3); $^{13}$C NMR (300 MHz, CDCl$_3$) δ 179.7 (C-5/10), 179.6 (C-5/10), 142.8 (C-1), 134.3 (C-2), 132.5 (C-6), 128.8 (C-8), 128.1 (C-9), 126.8 (C-7), 57.5 (C-13), 51.0 (C-14), 39.81 (C-4/11), 39.76 (C-4/11), 27.6 (C-12), 24.4 (C-3); Anal. calcd for C$_{20}$H$_{24}$N$_2$O$_5$Si: C, 59.98; H, 6.04. Found: C, 60.34; H, 6.43.

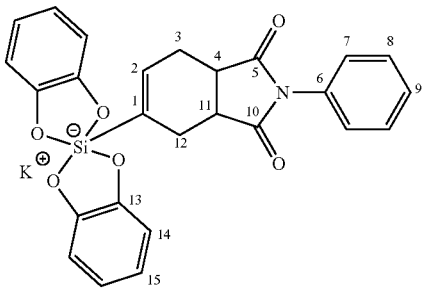

Synthesis of cycloadduct (7) shown below: Diene-4 (0.300 g, 0.893 mmol) and N-phenylmaleimide (0.246 g, 1.421 mmol) was used in the cycloaddition reaction according to the general procedure. After stirring for 30 min. at room temperature, the product was seen precipitating out as a white solid. Further precipitation was carried out by adding pentane (5.0 mL) and quick filtration yielded cycloadduct (7) as a white fluffy powder (0.450 g, 0.884 mmol, 99.0%): m.p (neat) 310° C. (dec); $^1$H NMR (500 MHz, DMSO) δ 7.34-7.46 (m, 3H, H-8, 9), 6.85-6.97 (m, 2H, H-7), 6.54-6.64 (m, 4H, H-15), 6.45-6.54 (m, 4H, H-14), 6.23 (bs, 1H, H-2), 3.08-3.19 (m, 1H, H-11), 2.98-3.07 (m, 1H, H-4), 2.69 (dd, J=14.9, 3.4 Hz, 1H, H-12), 2.33 (ddd, J=15.1, 5.9, 4.0 Hz, 1H, H-3), 2.05-2.17 (m, 2H, H-3, 12); $^{13}$C NMR (500 MHz, DMSO) δ 179.4 (C-5), 178.9 (C-10), 150.5 (C-13), 150.2 (C-13), 142.8 (C-1), 135.5 (C-2), 132.6 (C-6), 128.6 (C-8), 127.9 (C-9), 127.2 (C-7), 117.4 (C-15), 117.1 (C-15), 109.8 (C-14), 109.6 (C-14), 39.1 (C-4/11), 39.0 (C-4/11), 26.9 (C-12), 24.1 (C-3); Anal. calcd for C$_{26}$H$_{20}$O$_6$SiNK: C, 61.29; H, 3.96. Found: C, 61.03; H, 4.35. The unreacted dienophile (0.089 g, 0.514 mmol, 97.4%) was recovered after removal of the organics by using the rotovap.

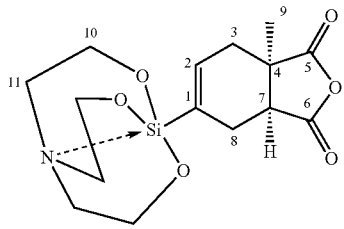

Major Isomer

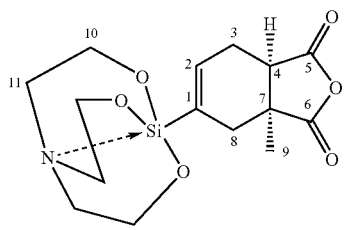

Minor Isomer

Synthesis of cycloadducts shown below: Diene-3 (0.271 g, 1.192 mmol) and citraconic anhydride (0.163 g, 1.454 mmol) was dissolved in 5 mL of THF taken in a seal tube and was heated at 120° C. over a period of 48 h. After which the reaction mixture brought to room temperature, precipitated with pentane (10 mL) followed by vacuum filtration resulted the cycloadduct (9, 10) as white crystalline solid (0.314 g, 0.925 mmol, 77.5%). Major Isomer: $^1$H NMR (500 MHz, C$_6$D$_6$): δ 6.63-6.82 (m, 1H, H-2), 3.32 (t, J=6.0 Hz, 6H, H-10), 3.20 (d, J=14.0 Hz, 1H, H-8), 2.44 (dd, J=15.0, 6.2 Hz, 1H, H-3), 2.21-2.34 (m, 2H, H-7, 8), 1.83 (t, J=6.0 Hz, 6H, H-11), 1.55 (ddd, J=15.0, 3.7, 1.8 Hz, 1H, H-3), 0.78 (s, 3H, H-9); $^{13}$C NMR (300 MHz, C$_6$D$_6$) δ 178.2 (C-), 174.2 (C-), 173.7 (C-), 143.81 (C-), 143.77 (C-), 133.5 (C-2), 57.5 (C-10), 50.6 (C-11), 47.45 (C-7), 46.0 (C-), 33.1 (C-3), 28.0 (C-8), 23.9 (C-9); Minor Isomer: $^1$H NMR (500 MHz, C$_6$D$_6$): δ 6.63-6.82 (m, 1H, H-2), 3.30 (t, J=6.0 Hz, 6H, H-10), 3.08 (d, J=15.0 Hz, 1H, H-8), 2.53 (ddd, J=15.7, 6.2, 2.7 Hz, 1H, H-3), 2.15 (dd, J=6.7, 2.7 Hz, 1H, H-4), 2.03 (dt, J=15.0, 2.2 Hz, 1H, H-8), 1.81 (t, J=6.0 Hz, 6H, H-11), 1.72-1.79 (m, 1H, H-3), 0.97 (s, 3H, H-9); $^{13}$C NMR (300 MHz, C$_6$D$_6$) δ 178.2 (C-), 174.2 (C-), 173.7 (C-), 143.81 (C-), 143.77 (C-), 133.0 (C-2), 57.5 (C-10), 50.6 (C-11), 47.50 (C-4), 46.0 (C-), 36.9 (C-8), 24.2 (C-3), 23.6 (C-9); Anal. calcd for C$_{15}$H$_{21}$NO$_6$Si: C, 53.08; H, 6.24. Found: C, ; H, . Regio isomer ratio 2.0:1.0 (based on $^1$H NMR)

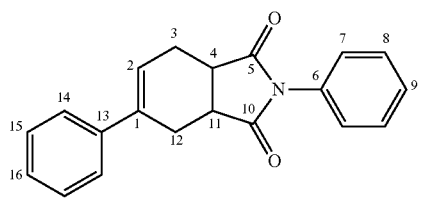

General procedure for cross-coupling reaction by using cycloadduct-6: Cross-coupling reaction was carried out according to the reported literature procedure by using 6 (0.155 g, 0.387 mmol), Pd(OAc)$_2$ (0.024 g, 0.041 mmol), PPh$_3$ (0.024 g, 0.092 mmol), Iodobenzene (0.083 g, 0.407 mmol) were dissolved in DMF (10 mL). After stirring to homogenate the reaction mixture, TBAF (0.118 g, 0.374 mmol) dissolved in THF (5.0 mL) was added and the reaction flask was purged with N$_2$, and heated for 2 h at 90° C. After which the reaction mixture was quenched with water (50 mL), and extracted with Et$_2$O (4×50 mL). The combined organic layers were again washed with water (2×75 mL), dried over MgSO$_4$ and volatiles were removed by rotovap. The brown colored oily crude reaction mixture was subjected to flash chromatography to yield the cross-coupled product as white solid (0.098 g, 0.323 mmol, 83.4%): m.p (neat) 122-124° C.; R$_f$ 0.27 (hexanes/diethyl ether, 1:1); $^1$H NMR (500 MHz, CDCl$_3$) δ 7.38-7.45 (m, 2H, H-8), 7.30-7.38 (m, 5H), 7.24-7.29 (m, 1H), 7.10-7.20 (m, 2H), 6.15-6.27 (m, 1H, H-2), 3.44 (ddd, J=9.5, 6.9, 2.5 Hz, 1H, H-11), 3.35 (ddd, J=9.5, 6.9, 2.5 Hz, 1H, H-4), 3.26 (dd, J=15.1, 2.5 Hz, 1H, H-12), 2.95 (ddd, J=15.5, 6.9, 2.5 Hz, 1H, H-3), 2.64 (ddt, J=15.1, 6.9, 2.5 Hz, 1H, H-12), 2.40-2.50 (m, 1H, H-3); $^{13}$C NMR (500 MHz, CDCl$_3$) δ 179.1 (C-5), 178.9 (C-10), 140.4 (C-13), 140.1 (C-1), 131.2 (C-6), 129.1 (C-8), 128.58 (C-14/15/16), 128.56 (C-14/15/16), 127.5 (C-9), 126.4 (C-7), 125.5 (C-14/15/16), 123.2 (C-2), 40.1 (C-11), 39.5 (C-4), 27.6 (C-12), 25.3 (C-3); Anal. calcd for C$_{20}$H$_{17}$O$_2$N: C, 79.19; H, 5.65. Found: C, 77.88; H, 5.76.

Dimethyl(pent-3-en-1-ynyl)silane

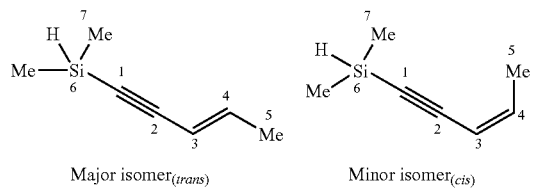

Major isomer$_{(trans)}$     Minor isomer$_{(cis)}$

The general procedure mentioned above using pent-3-en-1-yne (3.142 g, 47.52 mmol), nBuLi (32.0 mL, 51.2 mmol), and dimethylchlorosilane (4.34 g, 45.9 mmol) produced the compound as a colorless clear liquid after purification by using flash chromatography (5.542 g, 44.67 mmol, 94%): Rf 0.39 (100% hexanes); Major isomer(trans): $^1$H NMR (500 MHz, CDCl$_3$) δ 6.22 (dq, J=15.9, 6.8 Hz, 1H, H-4), 5.50-5.54 (m, 1H, H-3), 4.16 (h, J=3.8 Hz, 1H, H-6), 1.77 (dd, J=6.8, 1.8 Hz, 3H, H-5), 0.23 (dd, J=3.8, 1.3 Hz, 6H, H-7); $^{13}$C NMR (300 MHz, CDCl$_3$) δ 141.6 (C-4), 110.7 (C-3), 105.4 (C-2), 89.3 (C-1), 18.6 (C-5), −3.0 (C-7); Minor Isomer(cis): $^1$H NMR (500 MHz, CDCl$_3$) δ 6.04 (dq, J=10.8, 6.8 Hz, 1H, H-4), 5.46-5.50 (m, 1H, H-3), 4.20 (h, J=3.8 Hz, 1H, H-6), 1.89 (dd, J=6.8, 1.8 Hz, 3H, H-5), 0.26 (dd, J=3.8, 1.3 Hz, 6H, H-7); $^{13}$C NMR (300 MHz, CDCl$_3$) δ 140.5 (C-4), 110.0 (C-3), 103.2 (C-2), 95.8 (C-1), 16.1 (C-5), −2.9 (C-7); HRMS calcd for $C_{11}H_{20}Si$ (M+) 124.0708. found 124.0708. Regio isomer ratio 1.0:1.2 (cis to trans, based on $^1H$ NMR).

Methyl(phenyl)(pent-3-en-1-ynyl)silane

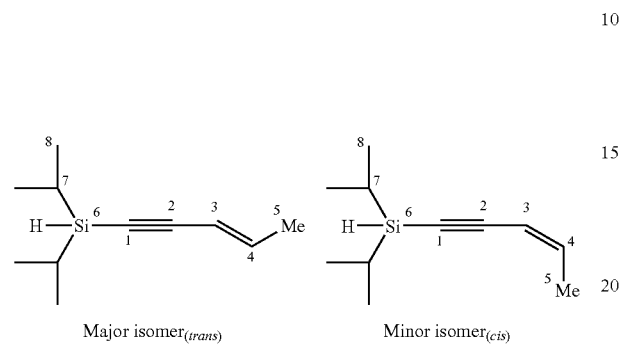

Major isomer(*trans*)      Minor isomer(*cis*)

Pent-3-en-1-yne (1.032 g, 15.61 mmol), nBuLi (10.2 mL, 16.32 mmol) and methyl(phenyl)chlorosilane (2.22 g, 14.18 mmol) produced a crude product which was subjected to column chromatographic purification yielded the compound as a colorless, clear liquid (2.66 g, 14.29 mmol, 96.0%): Rf 0.33 (100% hexanes); Major isomer(cis): $^1H$ NMR (500 MHz, CDCl$_3$) δ 7.65-7.77 (m, 2H, H-9), 7.37-7.50 (m, 3H, H-10, 11), 6.13 (dq, J=10.9, 6.9 Hz, 1H, H-4), 5.61-5.65 (m, 1H, H-3), 4.80 (q, J=3.7 Hz, 1H, H-6), 1.98 (dd, J=6.9, 1.9 Hz, 3H, H-5), 0.57 (d, J=3.7 Hz, 3H, H-7); $^{13}C$ NMR (300 MHz, CDCl$_3$) δ 141.2 (C-4), 134.3 (C-9), 133.9 (C-8), 129.7 (C-11), 128.0 (C-10), 110.0 (C-3), 104.9 (C-2), 93.6 (C-1), 16.2 (C-5), −3.5 (C-7), −3.6 (C-7); Minor isomer(trans) (diagnostic peaks): $^1H$ NMR (500 MHz, CDCl$_3$) δ 6.35 (dq, J=15.7, 6.9 Hz, 1H, H-4), 5.58-5.61 (m, 1H, H-3), 4.75 (q, J=3.7 Hz, 1H, H-6), 1.84 (dd, J=6.9, 1.9 Hz, 3H, H-5), 0.54 (d, J=3.7 Hz, 3H, H-7); $^{13}C$ NMR (300 MHz, CDCl$_3$) δ 142.2 (C-4), 110.6 (C-3), 107.1 (C-2), 87.1 (C-1), 18.7 (C-5); Anal. calcd for $C_{12}H_{14}Si$: C, 77.35; H, 7.57. Found: C, 77.09; H, 7.68. Regio isomer ratio 1.2:1.0 (cis to trans, based on $^1H$ NMR).

General Procedure for the Synthesis of Propargylic Alcohols.

Propargylic alcohols were prepared by the addition of lithium acetylide to the corresponding aldehyde as follows. To a solution of alkyne (1.0 eq) taken in THF (75 mL) at −78° C. was added nBuLi (1.1 eq, 1.6M solution in hexanes) in ~ca. 30 min. The resulting clear orange solution was raised to 0° C. and stirred for an additional 1 h and the flask was again cooled back to −78° C. After the addition of the respective electrophile (1.25 eq), stirring was continued overnight at room temperature followed by quenching with saturated aqueous NH$_4$Cl (100 mL). Aqueous layers were extracted with Et$_2$O (3×50 mL), followed by washing of combined organics with saturated aqueous NaCl solution (100 mL). Solvent was removed by rotary evaporation and the crude product was further purified by flash chromatography.

4-Methyl-1-phenylpent-4-en-2-yn-1-ol

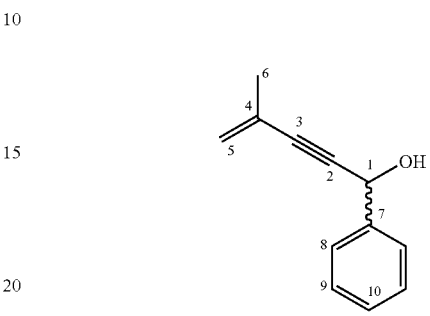

2-Methylbut-1-en-3-yne (3.45 g, 52.19 mmol), nBuLi (36.0 mL, 57.6 mmol) and benzaldehyde (6.642 g, 62.63 mmol) were used according to the general method mentioned above. Purification of the resulting clear yellow-brown crude product yielded the pure product as a clear yellow-brown oil (8.442 g, 49.02 mmol, 93.9%): Rf 0.72 (hexanes/Et$_2$O, 4:1); $^1H$ NMR (300 MHz, CDCl$_3$) δ 7.49-7.69 (m, 2H, H-8), 7.30-7.49 (m, 3H, H-9, 10), 5.58 (d, J=6.2 Hz, 1H, H-1), 5.37 (bs, 1H, H-5), 5.28 (p, J=1.5 Hz, 1H, H-5), 2.43 (d; J=6.2 Hz, 1H, —OH), 1.93 (bs, 3H, H-10); $^{13}C$ NMR (300 MHz, CDCl$_3$) δ 140.6 (C-7), 128.6 (C-9), 128.3 (C-10), 126.6 (C-8), 126.1 (C-4), 126.6 (C-5), 87.8 (C-2/3), 87.7 (C-2/3), 64.9 (C-1), 23.3 (C-6); HRMS calcd for $C_{12}H_{12}O$ (M+) 172.0888. found 172.0885.

2,5-Dimethylhex-5-en-3-yn-2-ol

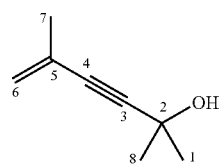

2-Methylbut-1-en-3-yne (3.45 g, 52.19 mmol), nBuLi (36.0 mL, 57.6 mmol) and acetone (3.89 g, 66.96 mmol) produced a brown crude reaction mixture which upon purification by flash chromatography yielded the pure product as a clear yellow oil (2.232 g, 17.97 mmol, 33.4%): Rf 0.22 (hexanes/Et$_2$O, 4:1); $^1H$ NMR (500 MHz, CDCl$_3$) δ 5.21 (s, 1H, H-6), 5.15 (s, 1H, H-6), 2.48-2.93 (bs, 1H, —OH), 1.82 (as, 3H, H-7), 1.49 (as, 6H, H-1, 8); $^{13}C$ NMR (300 MHz, CDCl$_3$)

δ 126.3 (C-5), 121.7 (C-6), 92.8 (C-3), 83.2 (C-4), 65.4 (C-2), 31.4 (C-1, 8), 23.4 (C-7); HRMS calcd for C₈H₁₂O (M+) 124.0888. found 124.0885.

3,6-Dimethylhepta-1,6-dien-4-yn-3-ol 5

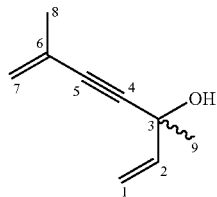

The title compound was prepared according to the general method above by using 2-methylbut-1-en-3-yne (1.725 g, 26.09 mmol), nBuLi (18.0 mL, 28.8 mmol) and but-3-en-2-one (2.194 g, 31.30 mmol). Crude product was purified by flash chromatography (2.229 g, 16.37 mmol, 62.7%): Rf 0.28 (hexanes/Et2O, 4:1); $^1$H NMR (300 MHz, CDCl₃) δ 6.00 (dd, J=17.1, 10.2 Hz, 1H, H-2), 5.49 (dd, J=17.1, 0.7 Hz, 1H, H-1trans), 5.25-5.32 (m, 1H, H-7), 5.18-5.25 (m, 1H, H-7), 5.11 (dd, J=10.2, 0.7 Hz, 1H, H-1 cis), 2.24 (s, 1H, —OH), 1.88 (as, 3H, H-8), 1.56 (s, 3H, H-9); 13C NMR (300 MHz, CDCl₃) δ 142.0 (C-2), 126.2 (C-6), 122.1 (C-7), 113.5 (C-1), 89.9 (C-4/5), 85.9 (C-4/5), 68.5 (C-3), 29.9 (C-9), 23.4 (C-8); HRMS calcd for C₉H₁₃O (M+H)+ 137.0966. found 137.0984.

3-Cyclohexenyl-1-phenylprop-2-yn-1-ol [6f]

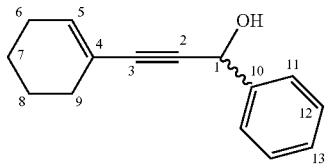

1-Ethynylcyclohex-1-ene (1.987 g, 18.71 mmol), ⁿbutyllithium (14 mL, 1.6M in hexanes, 22.4 mmol) and benzaldehyde (2.43 g, 22.92 mmol) produced a yellow-brown crude reaction mixture which upon purification by flash chromatography yielded the pure product OH as a light yellow colored oily substance (3.84 g, 18.09 mmol, 96.7%): R$_f$ 0.47 (hexanes/Et₂O, 2:1). Spectral data is consistent with earlier reported data.

General Procedure for Syntheses of Siloxy Substituted Enynes (7a, 7c-e see below). Siloxy substituted enynes were prepared by the following method analogous to reported procedures. For example, Alkenynol (1.0 eq), dimethylaminopyridine (10 mol %), and triethylamine (1.01 eq) were added at 0° C. to a 250 mL, single-neck round bottom flask containing hexanes (100 mL). The flask was charged with a stirbar and an addition funnel. After stirring, chlorosilane (taken in hexanes (10 mL) was added dropwise over a period of 20 min. during which the reaction mixture slowly turns to a cloudy white suspension. Later the reaction mixture was brought to ambient temperature and stirring continued overnight. The thick white reaction mixture was filtered through a pad of silica using a sintered funnel, and the silica pad was washed with hexanes (2×20 mL). After removal of volatiles, the crude product was purified using flash chromatography.

(4-Methylpent-4-en-2-ynyloxy)diisopropylsilane [7a]

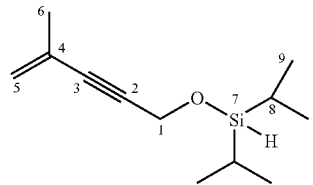

4-Methylpent-4-en-2-yn-1-ol (2.0 g, 20.80 mmol), dimethylaminopyridine (0.252 g, 2.1 mmol), triethylamine (2.126 g, 21.01 mmol) and diisopropylchlorosilane (3.135 g, 20.80 mmol) were used according to the general procedure described above. The resulting clear, light yellow colored crude compound was purified by flash chromatography to yield pure product (3.914 g, 18.62 mmol, 89.5%) as clear colorless solution: R$_f$ 0.82 (hexanes/Et₂O, 9:1); $^1$H NMR (500 MHz, CDCl₃) δ 5.28 (bs, 1H, H-5), 5.22 (bs, 1H, H-5), 4.49 (s, 1H, H-1), 4.21 (s, 1H, H-7), 1.88 (s, 3H, H-6), 0.74-1.37 (m, 14H, H-8, 9); $^{13}$C NMR (300 MHz, CDCl₃) δ 126.5 (C-4), 121.8 (C-5), 86.5 (C-3), 86.3 (C-2), 54.3 (C-1), 23.2 (C-6), 17.3 (C-9), 17.2 (C-9), 12.3 (C-8); Anal. calcd for C₁₂H₂₂OSi: C, 68.51; H, 10.54. Found: C, 68.32; H, 10.73.

(2,5-Dimethylhex-5-en-3-yn-2-yloxy)diisopropylsilane [7c]

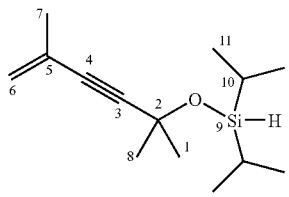

2,5-Dimethylhex-5-en-3-yn-2-ol (6c) (1.772 g, 14.27 mmol), triethylamine (1.690 g, 15.34 mmol), dimethylaminopyridine (0.180 g, 1.50 mmol) and diisopropylchlorosilane (1.918 g, 12.73 mmol) produced 7c as a colorless clear oil (2.232 g, 9.36 mmol, 73.5%) after purification by flash chromatography: R$_f$ 0.90 (hexanes/Et₂O, 4:1); $^1$H NMR (500 MHz, CDCl₃) δ 5.24 (as, J=0.9 Hz, 1H, H-6), 5.19 (p, J=1.4 Hz, 1H, H-6), 4.38 (at, J=1.4 Hz, 1H, H-9), 1.87 (t, J=1.4 Hz, 3H, H-7), 1.52 (s, 6H, H-1, 8), 1.01-1.07 (m, 14H, H-10, 11); $^{13}$C NMR (300 MHz, CDCl₃) δ 126.6 (C-5), 121.2 (C-6), 92.9 (C-3), 84.2 (C-4), 67.4 (C-2), 32.4 (C-1, 8), 23.4 (C-7), 17.6

(C-11), 17.5 (C-11), 12.6 (C-10); HRMS calcd for C$_{14}$H$_{27}$OSi (M+H)$^+$ 239.1831. found 239.1819.

(3,6-Dimethylhepta-1,6-dien-4-yn-3-yloxy)diisopropylsilane [7d]

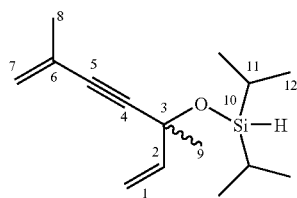

3,6-Dimethylhepta-1,6-dien-4-yn-3-ol (6d) (1.523 g, 11.18 mmol), triethylamine (1.2 g, 11.86 mmol), dimethylaminopyridine (0.153 g, 1.275 mmol) and diisopropylchlorosilane (1.657 g, 10.99 mmol) were used according to the general procedure. The brown, clear crude product was purified by column chromatography to produce the title compound (7d) as a clear colorless solution (2.641 g, 10.54 mmol, 96.3%): Rf 0.91 (hexanes/Et2O, 4:1); 1H NMR (300 MHz, CDCl$_3$) δ 5.92 (dd, J=17.0, 10.2 Hz, 1H, H-2), 5.44 (d, J=17.0 Hz, 1H, H-1), 5.28 (bs, 1H, H-7), 5.22 (p, J=1.5 Hz, 1H, H-7), 5.07 (d, J=10.2 Hz, 1H, H-1), 4.36 (s, 1H, H-10), 1.89 (s, 3H, H-8), 1.56 (s, 3H, H-9), 0.95-1.14 (m, 14H, H-11, 12); 13C NMR (300 MHz, CDCl$_3$) δ 142.6 (C-2), 126.4 (C-6), 121.6 (C-7), 112.8 (C-1), 89.9 (C-4), 86.9 (C-5), 70.5 (C-3), 31.6 (C-9), 23.3 (C-8), 17.6 (C-12), 17.55 (C-12), 17.53 (C-12), 12.7 (C-11), 12.6 (C-11); HRMS calcd for C$_{15}$H$_{26}$OSi (M+) 250.1753. found 250.1744.

(3-Cyclohexenylprop-2-ynyloxy)diisopropylsilane [7e]

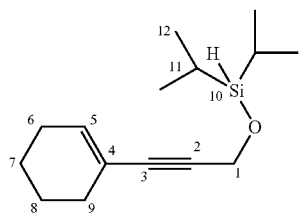

3-Cyclohexenylprop-2-yn-1-ol (6l) (1.236 g, 12.86 mmol), triethylamine (1.30 g, 12.85 mmol), dimethylaminopyridine (0.152 g, 1.267 mmol) and diisopropylchlorosilane (1.918 g, 12.73 mmol) were used to yield compound 7e (1.680 g, 6.71 mmol, 52.7%) as a colorless, clear oily substance after purification by flash chromatography: R$_f$ 0.85 (hexanes/Et2O, 4:1); 1H NMR (500 MHz, CDCl$_3$) δ 6.08 (h, J=1.8 Hz, 1H, H-5), 4.48 (s, 2H, H-1), 4.20 (s, 2H, H-10), 1.98-2.17 (m, 4H, H6-9), 1.49-1.71 (m, 4H, H6-9), 0.96-1.12 (m, 14H, H-11, 12). 13C NMR (300 MHz, CDCl$_3$) δ 134.8 (C-5), 120.3 (C-4), 87.1 (C-2/3), 84.4 (C-2/3), 54.3 (C-1), 29.0 (C$_{6-9}$), 25.6 (C$_{6-9}$), 22.2 (C$_{6-9}$), 21.5 (C$_{6-9}$), 17.3 (C-12), 17.2 (C-12), 12.3 (C-11); HRMS calcd for C$_{15}$H$_{26}$NaOSi (M+Na)$^+$ 273.1651. found 273.1639.

General Procedure for Synthesis of Siloxacyclopentene Containing-1,3-Dienes by Potassium tert-Butoxide Catalyzed trans-Hydrosilylation of Siloxy Substituted Enynes [8a, 8e].[7] Potassium tert-butoxide (10 mol %) taken in THF (10 mL) was added slowly ca. ~10 min. to a flask containing a solution of siloxy substituted enynes (8a, 8e) in THF (10 mL). Stirring was continued for 1 h at ambient temperature, and the reaction mixture was diluted with Et$_2$O (50 mL) followed by quenching with saturated NH$_4$Cl (100 mL) solution. The organic layer was separated and aqueous layers were extracted with Et$_2$O (3×50 mL). Combined organic layers were washed with brine, dried over MgSO$_4$. Volatiles were removed and the crude reaction mixture was subjected to purification by using flash chromatography and/or a chromatotron.

2,5-Dihydro-2,2-diisopropyl-3-(prop-1-en-2-yl)-1,2-oxasilole [8a]

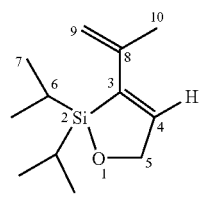

(4-Methylpent-4-en-2-ynyloxy)diisopropylsilane (1.662 g, 7.90 mmol) and KO$^t$Bu (0.092 g, 0.8199 mmol) were used according to the general procedure mentioned above. The light brown clear solution was subjected to column chromatography and yielded 8a as colorless, clear liquid (1.192 g, 5.666 mmol, 71.7%): R$_f$ 0.37 (hexanes/Et$_2$O, 15:1); 1H NMR (500 MHz, CDCl$_3$) δ 6.68 (t, J=1.9 Hz, 1H, H-4), 4.99 (s, 1H, H-9), 4.80 (s, 1H, H-9), 4.63 (dd, J=1.9, 0.9 Hz, 2H, H-5), 1.94 (s, 3H, H-10), 1.09-1.19 (m, 2H, H-6), 1.04 (d, J=7.3 Hz, 6H, H-7), 0.99 (d, J=7.3 Hz, 6H, H-7); 13C NMR (300 MHz, CDCl$_3$) δ 142.4 (C-4), 142.1 (C-8), 139.8 (C-3), 116.3 (C-9), 72.7 (C-5), 20.6 (C-10), 17.3 (C-7), 17.0 (C-7), 13.3 (C-6); Anal. calcd for C$_{12}$H$_{22}$OSi: C, 68.51; H, 10.54. Found: C, 68.24; H, 10.61.

3-Cyclohexenyl-2,5-dihydro-2,2-diisopropyl-1,2-oxasilole [8e]

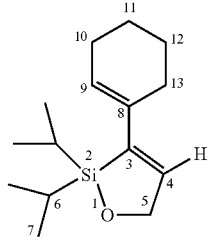

Using (3-cyclohexenylprop-2-ynyloxy)diisopropylsilane (0.715 g, 2.854 mmol) and KO$^t$Bu (0.037 g, 0.330 mmol) produced a crude product as a colorless, clear liquid which upon flash chromatography yielded the title compound as clear colorless liquid; R$_f$ 0.45 (hexanes/Et$_2$O, 15:2). The isolated compound was found to have an impurity of about ~20% with a close Rf value, hence the compound was further purified by using a chromatotron (2.0 mm silica gel) (0.537 g, 2.144 mmol, 75.1%). 1H NMR (300 MHz, CDCl$_3$) δ 6.56 (s, 1H, H-4), 5.57 (s, 1H, H-9), 4.61 (s, 1H, H-5), 2.17-2.26 (m, 2H, H-13), 2.03-2.16 (m, 2H, H-10), 1.64-1.75 (m, 2H, H-12), 1.52-1.64 (m, 2H, H-11), 1.06-1.20 (m, 2H, H-6), 1.04 (d, J=6.6 Hz, 6H, H-7), 0.98 (d, J=6.8 Hz, 6H, H-7); $^{13}$C NMR (300 MHz, CDCl$_3$) δ 140.3 (C-3), 138.0 (C-4), 135.7 (C-8), 128.9 (C-9), 77.8 (C-5), 26.2 (C-13), 26.0 (C-10), 22.8 (C-12), 22.4 (C-11), 17.4 (C-7), 17.1 (C-7), 13.4 (C-6); HRMS calcd for C$_{15}$H$_{27}$OSi (M+H)$^+$ 251.1831. found 251.1828.

One-pot, Tandem Synthesis of Siloxy Substituted Enynes and Their Potassium tert-Butoxide Catalyzed trans-Hydrosilylation Reactions Using 1,1,3,3-Tetramethyldisilazane The respective Alkenynols (1.0 eq) were taken in a 50 mL, round bottom flask kept in a water bath under N$_2$ inlet. After the slow addition of tetramethyldisilazane (0.6 eq) over ~5 min using a syringe, water bath was removed and stirring continued overnight at room temperature. Then volatiles were removed by rotovap and the crude reaction mixture was dissolved in THF (10 mL), and the flask was cooled in a water-bath at ambient temperature. The flask was purged with N$_2$ for 2 min, then Ko$^t$Bu (10 mol %) was added in THF (3×5 mL) solution over a period of 10 min. After the addition, the water bath was removed and stirring continued for 1 h. at room temperature. The reaction mixture was diluted with Et$_2$O (20 mL), followed by quenching with saturated NH$_4$Cl (50 mL). The organic layer was separated and aqueous layers were extracted with Et2O (3×20 mL). The combined organics were washed with satd. NaCl solution (50 mL), dried over MgSO$_4$ and volatiles were removed by rotovap. The crude reaction mixture was purified by means of column chromatography or a chromatotron.

2,5-Dihydro-2,2-dimethyl-3-(prop-1-en-2-yl)-1,2-oxasilole [10a]

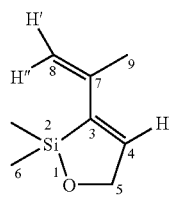

Using 4-methylpent-4-en-2-yn-1-ol (1.792 g, 18.64 mmol), 1,1,3,3-tetramethyldisilazane (1.504 g, 11.28 mmol) and KO$^t$Bu (0.217 g, 1.934 mmol) according to the above general procedure resulted a clear brown colored crude reaction mixture which upon purification by column chromatography yielded 10a as a clear colorless oil (2.014 g, 13.05 mmol, 70.0%): Rf 0.68 (pentane/Et$_2$O, 3:1); $^1$H NMR (500 MHz, CDCl$_3$) δ 6.60 (as, 1H, H-4), 4.99 (s, 1H, H-8'), 4.82 (s, 1H, H-8"), 4.66 (s, 2H, H-5), 1.93 (s, 3H, H-9), 0.33 (as, 6H, H-6); $^{13}$C NMR (300 MHz, CDCl$_3$) δ 142.2 (C-3), 141.3 (C-7), 141.2 (C-4), 115.7 (C-8), 71.9 (C-5), 20.4 (C-9), 0.45 (C-6); HRMS calcd for C$_8$H$_{14}$OSi (M$^+$) 154.0814. found 154.0813.

(3-Cyclohexenylprop-2-ynyloxy)dimethylsilane [9e]

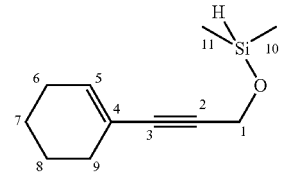

3-Cyclohexenylprop-2-yn-1-ol (2.509 g, 26.10 mmol) and 1,1,3,3-tetramethyldisilazane (1.527 g, 11.45 mmol) were used according to the method mentioned above to produce the title compound as a brown clear liquid (3.916 g, 20.15 mmol, 77.2%). The crude reaction mixture was analyzed by $^1$H NMR to confirm the product formation and used in KOtBu catalyzed transhydrosilylation reaction.

3-Cyclohexenyl-2,5-dihydro-2,2-dimethyl-1,2-oxasilole [10e]

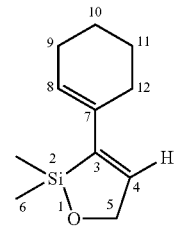

(3-Cyclohexenylprop-2-ynyloxy)dimethylsilane (2.77 g, 14.25 mmol) and KO$^t$Bu (0.160 g, 1.425 mmol) were used according to the general procedure. The brown oily crude reaction mixture was purified by flash chromatography using hexanes/Et$_2$O (6:1) as eluant to produce 10e as a clear colorless oil (1.437 g, 7.394 mmol, 51.9%), which was used in Diels-Alder reactions without further purification. Analytical samples were prepared from this chromatographic compound (0.235 g, 1.209 mmol) by using a chromatotron (2.0 mm, silica gel) yielded the title compound as a colorless clear liquid in pure form (0.167 g, 0.859 mmol, 71.1%): R$_f$ 0.34 (hexanes/Et$_2$O, 8:1); $^1$H NMR (300 MHz, CDCl$_3$) δ 6.49 (s, 1H, H-4), 5.61 (s, 1H, H-8), 4.64 (s, 1H, H-5), 2.04-2.26 (m, 4H, H-9, 12), 1.51-1.77 (m, 4H, H-10, 11), 0.32 (s, 6H, H-6); $^{13}$C NMR (300 MHz, CDCl$_3$) δ 142.6 (C-3), 136.9 (C-4), 135.2 (C-7), 128.8 (C-8), 72.0 (C-5), 26.1 (C-9, 12), 22.6 (C-10/11), 22.4 (C-10/11), 0.74 (C-6); HRMS calcd for C$_{11}$H$_{18}$OSi (M$^+$) 194.1127. found 194.1121.

General Procedure for Diels-Alder Reactions of Siloxacyclopentene Containing-1,3-Dienes. Diene and dienophile were taken together in a thick-walled sealed tube containing THF (5.0 mL), purged with N$_2$ for about. 2 min and the tube was sealed and heated at 90° C. for the stipulated time. After which the seal was broken, and the volatiles were removed then the crude product was chromatographed to obtain cycloadducts almost in pure form.

(5αS,8αS,8βS)-5,5a-dihydro-3,3-diisopropyl-4-methyl-7-phenyl-1H-[1,2]oxasilolo[4,3-e]isoindole-6,8 (3H,7H,8αH,8βH)-dione [11a] and (5αS,8αS,8βR)-5,5a-Dihydro-3,3-diisopropyl-4-methyl-7-phenyl-1H-[1,2]oxasilolo[4,3-e]isoindole-6,8(3H,7H,8αH, 8βH)-dione [11b].

Compound 8a (2,5-Dihydro-2,2-diisopropyl-3-(prop-1-en-2-yl)-1,2-oxasilole) (0.496 g, 2.358 mmol) and N-phenylmaleimide (0.201 g, 1.157 mmol) were taken together according to above procedure and heated for 36 h. After removal of volatiles, the crude reaction mixture was dissolved in CHCl₃ (2.0 mL) followed by purification with flash chromatography using hexanes/Et₂O, 2:1 resulting in elution of unreacted (excess) diene prior to the cycloadducts. After elution of unreacted (excess) diene, polarity of the mobile phase was increased (hexanes/Et₂O, 1:1) to yield both the stereo isomers one after the other as in pure form (0.382 g, 0.996 mmol, 86.2%).

Minor Isomer [11a]:

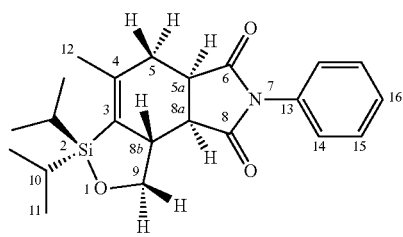

After eluting the excess diene with hexanes/diethyl ether (2:1), increasing the polarity yields (hexanes/Et₂O, 1:1) stereo isomer-11a (exo) as a viscous clear liquid almost in pure form (0.180 g, 0.469 mmol, 47.1%): $R_f$ 0.61 (hexanes/Et₂O, 1:1); ¹H NMR (500 MHz, CDCl₃) δ 7.47 (t, J=7.4 Hz, 2H, H-15), 7.38 (t, J=7.4 Hz, 1H, H-16), 7.29 (d, J=7.4 Hz, 2H, H-14), 4.64 (dd, J=10.0, 7.6 Hz, 1H, H-9), 3.90 (dd, J=10.0, 8.6 Hz, 1H, H-9), 3.12 (ddd, J=17.8, 9.5, 8.1 Hz, 1H, H-5a), 2.73 (dd, J=15.9, 8.1 Hz, 1H, H-5), 2.63 (t, J=9.5 Hz, 1H, H-8a), 2.50-2.60 (m, 1H, H-8b), 2.22 (dd, J=15.9, 10.0 Hz, 1H, H-5), 1.96 (dd, J=1.7, 1.0 Hz, 3H, H-12), 1.11-1.20 (m, 2H, H-10), 1.09 (d, J=7.1, 3H, H-11), 1.02 (d, J=7.4, 6H, H-11), 1.00 (d, J=7.4, 3H, H-11); ¹³C NMR (300 MHz, CDCl₃) δ 178.3 (C-6), 177.9 (C-8), 143.9 (C-4), 131.7 (C-13), 131.0 (C-3), 129.1 (C-15), 128.5 (C-16), 126.3 (C-14), 72.7 (C-9), 43.8 (C-8a), 42.9 (C-8b), 39.7 (C-5a), 30.8 (C-5), 25.7 (C-12), 17.9 (C-11), 17.3 (C-11), 17.1 (C-11), 13.1 (C-10), 12.6 (C-10); HRMS calcd for C₂₂H₃₀NO₃Si (M+H)⁺ 384.1995. found 384.1979.
¹H NMR (300 MHz, C₆D₆) δ 6.82 (d, J=7.9 Hz, 2H, H-14), 6.54 (t, J=7.9 Hz, 2H, H-15), 6.40 (t, J=7.9 Hz, 1H, H-16), 4.20 (dd, J=9.8, 8.2 Hz, 1H, H-9), 3.29 (dd, J=9.8, 8.8 Hz, 1H, H-9), 1.59-1.79 (m, 3H, H-5, 5a, 8a), 1.25 (t, J=9.5 Hz, 1H, H-8b), 1.08 (dd, J=17.7, 12.6 Hz, 1H, H-5), 0.93 (at, J=1.3 Hz, 3H, H-12), 0.48 (d, J=6.9 Hz, 3H, H-11), 0.36-0.46 (m, 2H, H-10), 0.43 (d, J=5.4 Hz, 3H, H-11), 0.30-0.37 (m, 6H, H-11).

Major Isomer [11b]:

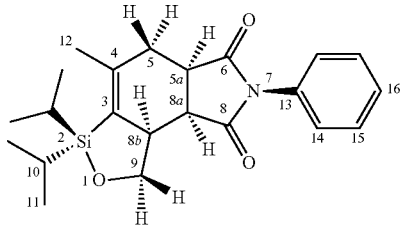

Once 11a elution was completed, polarity of the mobile phase was gradually increased to 100% Et₂O, resulting in the elution of other stereo isomer-11b (endo) as major product in the form of a colorless clear viscous liquid (0.202 g, 0.527 mmol, 52.9%): $R_f$ 0.24 (hexanes/Et₂O, 1:1); ¹H NMR (500 MHz, C₆D₆) δ 7.40 (d, J=7.7 Hz, 2H, H-14), 7.12 (t, J=7.7 Hz, 2H, H-15), 6.97 (t, J=7.7 Hz, 1H, H-16), 4.94 (dd, J=10.0, 7.7 Hz, 1H, H-9), 4.31 (dd, J=10.0, 9.0 Hz, 1H, H-9), 2.64 (d, J=15.4 Hz, 1H, H-5), 2.36-2.52 (m, 2H, H-5a, 8a), 2.11-2.26 (m, 1H, H-8b), 1.68 (d, J=2.6 Hz, 3H, H-12), 1.59-1.73 (m, 1H, H-5), 1.06 (d, J=6.7 Hz, 3H, H-11), 1.01 (d, J=5.9 Hz, 3H, H-11), 0.94 (d, J=5.9 Hz, 3H, H-11), 0.90 (d, J=6.7 Hz, 3H, H-11), 0.88-1.12 (m, 2H, H-10); ¹³C NMR (300 MHz, C₆D₆) δ 177.9 (C-6), 176.0 (C-8), 144.8 (C-4), 133.0 (C-13), 132.5 (C-3), 128.8 (C-15), 128.1 (C-16), 126.4 (C-14), 67.7 (C-9), 42.7 (C-8b), 40.8 (C-5a/8a), 40.7 (C-5a/8a), 31.1 (C-5), 26.3 (C-12), 18.2 (C-11), 17.7 (C-11), 17.4 (C-11), 13.4 (C-10), 13.3 (C-10); HRMS calcd for C₂₂H₃₀NO₃NaSi (M+Na)⁺ 406.1814. found 406.1770. The unreacted diene (excess) was recovered after the volatiles were rotovapped (0.093 g, 0.442 mmol, 36.8%).
¹H NMR (500 MHz, CDCl₃) δ 7.43 (t, J=7.9 Hz, 2H, H-15), 7.35 (t, J=7.9 Hz, 1H, H-16), 7.19 (d, J=7.9 Hz, 2H, H-15), 4.65 (dd, J=10.1, 8.2 Hz, 1H, H-9), 4.37 (dd, J=10.1, 8.8 Hz, 1H, H-9), 3.25-3.40 (m, 2H, H-5a, 8a), 2.76-2.92 (m, 2H, H-5, 8b), 2.37 (dd, J=14.8, 6.3 Hz, 1H, H-5), 1.93 (ad, J=2.5 Hz, 3H, H-12), 1.04-1.11 (m, 2H, H-10), 1.02 (d, J=7.3 Hz, 3H, H-11), 0.98 (d, J=7.8 Hz, 3H, H-11), 0.97 (d, J=7.3 Hz, 3H, H-11), 0.94 (d, J=7.8 Hz, 3H, H-11).

(5αS,8αS,8βR)-5,5a-Dihydro-3,3,4-trimethyl-7-phenyl-1H-[1,2]oxasilolo[4,3-e]isoindole-6,8(3H, 7H,8αH,8βH)-dione [1,2]

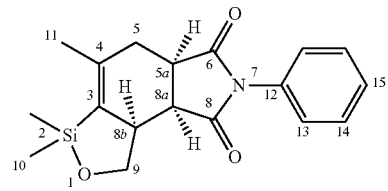

Compound 10a (2,5-Dihydro-2,2-dimethyl-3-(prop-1-en-2-yl)-1,2-oxasilole) (0.449 g, 2.910 mmol) and N-phenylmaleimide (0.195 g, 1.126 mmol) were used according to the general procedure. After heating for 24 h, and flash chromatography resulted in eluting the excess unreacted diene (pentane/Et₂O, 2:1) as first eluant followed by increasing polarity of the mobile phase (100% Et₂O) yields 12 (endo) as a clear colorless viscous liquid (0.323 g, 0.986 mmol, 87.5%): $R_f$ 0.53 (100% Et₂O); ¹H NMR (500 MHz, C₆D₆) δ 7.34 (ad, J=7.8 Hz, 2H, H-13), 7.10 (at, J=7.8 Hz, 2H, H-14), 6.96 (at, J=7.6 Hz, 1H, H-15), 5.02 (dd, J=10.3, 6.3 Hz, 1H, H-9), 4.28 (dd, J=10.3, 8.6 Hz, 1H, H-5), 2.56 (dd, J=14.6, 1.8 Hz, 1H, H-5), 2.46 (ddd, J=8.8, 6.8, 1.8 Hz, 1H, H-5a), 2.39 (dd, J=8.8, 6.8 Hz, 1H, H-8a), 2.15-2.25 (m, 1H, H-8b), 1.65 (add, J=14.6, 6.8, 1H, H-5), 1.60 (as, 3H, H-11), 0.20 (s, 3H, H-10), 0.14 (s, 3H, H-10); $^{13}$C NMR (300 MHz, C$_6$D$_6$) δ 177.8 (C-6/8), 176.3 (C-6/8), 144.4 (C), 135.6 (C), 132.9 (C), 129.0 (C-14), 128.2 (C-15), 126.5 (C-13), 66.7 (C-9), 42.5 (C-8b), 41.5 (C-8a), 40.9 (C-5a), 31.6 (C-5), 24.5 (C-11), −0.52 (C-10); HRMS calcd for C$_{18}$H$_{22}$NO$_3$Si (M+H)$^+$ 328.1369. found 328.1364. The unreacted (excess) diene (0.192 g, 1.244 mmol, 69.8%) was recovered after removal of volatiles by rotovap and was found in pure form: R$_f$ 0.78 (pentane/Et$_2$O, 1:2).

$^1$H NMR (500 MHz, CDCl$_3$) δ 7.44 (t, J=7.7 Hz, 2H, H-14), 7.35 (t, J=7.4 Hz, 1H, H-15), 7.16 (ad, J=8.3 Hz, 2H, H-13), 4.72 (dd, J=10.1, 6.6 Hz, 1H, H-9), 4.35 (dd, J=10.1, 8.5 Hz, 1H, H-9), 3.24-3.36 (m, 2H, H-5a, 8a), 2.73-2.87 (m, 2H, H-5, 8b), 2.28 (dd, J=14.8, 6.3 Hz, 1H, H-5), 1.89 (bs, 3H, H-11), 0.29 (s, 3H, H-10), 0.18 (s, 3H, H-10); $_{13}$C NMR (300 MHz, CDCl$_3$) δ 178.5 (C-6), 176.8 (C-8), 144.6 (C-4), 134.7 (C-3), 131.9 (C-12), 129.1 (C-13), 128.5 (C-15), 126.3 (C-14), 66.5 (C-9), 41.9 (C-8b), 41.5 (C-8a), 40.8 (C-5a), 31.5 (C-5), 24.7 (C-11), −0.65 (C-10), −0.71 (C-10).

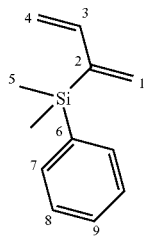

Synthesis of (buta-1,3-dien-2-yl)-dimethyl(phenyl)silane (1f). Chloroprene (1a) (4.575 g, 51.69 mmol) and phenyldimethylchlorosilane (8.034 g, 47.06 mmol) were used according to Method-A to yield light yellow colored crude product (14.38 g) as a mixture of diene, 1f and xylenes. The crude product was subjected for fractional distillation at reduced pressure (20 mm, 45° C.) resulted in diene, 1f (7.772 g) as a brown colored liquid, which was further purified by flash chromatography (100% pentanes) to yield the title compound as a light yellow colored liquid in pure form (8.36 g, 44.39 mmol, 96.8%): R$_f$ 0.63 (100% pentanes); $^1$H NMR (500 MHz, CDCl$_3$) δ 7.49-7.55 (m, 2H, H-7), 7.31-7.37 (m, 3H, H-8, 9), 6.46 (dd, J=17.7, 10.9 Hz, 1H, H-3), 5.88 (d, J=3.2 Hz, 1H, H-1), 5.51 (d, J=3.2 Hz, 1H, H-1), 5.10 (d, J=17.7 Hz, 1H, H-4$_{trans}$), 5.00 (d, J=10.9 Hz, 1H, H-4$_{cis}$), 0.43 (s, 9H, H-5); $^{13}$C NMR (300 MHz, CDCl$_3$) δ 147.6 (C-2), 141.1 (C-3), 138.2 (C-6), 133.9 (C-7), 130.4 (C-1), 129.0 (C-9), 127.8 (C-8), −2.3 (C-5); HRMS calcd for C$_{12}$H$_{16}$Si (M$^+$) 188.1021. found 188.1020. Anal. calcd for C$_{12}$H$_{16}$Si: C, 76.53; H, 8.56.

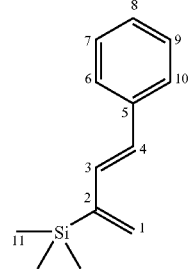

Synthesis of Trimethyl[(E)-4-phenyl-1,3-butadien-2-yl]silane (2b).$^6$ 1-[(E)-3-Bromobuta-1,3-dienyl]benzene (1.985 g, 9.494 mmol) and trimethylsilylchloride (1.37 g, 12.61 mmol) were used according to Method-B, results the crude compound as dark brown liquid. The crude residue after purification by flash chromatography (hexanes/Et$_2$O, 9:1) yields compound 2b as brown-yellow oil (1.562 g, 7.728 mmol, 85%). Spectroscopic data was not reported earlier:$^{7,8}$ R$_f$ 0.15 (hexanes/Et$_2$O, 9:1); $^1$H NMR (500 MHz, CDCl$_3$) δ 7.43 (ad, J=7.7 Hz, 2H, H-6), 7.34 (t, J=7.7 Hz, 1H, H-7), 7.24 (t, J=7.4 Hz, 1H, H-8), 6.94 (d, J=16.5 Hz, 1H, H-3), 6.64 (d, J=16.5 Hz, 1H, H-4), 5.89 (d, J=3.0 Hz, 1H, H-1), 5.53 (d, J=3.0 Hz, 1H, H-1), 0.27 (s, 9H, H-9); $^{13}$C NMR (300 MHz, CDCl$_3$) δ 148.9 (C-2), 137.7 (C-5), 134.0 (C-3), 130.5 (C-4), 128.6 (C-1), 128.5 (C-7), 127.3 (C-8), 126.3 (C-6), 0.8 (C-9); HRMS calcd for C$_{13}$H$_{18}$Si (M$^+$) 202.1178. Anal. calcd for C$_{13}$H$_{18}$Si: C, 77.16; H, 8.97.

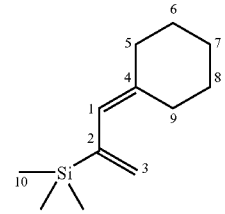

Synthesis of (1-cyclohexylideneprop-2-en-2-yl)trimethylsilane (3b). Chlrotrimethylsilane (0.685 g, 6.303 mmol) and (2-bromoallylidene)cyclohexene (3a) (0.929 g, 4.644 mmol) were used according to Method-B. The resulted dark brown crude residue after purification by flash chromatography (hexanes/Et$_2$O, 15:1→9:1) yielded compound 3b as a brown-yellow oil (0.483 g, 2.488 mmol, 47.3%): R$_f$ 0.84 (hexanes/Et$_2$O, 15:1); $^1$H NMR (500 MHz, CDCl$_3$) δ 5.71 (s, 1H, H-1), 5.40-5.49 (m, 2H, H-3), 2.10-2.23 (m, 4H, H-5,9), 1.54-1.60 (m, 4H, H-6,8), 1.41-1.50 (m, 2H, H-7), 0.07 (s, 9H, H-10); $^{13}$C NMR (300 MHz, CDCl$_3$) δ 150.3 (C-2), 140.5 (C-4), 125.1 (C-3), 123.5 (C-1), 37.4 (C-5/9), 29.3 (C-5/9), 29.0 (C-6/8), 28.3 (C-7), 26.9 (C-6/8), −1.95 (C-10); HRMS calcd for C$_{12}$H$_{22}$Si (M$^+$) 194.1491. found 194.1489.

General Procedure for Diels-Alder Reactions.

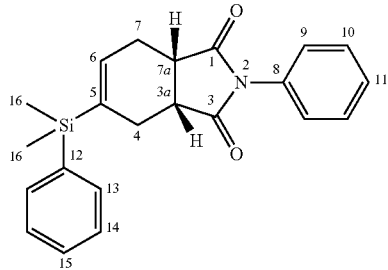

6a

Synthesis of 3a,4,7,7a-tetrahydro-5-[dimethyl(phenyl)silyl]-2-phenyl-2H-isoindole-1,3-dione (6a); $^1$H NMR (500 MHz, CDCl$_3$) δ 7.41-7.54 (m, 4H), 7.29-7.41 (m, 4H), 7.09-7.20 (m, 2H, H-10), 6.34 (p, J=3.2 Hz, 1H, H-6), 3.18-3.30 (m, 2H, H-3a,7a), 2.71-2.88 (m, 2H, H-4,7), 2.22-2.36 (m, 2H, H-4,7), 0.36 (s, 3H, H-16), 0.35 (s, 3H, H-16); $^{13}$C NMR (300 MHz, CDCl$_3$) δ 179.1 (C-1/3), 178.7 (C-1/3), 140.7 (C-5), 138.4 (C-6), 137.0 (C-12), 133.9 (CH), 132.0 (C-8), 129.2 (CH), 129.0 (CH), 128.4 (CH), 127.8 (CH), 126.3 (CH), 39.3 (C-3a/7a), 39.2 (C-3a/7a), 26.4 (C-4/7), 25.0 (C-4/7), −3.88 (C-16), −3.89 (C-16); HRMS calcd for C$_{22}$H$_{23}$NO$_2$Si (M$^+$) 361.1498. found 361.1490. Anal. calcd for C$_{22}$H$_{23}$NO$_2$Si: C, 73.10; H, 6.42. Found: C, 72.63; H, 6.38.

General Procedure for the Cross-Coupling Reactions. These reactions were carried out by analogy to a reported literature procedure. Diels-Alder cycloadduct (1.0 eq), Pd(OAc)$_2$ (10 mol %), PPh$_3$ (20 mol %) and arylhalide (1.2 eq) were taken in a seal tube charged with micro stir-bar, and dissolved in dis. DMF (5 mL). This transparent yellow colored reaction mixture was stirred to homogenate followed by addition of TBAF (1.2 eq) dissolved in THF (0.5 mL), which results in a reaction mixture dark brown in color, which was purged with N$_2$, and heated in an oil bath for 2 h at 90° C. During the course of reaction, the reaction mixture turned dark black and the formation of active palladium species (Pd$^{II}$→Pd$^0$) was also noticed as the catalyst slowly turned to black solid. The reaction mixture was then quenched with water (50 mL), and extracted with Et$_2$O (4×30 mL). The combined organic layers were again washed with water (2×75 mL), dried over MgSO$_4$ and volatiles were removed by rotary evaporation. The resulting cross-coupled cycloadduct residue was purified by flash chromatography.

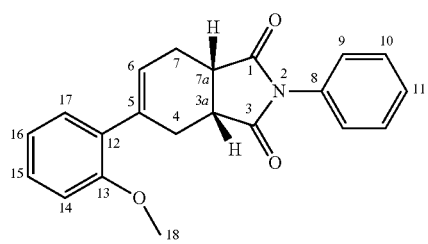

7a

Synthesis of (3aR,7aS)-5-(2-methoxyphenyl)-2-phenyl-3a,4,7,7a-tetrahydro-1H-isoindole-1,3(2H)-dione (7a). Cycloadduct 4a (0.101 g, 0.252 mmol), Pd(OAc)$_2$ (0.020 g, 0.034 mmol), PPh$_3$ (0.024 g, 0.092 mmol), 2-iodoanisole (0.084 g, 0.359 mmol) and TBAF (0.110 g, 0.349 mmol) were used according to the general procedure mentioned above. The resulting brown colored oily crude reaction mixture was subjected to flash chromatography to yield the cross-coupled product 7a as a yellow solid (0.048 g, 0.144 mmol, 57.1%): R$_f$ 0.42 (diethyl ether/hexanes, 2:1); $^1$H NMR (500 MHz, CDCl$_3$) δ 7.44 (t, J=8.1 Hz, 2H, H-10), 7.37 (t, J=7.5 Hz, 1H, H-11), 7.18-7.25 (m, 3H, H-9, 15), 7.08 (d, J=7.5 Hz, 1H, H-17), 6.90 (t, J=7.5 Hz, 1H, H-16), 6.83 (d, J=8.1 Hz, 1H, H-14), 6.03 (p, J=3.4 Hz, 1H, H-6), 3.67 (s, 3H, H-18), 3.36 (ddd, J=9.1, 7.7, 2.4 Hz, 1H, H-3a), 3.32 (ddd, J=9.1, 6.7, 2.6 Hz, 1H, H-7a), 3.07 (dd, J=15.4, 2.4 Hz, 1H, H-4), 2.94 (ddd, J=15.4, 6.7, 2.6 Hz, 1H, H-7), 2.63 (ddt, J=15.4, 7.7, 2.4 Hz, 1H, H-4), 2.37-2.50 (m, 1H, H-7); $^{13}$C NMR (300 MHz, CDCl$_3$) δ 179.2 (C-1), 178.8 (C-3), 156.5 (C-13), 139.5 (C-5), 132.3 (C-8), 130.9 (C-12), 129.2 (C-11/17), 129.0 (C-10), 128.8 (C-11/17), 128.5 (C-15), 126.7 (C-9), 125.1 (C-6), 120.6 (C-16), 110.5 (C-14), 54.9 (C-18), 40.0 (C-3a/7a), 39.8 (C-3a/7a), 28.9 (C-4), 24.5 (C-7); HRMS calcd for C$_{21}$H$_{19}$NO$_3$ (M$^+$) 333.1365, Anal. calcd for C$_{21}$H$_{19}$NO$_3$: C, 75.66; H, 5.74.

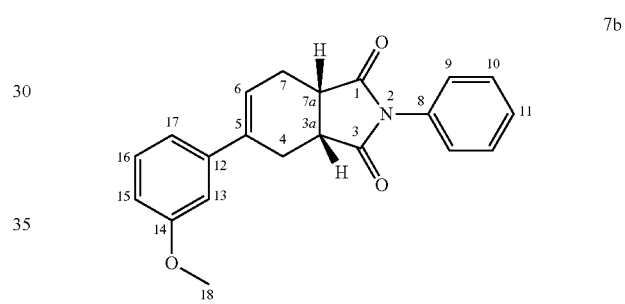

7b

Synthesis of (3aR,7aS)-5-(3-methoxyphenyl)-2-phenyl-3a,4,7,7a-tetrahydro-1H-isoindole-1,3(2H)-dione (7b). Cycloadduct 4a (0.100 g, 0.250 mmol), Pd(OAc)$_2$ (0.028 g, 0.047 mmol), PPh$_3$ (0.024 g, 0.088 mmol), 3-iodoanisole (0.126 g, 0.538 mmol) and TBAF (0.128 g, 0.406 mmol) were used according to the general procedure mentioned above. The resulting brown colored oily crude reaction mixture was subjected to flash chromatography to yield the cross-coupled product 7b as a brown colored oily substance (0.073 g, 0.219 mmol, 87.7%): R$_f$ 0.15 (diethyl ether/hexanes, 2:1); $^1$H NMR (500 MHz, CDCl$_3$) 7.44 (t, J=8.1 Hz, 2H, H-10), 7.37 (t, J=7.5 Hz, 1H, H-11), 7.18-7.25 (m, 3H, H-9, 15), 7.08 (d, J=7.5 Hz, 1H, H-17), 6.90 (t, J=2.1 Hz, 1H), 6.81 (dd, J=6.8, 2.5 Hz, 1H), 6.27 (p, J=3.4 Hz, 1H, 1-6), 3.80 (s, 3H, H-18), 3.43 (ddd, J=9.4, 7.0, 2.5 Hz, 1H), 3.34 (ddd, J=9.4, 7.2, 2.5 Hz, 1H), 3.24 (dd, J=15.3, 2.5 Hz, 1H), 2.93 (ddd, J=15.3, 7.0, 2.5 Hz, 1H), 2.64 (ddt, J=15.3, 6.8, 2.3 Hz, 1H), 2.37-2.51 (m, 1H), $^{13}$C NMR (300 MHz, CDCl$_3$) δ 179.0 (C-), 178.8 (C-), 159.8 (C-), 141.9 (C-), 140.0 (C-), 132.0 (C-), 129.6 (C-), 129.1 (C-), 128.6 (C-), 126.4 (C-), 123.4 (C-), 118.0 (C-), 113.1 (C-), 111.2 (C-), 55.2 (C-), 40.1 (C-), 39.5 (C-), 27.7 (C-), 25.3 (C-); HRMS calcd for C$_{21}$H$_{19}$NO$_3$ (M$^+$) 333.1365, Anal. calcd for C$_{21}$H$_{19}$NO$_3$: C, 75.66; H, 5.74.

7d

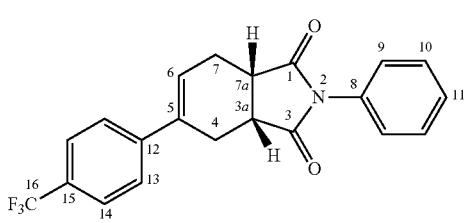

Synthesis of (3aR,7aS)-2-phenyl-5-(4-(trifluoromethyl) phenyl)-3a,4,7,7a-tetrahydro-1H-isoindole-1,3(2H)-dione (7d). Cycloadduct 4a (0.099 g, 0.247 mmol), Pd(OAc)$_2$ (0.023 g, 0.039 mmol), PPh$_3$ (0.024 g, 0.092 mmol), 1-iodo-4-(trifluoromethyl)benzene (0.132 g, 0.485 mmol) and TBAF (0.098 g, 0.311 mmol) were used according to the general procedure mentioned above. The resulting brown colored oily crude reaction mixture was subjected to flash chromatography to yield the cross-coupled product 7d as a colorless clear liquid (0.082 g, 0.221 mmol, 89.3%): R$_f$ 0.35 (diethyl ether/hexanes, 2:1); $^1$H NMR (500 MHz, CDCl$_3$) δ 7.58 (d, J=8.4 Hz, 2H, H-13), 7.46 (d, J=8.4 Hz, 2H, H-14), 7.42 (t, J=7.5 Hz, 2H, H-10), 7.36 (t, J=7.5 Hz, 1H, H-11), 7.14 (t, J=7.5 Hz, 2H, H-9), 6.31 (p, J=3.4 Hz, 1H, H-6), 3.47 (ddd, J=9.4, 7.1, 2.7 Hz, 1H, H-3a), 3.38 (ddd, J=9.4, 7.6, 2.5 Hz, 1H, H-7a), 3.27 (dd, J=15.3, 2.5 Hz, 1H, H-4), 2.99 (ddd, J=15.6, 7.1, 2.3 Hz, 1H, H-7), 2.65 (ddt, J=15.3, 6.7, 2.5 Hz, 1H, H-4), 2.37-2.54 (m, 1H, H-7); $^{13}$C NMR (300 MHz, CDCl$_3$) δ 178.8 (C-3), 178.7 (C-1), 143.7 (C-12), 139.1 (C-5), 131.8 (C-15), 129.1 (C-10), 128.7 (C-11), 126.3 (C-9), 125.8 (C-13, 14), 125.6 (q, C-16), 125.4 (C-6), 40.0 (C-3a), 39.3 (C-7a), 27.4 (C-4), 25.4 (C-7); HRMS calcd for $C_{21}H_{16}F_3NO_2$ (M$^+$) 371.1133, Anal. calcd for $C_{21}H_{16}F_3NO_2$: C, 67.92; H, 4.34.

In an embodiment, the present invention is directed to a compound selected from the group consisting of Formula I, Formula II, Formula III, Formula IV, Formula VI, and Formula VII:

Formula I
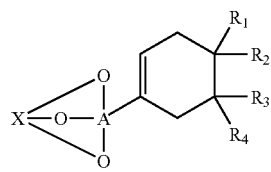

Formula II
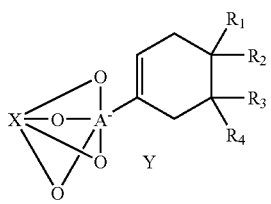

Formula III
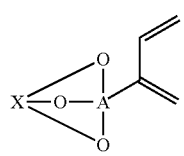

Formula IV
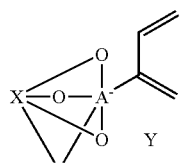

Formula VI
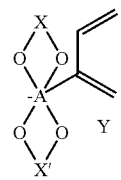

Formula VII
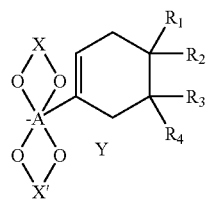

wherein A is a member selected from the group consisting of silicon, platinum, rhodium, boron, arsenic and palladium;

X and X' are independently aliphatic or aromatic groups which are each independently selected from the group consisting of alkyl, alkenyl, alkynyl, aryl, heteroaryl, heterocyclyl, wherein the alkyl, alkenyl, and alkynyl, groups may be substituted by one or more heteroatoms, and when one or more heteroatoms is present in the alkyl, alkenyl, and alkynyl groups and in the heteroaryl and heterocyclyl groups, the heteroatoms are selected from the group consisting of nitrogen, phosphorous, arsenic, antimony, bismuth, germanium, tin, oxygen, sulfur, selenium, tellurium, boron, aluminum, gallium, indium, germanium, and silicon, and wherein all of the alkyl, alkenyl, alkynyl, aryl, heteroaryl, heterocyclyl groups also may be optionally substituted by one or more of the following: alkyl, alkenyl, alkynyl, aryl, heteroaryl, heterocyclyl, halo, cyano, oxo, hydroxy, mercapto, sulfonyl, sulfoxy, amino, imino, alkylthio, alkoxy, alkoxyalkyl, mono-alkylamino, di-alkylamino, nitro, nitroso, and thioxo;

R$_1$, R$_2$, R$_3$, and R$_4$ are each independently selected from the group consisting of hydrogen, alkyl, alkenyl, alkynyl, aryl, heteroaryl, heterocyclyl, halo, cyano, hydroxy, mercapto, sulfonyl, sulfoxy, amino, alkylthio, alkoxy, alkoxyalkyl, mono-alkylamino, di-alkylamino, nitro, and nitroso, or R$_1$ and R$_2$ together with the atoms connected to them or R$_3$ and R$_4$ together with the atoms connected to them may form a spiro C$_{4-8}$ cycloalkyl group that may optionally contain one or more heteroatoms selected from the group consisting of nitrogen, phosphorous, arsenic, antimony, bismuth, germanium, tin, oxygen, sulfur, selenium, tellurium, boron, aluminum, gallium, indium, germanium, and silicon; or R$_1$ and R$_3$ together with the atoms connected to them or R$_2$ and R$_4$ together with the atoms connected to them may form a C$_{3-10}$ cycloalkyl group that may optionally contain one or more heteroatoms selected from the group consisting of nitrogen, phosphorous, arsenic, antimony, bismuth, germanium, tin, oxygen, sulfur, selenium, tellurium, boron, aluminum, gallium, indium, germanium, and silicon; and wherein Y is a counterion.

In a variation of the embodiment, A is silicon. In an alternate variation, X and X' represent an alkyl or alkenyl group optionally substituted by nitrogen, X and X' represent alkyl substituted by nitrogen, or X and X' represent an aryl group. In a variation, the aryl group is phenyl. In a variation, X is heteroaryl or heterocyclyl, or X is an alkyl, alkenyl, or alkynyl group substituted by one or more heteroatoms, the heteroatoms in the heteroaryl or heterocyclyl group or the heteroatoms in the alkyl, alkenyl, and alkynyl groups are one or more members selected from the group consisting of nitrogen, oxygen, sulfur, and selenium.

In another embodiment, Y is sodium, potassium, or tetrabutyl ammonium. In a variation of an embodiment, A is platinum.

In an embodiment, $R_1$, $R_2$, $R_3$, and $R_4$ together with the carbons to which they are attached is 1-phenyl-1H-pyrrole-2,5-dione.

In an embodiment, the present invention relates to a compound that is selected from the group consisting of

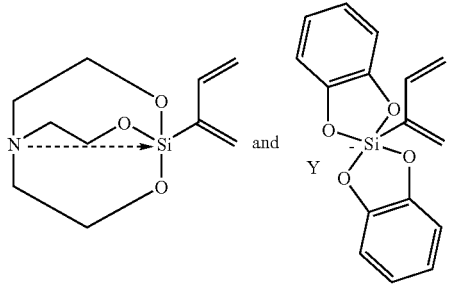 and wherein Y is a potassium ion.

In an embodiment, the present invention relates to a method of making compounds selected from the group consisting of Formulas I, II, and VII

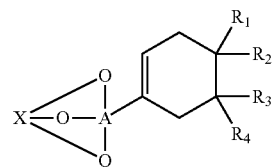

Formula I

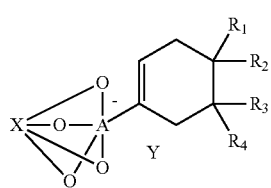

Formula II

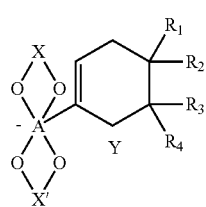

Formula VII comprising reacting the dienes selected from the group consisting of Formulas III, IV and VI,

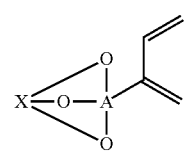

Formula III

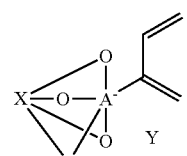

Formula IV

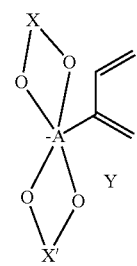

Formula VI respectively with the dienophile of Formula V

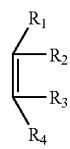

Formula V wherein in Formulas I, II, III, IV, V, VI, VII, A is a member selected from the group consisting of silicon, platinum, rhodium, boron, arsenic and palladium;

X and X' are independently aliphatic or aromatic groups which are each independently selected from the group consisting of alkyl, alkenyl, alkynyl, aryl, heteroaryl, heterocyclyl, wherein the alkyl, alkenyl, and alkynyl, groups may be substituted by one or more heteroatoms, and when one or more heteroatoms is present in the alkyl, alkenyl, and alkynyl groups and in the heteroaryl and heterocyclyl groups, the heteroatoms are selected from the group consisting of nitrogen, phosphorous, arsenic, antimony, bismuth, germanium, tin, oxygen, sulfur, selenium, tellurium, boron, aluminum, gallium, indium, germanium, and silicon, and wherein all of the alkyl, alkenyl, alkynyl, aryl, heteroaryl, heterocyclyl groups also may be optionally substituted by one or more of the following: alkyl, alkenyl, alkynyl, aryl, heteroaryl, heterocyclyl, halo, cyano, oxo, hydroxy, mercapto, sulfonyl, sulfoxy, amino, imino, alkylthio, alkoxy, alkoxyalkyl, mono-alkylamino, di-alkylamino, nitro, nitroso, and thioxo;

$R_1$, $R_2$, $R_3$, and $R_4$ are each independently selected from the group consisting of hydrogen, alkyl, alkenyl, alkynyl, aryl, heteroaryl, heterocyclyl, halo, cyano, hydroxy, mercapto, sulfonyl, sulfoxy, amino, alkylthio, alkoxy, alkoxyalkyl, mono-alkylamino, di-alkylamino, nitro, and nitroso, or $R_1$ and $R_2$ together with the atoms connected to them or $R_3$ and $R_4$ together with the atoms connected to them may form a spiro $C_{4-8}$ cycloalkyl group that may optionally contain one or more heteroatoms selected from the group consisting of nitrogen, phosphorous, arsenic, antimony, bismuth, germanium, tin, oxygen, sulfur, selenium, tellurium, boron, aluminum, gallium, indium, germanium, and silicon; or $R_1$ and $R_3$ together with the atoms connected to them or $R_2$ and $R_4$ together with the atoms connected to them may form a $C_{3-10}$ cycloalkyl group that may optionally contain one or more heteroatoms selected from the group consisting of nitrogen, phosphorous, arsenic, antimony, bismuth, germanium, tin, oxygen, sulfur, selenium, tellurium, boron, aluminum, gallium, indium, germanium, and silicon;

and wherein Y is a counterion.

In a variation of the embodiment, A is silicon. In a variation, X and X' independently represent an alkyl or alkenyl group substituted by one or more nitrogen atoms or X and X' represent an aryl group. In another variation, X and X' represent a phenyl group or an alkyl group substituted by a nitrogen atom.

In an embodiment, the diene is selected from the group consisting of

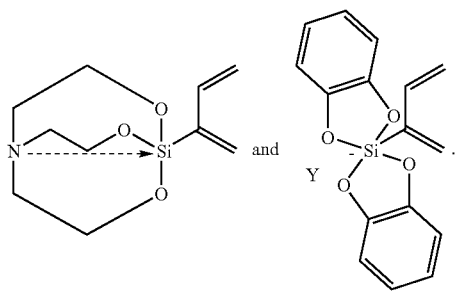

In a variation, Y is potassium, sodium, or tetrabutyl ammonium. In another variation, one of $R_1$ and $R_2$ is an electron withdrawing group. In another variation, $R_1$, $R_2$, $R_3$, and $R_4$ together with the carbons to which they are attached is 1-phenyl-1H-pyrrole-2,5-dione.

In an embodiment, the present invention relates to a compound of Formula IX

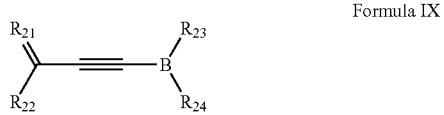

Formula IX wherein B is C or Si; $R_{21}$ and $R_{22}$ are independently hydrogen, alkyl, alkenyl, or $R_{21}$ and $R_{22}$ in conjunction with the carbon to which they are attached form a 3 to 8 membered carbocyclo ring; $R_{23}$ is hydrogen, alkyl, alkenyl, hydroxy, aryl or —O—Si($R_{26}$)($R_{27}$)($R_{28}$); $R_{24}$, $R_{25}$, $R_{26}$, $R_{27}$, and $R_{28}$ are each independently hydrogen, alkyl, alkenyl, or aryl.

In a variation, the compound contains silicon or alternatively, one of B and $R_{23}$ contains silicon.

In a variation, all of $R_{21}$, $R_{22}$, $R_{23}$, $R_{24}$, $R_{25}$, $R_{26}$, $R_{27}$, and $R_{28}$ are not hydrogen. In another variation, the aryl group is phenyl. In another variation, $R_{21}$ and $R_{22}$ together with the carbon to which they attached form a cyclohexenyl group.

The following references are noted:
1. Hayes, B. L. "Synthesis of 5- and 6-membered rings via transition-metal mediated cycloaddition reactions", Ph.D. Dissertation, Wake Forest University, 2000.
2. Hayes, B. L., Adams, T. A., Pickin, K. A., Day, C. S., Welker, M. E. "Preparation of Cobaloxime-Substituted Unsaturated Carbonyl Compounds and Their Subsequent Conversion into 1-Cobaloxime-Substituted 1,3-Dienyl Complexes"; Organometallics 2000, 19(14), 2730-40.
3. Wright, M. W., Smalley, T. L., Welker, M. E., Rheingold, A. L. "Synthesis of Cobalt Substituted 1,3-Diene Complexes with Unusual Structures and Their Exo Selective Diels-Alder Reactions"; J. Am. Chem. Soc. 1994, 116(15), 6777-91.
4. De, S., Welker, M. E. "Preparation of 2-BF3-Substituted-1,3-Dienes and Their Diels-Alder/Cross-Coupling Reactions"; Org. Lett. 2005, 7(12), 2481-84.
5. Wieland, H.; Ber. Dtsch. Chem. Ges. 1906, 39, 1492-99.
6. Albrecht, W. "first report on Diels-Alder reactions"; Justus Liebigs Ann. Chem. 1906, 348(31-49.
7. Diels, O., Alder, K.; Justus Liebigs Ann. chem. 1928, 460(98-122.
8. Nicolaou, K. C., Snyder, S. A., Montagnon, T., Vassilikogiannakis, G. "The Diels-Alder Reaction in Total Synthesis"; Angew. Chem. Int. Ed. 2002, 41(10), 1668-98.
9. Welker, M. E. "Org. Syn. Res. Group meeting presentation"; Wake Forest University, Chemistry Department, spring 2005, 01-47.
10. Boger, D. L. "Lecture Notes—Modern Organic Synthesis"; The Scripps Research Institute: CA, 1999.
11. Smith, M. B. "Organic Synthesis"; McGraw-Hill: New York, 1994.
12. Fringuelli, F., Taticchi, A. "Dienes in the Diels-Alder Reaction"; 3 ed.; John Wiley: New York, 1990.
13. Carey, F. A., Sundberg, R. J. "Advanced Organic Chemistry"; 3rd ed.; Plenum Press: New York, 1990.
14. Houk, K. N. "Frontier molecular orbital theory of cycloaddition reactions"; Acc. Chem. Res. 1975, 8(11), 361-69.
15. Houk, K. N. "Generalized frontier orbitals of alkenes and dienes. Regioselectivity in Diels-Alder reactions"; J. Am. Chem. Soc. 1973, 95(12), 4092-94.
16. Herndon, W. C. "Theory of cycloaddition reactions"; Chem. Rev. 1972, 72(2), 157-79.
17. Woodward, R. B., Hoffmann, R. "Stereochemistry of Electrocyclic Reactions"; J. Am. Chem. Soc. 1965, 87(2), 395-97.
18. Sustmann, R. "A simple model for substituent effects in cycloaddition reactions. II. The diels-alder reaction"; Tet. Lett. 1971, 12(29), 2721-24.
19. Alder, K., Stein, G.; Angew. Chem. 1937, 50(0), 510.
20. Lutz, E. F., Bailey, G. M. "Regulation of Structural Isomerism in Simple Diels-Alder Adducts"; J. Am. Chem. Soc. 1964, 86(18), 3899-901.
21. Welker, M. E. "Organocobalt Complexes in Organic Synthesis"; Curr. Org. Chem. 2001, 5(7), 785-807.
22. Pickin, K. A., Kindy, J. M., Day, C. S., Welker, M. E. "Simple preparation of cobaloxime dienyl complexes and their exo selective Diels-Alder cycloadducts-Progress towards transition metal-mediated Diels-Alder reactions which are catalytic in metal dienyl complex"; J. Organomet. Chem. 2003, 681(1-2), 120-33.
23. Richardson, B. M., Welker, M. E. "Transition metal-mediated exo-selective Diels-Alder reactions for the preparation of octalones with unusual stereochemistries. Reactions of 2-cobaloxime substituted 1,3-dienes with cyclohexenones in thermal and lewis acid catalyzed [4+2] cycloadditions"; J. Org. Chem. 1997, 62(5), 1299-304.
24. Rigby, J. H. "Transition metal-promoted higher order cycloaddition reactions"; JAI Press: Greenwich, 1995.

25. Rigby, J. H., Ateeq, H. S., Charles, N. R., Cuisiat, S. V., Ferguson, M. D., Henshilwood, J. A., Krueger, A. C., Ogbu, C. O., Short, K. M., Heeg, M. J. "Metal-promoted higher-order cycloaddition reactions. Stereochemical, regiochemical, and mechanistic aspects of the [6π+4π] reaction"; J. Am. Chem. Soc. 1993, 115(4), 1382-96.
26. Rigby, J. H., Ateeq, H. "Synthetic Studies on transition-metal-mediated higher order cycloaddition Reactions: highly stereoselective construction of substituted bicyclo[4.4.1]undecane systems"; J. Am. Chem. Soc. 1990, 112 (17), 6442-43.
27. Chapman, J. J., Day, C. S. Welker, M. E. "Enantioselective Diels2Alder Reactions of Optically Active (Buta-1,3-dien-2-yl)(salen)cobalt(III) Complexes"; Eur. J. Org. Chem. 2001, 12(2273-82.
28. Corey, E. J. "Catalytic Enantioselective Diels-Alder Reactions: Methods, Mechanistic Fundamentals, Pathways, and Applications"; Angew. Chem. Intl. Ed. 2002, 41(10), 1650-67.
29. Santelli, M., Pons, J. M. "Lewis Acids and Selectivity in Organic Synthesis"; Synthesis, CRC Press: Boca Raton, Fla., 1996.
30. Douglas, C. J. "Catalytic asymmetric synthesis of all-carbon quaternary stereocenters"; Proc. Natl. Acad. Sci. USA 2004, 101(15), 5363-67.
31. Corey, E. J., Letavic, M. A. "Enantioselective Total Synthesis of Gracilins B and C Using Catalytic Asymmetric Diels-Alder Methodology"; J. Am. Chem. Soc. 1995, 117 (37), 9616-17.
32. "Silicon Compounds: Silanes & Silicones"; Gelest Inc. (Catalog): Morrisville, Pa., 2006.
33. Colvin, E. W. "Silicon in Organic Synthesis"; Butterworth: London, 1981.
34. "Progress in Organosilicon Chemistry"; Gordon and Breach Publishers: Basel, Switzerland, 1995.
35. Thomas, S. E. "Organic Synthesis: The roles of Boron and Silicon"; Oxford Science Publications: New York, 1991.
36. Eaborn, C. "Organosilicon Compounds"; Academic Press Inc.: New York, 1960.
37. Bazant, V., Chvalvovsky, V. "Organosilicon Compounds"; Publishg House Of The Czechoslovak Academy of Sciences: Prague, 1965.
38. Brook, M. A. "Silicon in organic, organometallic, and polymer chemistry"; John Wiley & Sons, Inc: New York, 2000.
39. Rochow, G. C. "Chemistry of the silicones"; 2nd ed.; John Wiley & Sons, Inc: New York, 1951.
40. Luh, T., Wong, K. "Silyl-Substituted Conjugated Dienes: Versatile Building Blocks in Organic Synthesis"; Synthesis 1992, 349-70.
41. Stadnichuk, M. D., Voropaeva, T. I. "Silicon-containing alka-1,3-dienes and their functional derivatives in organic synthesis"; Russ. Chem. Rev. 1995, 64(1), 25-46.
42. Carter, M. J., Fleming, I. "Regioselectivity in the Diels-Alder Reaction of 1-Trimethylsilylbutadiene"; Chem. Comm. 1976, 17(681.
43. Carter, M. J., Fleming, I. "Allyl silanes in organic synthesis: some reactions of 3-trimethylsilylcyclohex-4-ene-1,2-dicarboxylic acid and its derivatives"; J. Chem. Soc., Chem. Commun. 1976, 17(679-80.
44. Chou, T., Tso, H., Tao, Y., Lin, L. C. "Convinient Syntheses of Precursors of Silylated 1,3-dienes"; J. Org. Chem. 1987, 52(2), 244-46.
45. Takenaka, K., Hattori, T., Hirao, A., and Nakahama, S. "Polymerization of monomers containing functional silyl groups. 6. Anionic polymerization of 2-(trialkoxysilyl)-1,3-butadiene"; Macromolecule 1989, 22(4), 1563-67.
46. Batt, D. G., Ganem, B. "Synthesis and cycloaddition reactions of 2-triethylsilyl-1,3-butadiene"; Tet. Lett. 1978, 19(36), 3323-24.
47. Fiandanese, V., Marchese, G., Naso, F., Ronzini, L.; Synthesis 1987, 1034.
48. Hyuga, S., Yamashina, N., Hara, S., Suzuki, A. "(E)-(2-Bromoethenyl)diisopropoxyborane. A New Building Block for (E)-Olefins"; Chem. Lett. 1988, 5(809-12.
49. Trost, B. M., Mignani, S. "Tandem Pd-Catalyzed Elimination-Cyclization"; J. Org. Chem. 1986, 51(18), 3435-39.
50. Ni, Z. J., Yang, P. F., Ng, D. K. P., Tzeng, Y. L., Luh, T. Y. "Unified Synthesis of Vinylsilanes and Silylated Butadienes. Nickel-Catalyzed Olefination and Silylolefination of Dithioacetals"; J. Am. Chem. Soc. 1990, 112(25), 9356-64.
51. Tamo, K., Kobayashi, K., Ito, Y. "Nickel(0)-Catalyzed cyclization of 1,7-Diynes via Hydrosilation: One-Step Synthesis of 1,2-Dialkylidenecyclohexanes with a (Z)-vinylsilane moiety"; J. Am. Chem. Soc. 1989, 111(16), 6478-80.
52. Ikeda, Z., Oshima, K., Matsubara, S. "Preparation and Reaction of 2-Aryl-3-silyl-1,3-butadiene"; Org. Lett. 2005, 7(22), 4859-61.
53. Kahle, K., Murphy, P. J., Scott, J., Tamagni, R. "Convinient synthesis of silyl substituted butadienes; a new route to silicon tethered intramolecular Diels-Alder reaction precursors"; J. Chem. Soc., Perkin Trans. 1 1997, 7(997-99.
54. Lauchli, R., Whitney, J. M., Zhu, L., Shea, K. J. "Synthesis and Chemistry of Bridgehead Allylsilanes. Stereoselective Reactions with Aldehydes"; Org. Lett. 2005, 7(18), 3913-16.
55. Hiyama, T., Hatanaka, Y. "Palladium-catalyzed cross-coupling reaction of organometalloids through activation with fluoride ion"; Pure Appl. Chem. 1994, 66(7), 1471.
56. Hiyama, T. "Metal Catalyzed Cross-Coupling Reactions"; John Wiley & Sons Weinheim, Germany, 1998.
57. Hiyama, T., Shirakawa, E. "Organosilicon Compounds"; Top. in Curr. Chem. 2002, 219(61-85.
58. Stille, J. K. "The Palladium-Catalyzed Cross-Coupling Reactions of Organotin Reagents with Organic Electrophiles [New Synthetic Methods (58)]"; Angew. Chem. Intl. Ed. 1986, 25(6), 508-24.
59. Murata, M., Ishikura, M., Nagata, M., Watanabe, S., Masuda, Y. "Rhodium(I)-Catalyzed Silylation of Aryl Halides with Triethoxysilane: Practical Synthetic Route to Aryltriethoxysilanes"; Org. Lett. 2002, 4(11), 1843-45.
60. Hazme, A., Provot, O., Alami, M., Brion, J.-D. "Platinum Oxide Catalyzed Silylation of Aryl Halides with Triethylsilane: An Efficient Synthetic Route to Functionalized Aryltriethylsilanes"; Org. Lett. 2006, 8(5), 931-34.
61. Hatanaka, Y., Hiyama, T. "Cross-coupling of organosilanes with organic halides mediated by a palladium catalyst and tris(diethylamino)sulfonium difluorotrimethylsilicate"; J. Org. Chem. 1988, 53(4), 918-20.
62. Hatanaka, Y., Hiyama, T. "Alkenylfluorosilanes as widely applicable substrates for the palladium-catalyzed coupling of alkenylsilane/fluoride reagents with alkenyl iodides"; J. Org. Chem. 1989, 54(2), 268-70.
63. Hatanaka, Y., Hiyama, T. "On the regioselectivity of palladium catalyzed cross-coupling reactions of alkenylsilanes: Participation of β-cationic organosilicate-palladium species during the transmetallation"; J. Organomet. Chem. 1994, 465(1-2), 97-100.
64. Hatanaka, Y., Hiyama, T. "A wide range of organosilicon compounds couples with enol and aryl triflates in the presence of Pd catalyst and fluoride ion"; Tet. Lett. 1990, 31(19), 2719.

65. Denmark, S. E., Sweis, R. F. "Cross-Coupling Reactions of Organosilicon Compounds: New Concepts and Recent Advances"; Chem. Pharm. Bull. 2002, 50(12), 1531-41.
66. Denmark, S. E., Choi, J. Y. "Highly Stereospecific, Cross-Coupling Reactions of Alkenylsilacyclobutanes"; J. Am. Chem. Soc. 1999, 121(24), 5821-22.
67. Denmark, S. E., Griedel, B. D., Coe, D. M., Schnute, M. E. "Chemistry of Enoxysilacyclobutanes: Highly Selective Uncatalyzed Aldol Additions"; J. Am. Chem. Soc. 1994, 116(16), 7026-43.
68. Denmark, S. E., Choi, J. Y. "Mild and General Cross-Coupling of (-Alkoxyvinyl)silanols and -silyl Hydrides"; Org. Lett. 2000, 2(20), 3221-24.
69. Denmark, S. E., Pan, W. "Efficient and stereoselective cross-coupling with highly substituted alkenylsilanols"; J. Organomet. Chem. 2002, 653(1-2), 98-104.
70. Denmark, S. E., Pan, W. "Intramolecular Hydrosilylation and Silicon-Assisted Cross-Coupling: An Efficient Route to Trisubstituted Homoallylic Alcohols"; Org. Lett. 2001, 3(1), 61-64.
71. Mowery, M. E., Deshong, P. "Cross-Coupling Reactions of Hypervalent Siloxane Derivatives: An Alternative to Stille and Suzuki Couplings"; J. Org. Chem. 1999, 64(5), 1684-88.
72. Monoso, A. S., Deshong, P. "Improved Synthesis of Aryl-triethoxysilanes via Palladium(0)-Catalyzed Silylation of Aryl Iodides and Bromides with Triethoxysilane"; J. Org. Chem. 2001, 66(22), 7449-55.
73. Murata, M., Suzuki, K., Watanabe, S., Masuda, Y. "Synthesis of Arylsilanes via Palladium(0)-Catalyzed Silylation of Aryl Halides with Hydrosilane"; J. Org. Chem. 1997, 62(24), 8569-71.
74. Riggleman, S., Deshong, P. "Application of Silicon-Based Cross-Coupling Technology to Triflates"; J. Org. Chem. 2003, 68(21), 8106-09.
75. Seganish, W. M., Deshong, P. "Preparation and Palladium-Catalyzed Cross-Coupling of Aryl Triethylammonium Bis(catechol) Silicates with Aryl Triflates"; J. Org. Chem. 2004, 69(4), 1137-43.
76. Hirabayashi, K., Kawashima, J., Nishihara, Y., Mori, A., Hiyama, T. "A New Transformation of Silanols. Palladium-Catalyzed Cross-Coupling with Organic Halides in the Presence of Silver(I) Oxide"; Org. Lett. 1999, 1(2), 299-302.
77. Nakao, Y., Imanaka, H., Sahoo, A. K., Yada, A., Hiyama, T. "Alkenyl- and Aryl[2-(hydroxymethyl)phenyl]dimethylsilanes: An Entry to Tetraorganosilicon Reagents for the Silicon-Based Cross-Coupling Reaction"; J. Am. Chem. Soc. 2005, 127(19), 6952-53.
78. Dilman, A. D., Belyakov, P. A., Korlyukov, A. A., Struchkova, M. I., Tartakovsky, V. A. "Synthesis of Pentafluorophenylmethylamines via Silicon Mannich Reaction"; Org. Lett. 2005, 7(14), 2913-15.
79. Ho, T. L. "Tandem Organic Reactions (Chapter-7)"; 1st ed.; John Wiley & Sons, Inc: New York, 1992.
80. Borthis, C. "Tandem Reaction Sequences; Power Point presentation"; McMillan Gr. Meeting 2000.
81. Tietze, L. F. "Domino Reactions in Organic Synthesis"; Chem. Rev. 1996, 96(1), 115-36.
82. Meijere, A. D., Zerschwitz, P. V., Brase, S. "The Virtue of Palladium-Catalyzed Domino Reactions—Diverse Oligocyclizations of Acyclic 2-Bromoenynes and 2-Bromoenediynes"; Acc. Chem. Res. 2005, 38(5), 413-22.
83. Sato, F.; Nissan Chemical Industries, Ltd., Japan: United States, 1989.
84. Bosque, R., Crespo, M., Evangelio, E., Font-Bardi, M., Solans, X. "Oxidative addition to dimethylplatinum (II) compounds containing bulky nitrogen ligands: crystal structures of compounds [PtMe$_3$I{(Me$_2$NCH$_2$CH$_2$NCH)Ar}](Ar=phenanthryl or anthryl)"; J. Organomet. Chem. 2005, 690(8), 2062-70.
85. Crespo, M., Evangelio, E. "Five- and six-membered platinacycles derived from phenantryl and anthracenyl imines"; J. Organomet. Chem. 2004, 689(11), 1956-64.
86. Jenkins, H. A., Klempner, M. J., Prokopchuk, E. M., Puddephatt, R. J. "Dimethyl(hydrido)platinum(IV) chemistry related to methane activation: the effect of a tetradentate ligand"; Inorg. Chim. Acta 2003, 352(72-78.
87. Osakada, K., Yamamoto, T. "Transmetallation of alkynyl and aryl complexes of Group 10 transition metals"; Coordination Chemistry Reviews 2000, 198(1), 379-99.
88. Budnikova, Y. G., Kargin, Y. M., Sinyashin, O. G. "Mechanism of Electrochemical Coupling of Aryl Halides, Catalyzed by Nickel 2,2'-Bipyridine Complexes"; Russ. J. of Gen. Chem. 2000, 70(1), 116-20.
89. Jenkins, H. A., Yap, G. P., Puddephatt, R. J. "Cationic Methyl(hydrido)platinum(IV) Complexes"; Organometallics 1997, 16(9), 1946-55.
90. Welker, M. E. "Preparation and Tandem Reactions of Main Group Substituted Dienes," Wake Forest University, NC 27109, 2005.
91. Pidaparthi, R. R., Welker, M. E., Day, C. S. "[6+4] and [4+2] Cycloaddition Reactions of Cobaloxime 1,3-Dienyl Complexes and Tropones"; Organometallics 2006, 25(4), 974-81.
92. Nunomoto, S., Yamashita, Y. "Reaction of 2-(1,3-butadienyl)magnesium chloride with carbonyl compounds and epoxides. A regioselectivity study"; J. Org. Chem. 1979, 44(26), 4788-91.
93. Stradiotto, M., Crowe, G., Ruffolo, R., Brook, M. A. "1-Styrylsilatrane"; Acta Cryst. 1997, C53(637-39.
94. Schmidt, M. W., Windus, T. L., Gordon, M. S. "Structural Trends in Silicon Atranes"; J. Am. Chem. Soc. 1995, 117(28), 7480-86.
95. House, S. E., Poon, K. W., Lam, H., Dudley, G. B. "p-Siletanylbenzylidene Acetal: Oxidizable Protecting Group for Diols"; J. Org. Chem. 2005, 71(1), 420-22.
96. Horyath, A., Backvall, J. E. "Palladium(II)-Catalyzed SN2' Reactions of -Allenic Acetates. Stereoconvergent Synthesis of (Z,E)-2-Bromo-1,3-dienes"; J. Org. Chem. 2001, 66(24), 8120-26.
97. Ma, S., Hou, H., Zhao, S., Wang, G. "Efficient Synthesis of Optically Active 2,3-Allenols via the Simple CuBr-Mediated Reaction of Optically Active Propargylic Alcohols with Paraformaldehyde"; Syn. 200212), 1643-45.
98. Ma, S., Wang, G. "Unexpected SN2'-type addition-elimination reactions of 1-aryl-2,3-allenols with LiX. Synthesis and synthetic application of 1-aryl-3-halo-1,3-dienes"; Tet. Lett. 2002, 43(33), 5723-26.
99. Price, J. M., Williamson, R. F., Schramm, B. B., Wayland, B. B.; Inorg. Chem. 1972, 11(1280.
100. Price, J. H., Williamson, A. N., Schramm, R. F., Wayland, B. B.; Inorg. Chem. 1972, 11(1280.
101. Kleij, A. W., Gebbink, J. M., Lutz, M., Spek, A. L., Koten, G. "Synthesis and characterization of platinum(II)-terminated dendritic carbosilanes: X-ray crystal structure of the model species [PtCl(C$_6$H$_3$){CH$_2$NMe$_2$}-2-SiMe$_{3-5}$)(PPh$_3$)]"; J. Organomet. Chem. 2001, 621(1-2), 190-96.
102. Tsuji, J., Sato, K., Okumoto, H. "Palladium-catalyzed decarboxylation-carbonylation of allylic carbonates to form .beta., .gamma.-unsaturated esters"; J. Org. Chem. 1984, 49(8), 1341-44.

103. Tamo, K., Kawachi, A., Ito, Y. "Progress in Organosilicon Chemistry (Chapter-III: The Chemistry of Functional Silyl Anions)"; Gordon and Breach Publishers: Basel, Switzerland, 1995.

104. Kawachi, A., Oishi, Y., Kataoka, T., Tamao, K. "Preparation of Sulfur-Substituted Silyllithiums and Their Thermal Degradation to Silylenes"; Organometallics 2004, 23(12), 2949-55.

105. Tamao, K., Nakajo, E., Ito, Y. "Silafunctional compounds in organic synthesis. 40.1 metalated (allyl)aminosilanes: a γ-regioselective reaction with aldehydes and an approach to the synthesis of 2-deoxy-c-nucleoside skeletons"; Tetrahedron 1988, 44(13), 3997-4007.

106. Tsuji, H., Fukazawa, A., Yamaguchi, S., Toshimitsu, A., Tamao, K. "all-anti-Pentasilane: Conformation Control of Oligosilanes Based on the Bis(tetramethylene)-Tethered Trisilane Unit"; Organometallics 2004, 23(14), 3375-77.

107. Katayama, H., Nagao, M., Ozawa, F., Ikegami, M., Arai, T. "Stereoselective Synthesis of cis- and trans-Oligo(phenylenevinylene)s via Palladium-Catalyzed Cross-Coupling Reactions"; J. Org. Chem. 2005, 71(7), 2699-705.

108. Lettan II, R. B., Scheidt, K. A. "Lewis Base-Catalyzed Additions of Alkynes Using Trialkoxysilylalkynes"; Org. Lett. 2005, 7(15), 3227-30.

109. Lee, H. Y., Kim, B. G., Snapper, M. L. "A Stereoselective Enyne Cross Metathesis"; Org. Lett. 2003, 5(11), 1855-58.

110. Yoshikai, N., Mashima, H., Nakamura, E. "Nickel-Catalyzed Cross-Coupling Reaction of Aryl Fluorides and Chlorides with Grignard Reagents under Nickel/Magnesium Bimetallic Cooperation"; J. Am. Chem. Soc. 2005, 127(51), 17978-79.

111. Lauchli, R., Whitney, J. M., Zhu, L., Shea, K. J. "Synthesis and Chemistry of Bridgehead Allylsilanes. Stereoselective Reactions with Aldehydes"; Org. Lett. 2005, 7(18), 3913-16.

112. Hayashi, T., Takahashi, M., Takaya, Y., Ogasawara, M. "Catalytic Cycle of Rhodium-Catalyzed Asymmetric 1,4-Addition of Organoboronic Acids. Arylrhodium, Oxa-allylrhodium, and Hydroxorhodium Intermediates"; J. Am. Chem. Soc. 2002, 124(18), 5052-58.

113. Otomaru, Y., Hayashi, T. "Rhodium-catalyzed asymmetric 1,4-addition of alkenylsilanes generated by hydrosilylation of alkynes: a one-pot procedure where a rhodium/(S)-binap complexcatalyzes the two successive reactions"; Tetrahedron: Asymmetry 2004, 15(17), 2647-51.

114. Oi, S., Taira, A., Honma, Y., Inoue, Y. "Asymmetric 1,4-Addition of Organosiloxanes to r,Â-Unsaturated Carbonyl Compounds Catalyzed by a Chiral Rhodium Complex"; Org. Lett. 2003, 5(1), 97-99.

115. Shen, W., Wang, L. "The Stille Reaction of 1,1-Dibromo-1-alkenes: Preparation of Trisubstituted Alkenes and Internal Alkynes"; J. Org. Chem. 1999, 64(24), 8873-79.

116. Ogasawara, M., Ikeda, H., Hayashi, T. "pi-Allylpalladium-Mediated Catalytic Synthesis of Functionalized Allenes"; Angew. Chem. Intl. Ed. 2000, 39(6), 1042-44.

117. Ruitenberg, K., Kleijn, H., Westmijze, H., Meijer, J., Vermeer, P. "Organometal-mediated synthesis of conjugated allenynes, allenediynes, vinylallenes and diallenes"; Receuil, J. Roy. Neth. Chem. Soc. 1982, 101(11), 405-09.

118. Krijnen, E. S., Zuilhof, H., Lodder, G. "Electronic and Conformational Effects in the Photochemistry of .alpha.-Alkenyl-Substituted Vinyl Halides"; J. Org. Chem. 1994, 59(26), 8139-50.

119. Denmark, S. E., Pan, W. "Intramolecular Anti-Hydrosilylation and Silicon-Assisted Cross-Coupling: Highly Regio- and Stereoselective Synthesis of Trisubstituted Homoallylic Alcohols"; Org. Lett. 2002, 4(23), 4163-66.

120. Denmark, S. E., Kobayashi, T. "Tandem Intramolecular Silylformylation and Silicon-Assisted Cross-Coupling Reactions. Synthesis of Geometrically Defined, alpha, beta-Unsaturated Aldehydes"; J. Org. Chem. 2003, 68(13), 5153-59.

121. Maifeld, S. V., Lee, D. "Unusual Tandem Alkynylation and trans-Hydrosilylation To Form Oxasilacyclopentenes"; Org. Lett. 2005, 7(22), 4995-98.

122. Schelper, M., Meijere, A. D. "Facile Construction of Spirocyclopropanated Bi-, Tri- and Tetracyclic Skeletons by Novel Cascades Involving Intra- and Intermolecular Heck Reactions of 2-Bromo-1,6-enynes and Bicyclopropylidene"; Eur. J. Org. Chem. 2005, 2005(3), 582-92.

123. Feuerstein, M., Chahen, L., Doucet, H., Santelli, M. "Efficient synthesis of enynes by tetraphosphine-palladium-catalyzed reaction of vinyl bromides with terminal alkynes"; Tetrahedron 2006, 62(1), 112-20.

124. Franks, M. A., Schrader, E. A., Pietsch, C., Pennella, D. R., Tortib, S. V., Welker, M. E. "Oxathiolene oxide synthesis via chelation-controlled addition of organometallic reagents to alkynols followed by addition of sulfur electrophiles and evaluation of oxathiolene oxides as anticarcinogenic enzyme inducers"; Bio 2005, 13(6), 2221-33.

125. Cane, F., Cerveau, G., Chuit, C., Corriu, J. P. R., Nayyar, K. N., Reye, C.; "Hexacoordination at silicon: the case of silatranes"; Organometallics 1990, 9(7), 1989-91.

126. Hosomi, A., Kohra, S., Tominaga, Y.; "Pentacoordinate organosilicon compounds in organic synthesis: Cross-coupling of alkenylsiliconates with organic halides and triflates catalyzed by palladium complex"; Chem. Pharm. Bull. 1988, 36(11), 4622-25.

127. GlassContour.com

128. Pidaparthi, R. R.; Welker, M. E.; Day, C. S.; Wright, M. W. Org. Lett. 2007, 9(9), 1623-26

129. Pidaparthi, R. R.; Welker, M. E. Tetrahedron Lett. 2007 doi: 10.1016/j.tetlet.2007.08.133

130. House, S. E.; Poon, K. W. C.; Lam, H.; Dudley, G. B. J. Org. Chem. 2006, 71(1), 420-22

131. Hyuga, S.; Chiba, Y.; Yamashina, N.; Hara, S.; Suzuki, A. Chem. Lett. 1987, 9, 1757-60

132. Hurley, A. L.; Welker, M. E.; Day, C. S. J. Organomet. Chem. 2000, 598(1), 150-59.

133. Li, Z. B.; Pu, L. Org. Lett. 2004, 6(6), 1065-68.

134. Tamao, K.; Maeda, K.; Tanaka, T.; Ito, Y. Tet. Lett. 1988, 29(52), 6955-56.

135. Roush, W. R.; Halvorsen, G. T. Org. Lett. 2007, 9(11), 2243-46.

Although specific embodiments are shown to generate cyclic compounds in a Diels Alder type fashion, the present invention should not be construed so as to be limited to just those embodiments. It should be understood that the above examples are given only for the sake of showing that the reaction process can make a particular compound in the disclosed genus. The above procedure can be generalized so that all of the compounds in the disclosed genus can be made. Any one or more feature from any of the disclosed embodiments above can be combined with any one or more feature from any other embodiment. The above written description is not meant to limit the invention in any way. Rather, the below claims define the invention.

We claim:
1. A compound selected from the group consisting of Formula III, Formula IV, Formula I, Formula II, Formula VI, and Formula VII:

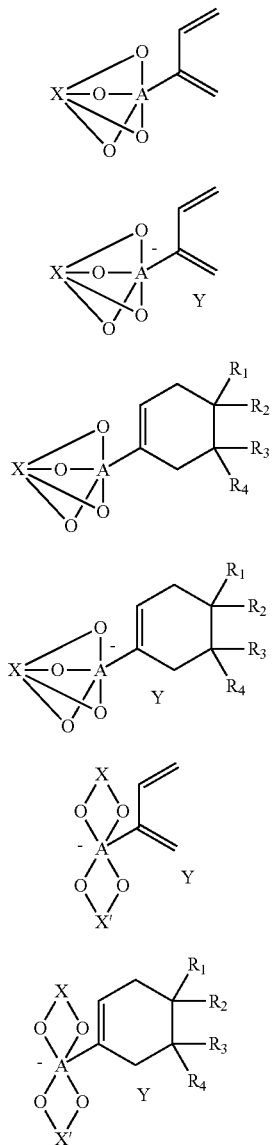

wherein A is a member selected from the group consisting of silicon and boron;

X and X' are independently aliphatic or aromatic groups which are each independently selected from the group consisting of alkyl, alkenyl, alkynyl, aryl, heteroaryl, heterocyclyl, wherein the alkyl, alkenyl, and alkynyl, groups may be substituted by one or more heteroatoms, and when one or more heteroatoms is present in the alkyl, alkenyl, and alkynyl groups and in the heteroaryl and heterocyclyl groups, the heteroatoms are selected from the group consisting of nitrogen, phosphorous, arsenic, antimony, bismuth, germanium, tin, oxygen, sulfur, selenium, tellurium, boron, aluminum, gallium, indium, germanium, and silicon;

and wherein all of the alkyl, alkenyl, alkynyl, aryl, heteroaryl, heterocyclyl groups also may be optionally substituted by one or more of the following: alkyl, alkenyl, alkynyl, aryl, heteroaryl, heterocyclyl, halo, cyano, oxo, hydroxy, mercapto, sulfonyl, sulfoxy, amino, imino, alkylthio, alkoxy, alkoxyalkyl, mono-alkylamino, di-alkylamino, nitro, nitroso, and thioxo;

$R_1$, $R_2$, $R_3$, and $R_4$ are each independently selected from the group consisting of hydrogen, alkyl, alkenyl, alkynyl, aryl, heteroaryl, heterocyclyl, halo, cyano, hydroxy, mercapto, sulfonyl, sulfoxy, amino, alkylthio, alkoxy, alkoxyalkyl, mono-alkylamino, di-alkylamino, nitro, and nitroso, or $R_1$ and $R_2$ together with the atoms connected to them or $R_3$ and $R_4$ together with the atoms connected to them may form a spiro $C_{4-8}$ cycloalkyl group that may optionally contain one or more heteroatoms selected from the group consisting of nitrogen, phosphorous, arsenic, antimony, bismuth, germanium, tin, oxygen, sulfur, selenium, tellurium, boron, aluminum, gallium, indium, germanium, and silicon; or $R_1$ and $R_3$ together with the atoms connected to them or $R_2$ and $R_4$ together with the atoms connected to them may form a $C_{3-10}$ cycloalkyl group that may optionally contain one or more heteroatoms selected from the group consisting of nitrogen, phosphorous, arsenic, antimony, bismuth, germanium, tin, oxygen, sulfur, selenium, tellurium, boron, aluminum, gallium, indium, germanium, and silicon; and wherein Y is a counterion.

2. The compound of claim 1, wherein A is silicon.

3. The compound of claim 2, wherein X and X' represent an alkyl or alkenyl group optionally substituted by nitrogen.

4. The compound of claim 3, wherein X and X' represent alkyl substituted by nitrogen.

5. The compound of claim 2, wherein X and X' represent an aryl group.

6. The compound of claim 5, wherein the aryl group is phenyl.

7. The compound of claim 2, wherein Y is sodium, potassium, or tetra-butyl ammonium.

8. The compound of claim 2, wherein when X is heteroaryl or heterocyclyl, or X is an alkyl, alkenyl, or alkynyl group substituted by one or more heteroatoms, the heteroatoms in the heteroaryl or heterocyclyl group or the heteroatoms in the alkyl, alkenyl, and alkynyl groups are one or more members selected from the group consisting of nitrogen, oxygen, sulfur, and selenium.

9. The compound of claim 2, wherein $R_1$, $R_2$, $R_3$, and $R_4$ together with the carbons to which they are attached is 1-phenyl-1H-pyrrole-2,5-dione.

10. The compound of claim 2, wherein the compound is selected from the group consisting of

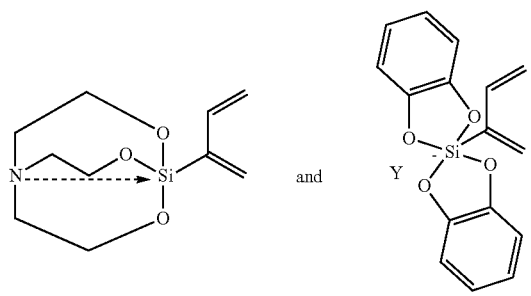

wherein Y is a potassium ion.

11. A method of making compounds selected from the group consisting of Formulas I, II, and VII

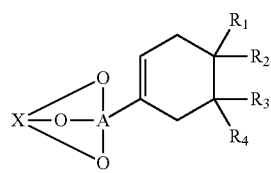

Formula I

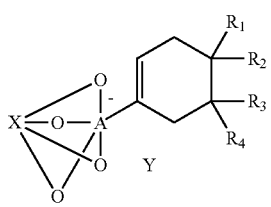

Formula II

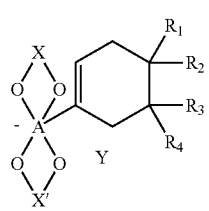

Formula VII comprising reacting the dienes selected from the group consisting of Formulas III, IV and VI,

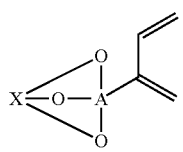

Formula III

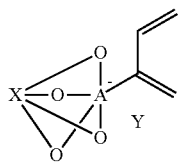

Formula IV

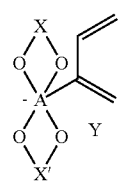

Formula VI respectively with the dienophile of Formula V

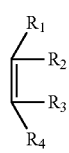

Formula V wherein in Formulas I, II, III, IV, V, VI, VII, A is a member selected from the group consisting of silicon and boron;

X and X' are independently aliphatic or aromatic groups which are each independently selected from the group consisting of alkyl, alkenyl, alkynyl, aryl, heteroaryl, heterocyclyl, wherein the alkyl, alkenyl, and alkynyl, groups may be substituted by one or more heteroatoms, and when one or more heteroatoms is present in the alkyl, alkenyl, and alkynyl groups and in the heteroaryl and heterocyclyl groups, the heteroatoms are selected from the group consisting of nitrogen, phosphorous, arsenic, antimony, bismuth, germanium, tin, oxygen, sulfur, selenium, tellurium, boron, aluminum, gallium, indium, germanium, and silicon, and wherein all of the alkyl, alkenyl, alkynyl, aryl, heteroaryl, heterocyclyl groups also may be optionally substituted by one or more of the following: alkyl, alkenyl, alkynyl, aryl, heteroaryl, heterocyclyl, halo, cyano, oxo, hydroxy, mercapto, sulfonyl, sulfoxy, amino, imino, alkylthio, alkoxy, alkoxyalkyl, mono-alkylamino, di-alkylamino, nitro, nitroso, and thioxo;

$R_1$, $R_2$, $R_3$, and $R_4$ are each independently selected from the group consisting of hydrogen, alkyl, alkenyl, alkynyl, aryl, heteroaryl, heterocyclyl, halo, cyano, hydroxy, mercapto, sulfonyl, sulfoxy, amino, alkylthio, alkoxy, alkoxyalkyl, mono-alkylamino, di-alkylamino, nitro, and nitroso, or $R_1$ and $R_2$ together with the atoms connected to them or $R_3$ and $R_4$ together with the atoms connected to them may form a spiro $C_{4-8}$ cycloalkyl group that may optionally contain one or more heteroatoms selected from the group consisting of nitrogen, phosphorous, arsenic, antimony, bismuth, germanium, tin, oxygen, sulfur, selenium, tellurium, boron, aluminum, gallium, indium, germanium, and silicon; or $R_1$ and $R_3$ together with the atoms connected to them or $R_7$ and $R_4$ together with the atoms connected to them may form a $C_{3-10}$ cycloalkyl group that may optionally contain one or more heteroatoms selected from the group consisting of nitrogen, phosphorous, arsenic, antimony, bismuth, germanium, tin, oxygen, sulfur, selenium, tellurium, boron, aluminum, gallium, indium, germanium, and silicon;

and wherein Y is a counterion.

12. The method of claim 11, wherein A is silicon.

13. The method of claim 12, wherein X and X' independently represent an alkyl or alkenyl group substituted by one or more nitrogen atoms or X and X' represent an aryl group.

14. The method of claim 12, wherein X and X' represent a phenyl group or an alkyl group substituted by a nitrogen atom.

15. The method of claim 14, wherein the diene is selected from the group consisting of

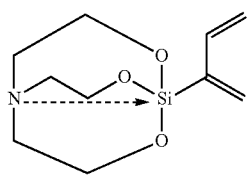 and 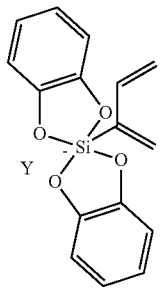

wherein Y is a potassium ion.

16. The method of claim 12, wherein Y is potassium, sodium, or tetrabutyl ammonium.

17. The method of claim 12, wherein one of $R_1$ and $R_2$ is an electron withdrawing group.

18. The method of claim 11, wherein $R_1$, $R_2$, $R_3$, and $R_4$ in Formula V together with the carbons to which they are attached is 1-phenyl-1H-pyrrole-2,5-dione.

* * * * *